(12) United States Patent
Judice et al.

(10) Patent No.: US 6,395,724 B1
(45) Date of Patent: May 28, 2002

(54) MULTIBINDING INHIBITORS OF CYCLOOXYGENASE-2

(75) Inventors: J. Kevin Judice, Montara; Deborah L. Higgins, San Carlos; John H. Griffin, Atherton, all of CA (US)

(73) Assignee: Advanced Medicine, Inc., South San Francisco, CA (US)

( * ) Notice: Subject to any disclaimer, the term of this patent is extended or adjusted under 35 U.S.C. 154(b) by 0 days.

(21) Appl. No.: 09/326,916

(22) Filed: Jun. 7, 1999

Related U.S. Application Data

(60) Provisional application No. 60/120,281, filed on Feb. 16, 1999, provisional application No. 60/093,072, filed on Jul. 16, 1998, and provisional application No. 60/088,448, filed on Jun. 8, 1998.

(51) Int. Cl.[7] .................. A01N 43/00; A01N 47/78; A61K 31/33; A61K 31/425; C07D 277/04; C07D 513/02; C07D 275/02; C07D 261/02; C07D 231/10; C07D 307/02; C07C 303/00; C07C 315/00

(52) U.S. Cl. .............. 514/183; 435/DIG. 34; 514/277; 514/365; 514/368; 514/372; 514/374; 514/378; 514/396; 514/399; 514/406; 514/427; 514/439; 514/473; 514/690; 514/764; 544/139; 546/192; 546/271.4; 546/272.1; 546/334; 548/146; 548/154; 548/162; 548/204; 548/206; 548/215; 548/225; 548/228; 548/229; 548/234; 548/235; 548/236; 548/240; 548/243; 548/245; 548/248; 548/311.1; 548/311.4; 548/315.4; 548/323.5; 548/333.1; 548/342.1; 548/342.5; 548/363; 548/373.1; 549/295; 549/313; 549/318; 564/80; 568/34; 568/381

(58) Field of Search ............ 544/139; 546/192, 546/334, 271.4, 272.1; 548/204, 206, 236, 225, 228, 229, 234, 235, 363, 243, 245–248, 333.1, 311.4, 311.1, 315.4, 323.5, 325.5, 342.1, 342.5, 146, 215, 154, 162, 240, 373.1; 549/313, 318, 295; 435/DIG. 22, 34; 564/80; 568/34, 381; 514/183, 277, 365, 368, 372, 374, 378, 396, 399, 406, 427, 439, 473, 690, 764

(56) References Cited

U.S. PATENT DOCUMENTS

| | | |
|---|---|---|
| 5,463,564 A | 10/1995 | Agrafiotis et al. |
| 5,559,103 A | 9/1996 | Gaeta et al. |
| 5,616,601 A | 4/1997 | Khanna et al. |
| 5,643,933 A | 7/1997 | Talley et al. |
| 5,691,374 A | 11/1997 | Black et al. |
| 5,783,698 A | 7/1998 | Smith |

FOREIGN PATENT DOCUMENTS

| | | |
|---|---|---|
| GB | 2 319 032 A | 5/1998 |
| WO | 92/05802 | 4/1992 |
| WO | 97/16405 | 5/1997 |
| WO | 97/21445 | 6/1997 |
| WO | WO 97/38986 | 10/1997 |

OTHER PUBLICATIONS

Fukuyama et al. Tet. Letters, vol. 34, No. 47, pp. 7633–7636, Nov. 1993.*
Fukuyama et al. Tet. Letters, vol. 34, No. 47, pp. 7637–7638, Nov. 1993.*
Woo et al. Phytochemistry, vol. 33, No. 4, pp. 939–940, Jul. 1993.*
Portoghese, P.S. "the Role of Concepts in Structural–Activity Relationship Studies of Opioid Ligands." *J. Med. Chem.* 35(11): 1927–1937 (1992).
R. Liang et al., *Science* 1996, 274, 1520–1522.
S.B. Shuker et al., *Science* 1996, 274, 1531–1534.
K.D. Stewart et al., *Bioorg. Med . Chem. Lett.* 1998, 8, 529–534.
W. L. Smith et al., *Adv. Immunol.* 1996, 62, 167–215.
D. Picot et al., *Nature* 1994, 367, 243–249.
C. Luong et al., *Nat. Struct. Biol.* 1996, 3, 927–933.
R. G. Kurumbail et al., *Nature* 1996, 384, 644–648.
J. K. Gierse et al, *J. Biol. Chem.* 1996, 271, 15810–15814.
E. Wong et al., *J. Biol. Chem.* 1997, 272, 9280–9286.
P. Prasit et al., *Annual Reports in Medicinal Chemistry* 1997, 32, 211–220.
Khanna et al. *J. Med. Chem.* 1997, 40, 1619–1633; 1634–1647.

* cited by examiner

*Primary Examiner*—Padmashri Ponnaluri
*Assistant Examiner*—Maurie E. Garcia
(74) *Attorney, Agent, or Firm*—David K. Boone; Jeffrey A. Hagenah

(57) ABSTRACT

Disclosed are multibinding compounds which inhibit cyclooxygenase-2 (COX-2), an enzyme which catalyzes the first committed step in the biosynthesis of prostaglandins. The multibinding compounds of this invention containing from 2 to 10 ligands covalently attached to one or more linkers. Each ligand is a moiety capable of binding to COX-2. The multibinding compounds of this invention are useful in the treatment inflammation, pain, fever and the like.

10 Claims, 16 Drawing Sheets

COX-2 Dimer Inserted into Membrane

Reagents and conditions a) Et$_3$N, EtOH, thiazolium, reflux 5 h. b) Toluene, TsOH, reflux 20 h. c) DMF, POCl$_3$. d) NaBH$_4$, EtOH. e) DEAD, PPh$_3$, RT 48 h. f) H$_2$, Pd/C, EtOH To generate acid groups:

| Protecting Group (PG) | Deprotection Conditions |
|---|---|
| 1) t-Bu | 1) 95% TFA, $CH_2Cl_2$ |
| 2) Me | 2) LiOH, $THF/H_2O$ |
| 3) Bn | 3) $H_2$, Pd/C |
| 4) Fm | 4) 20% Piperidine, DMF |

To generate amine groups:

| Protecting Group (PG) | Deprotection Conditions |
|---|---|
| 1) CPh$_3$ | 1) HCl, acetone |
| 2) Boc | 2) 95% TFA, CH$_2$Cl$_2$ |
| 3) CBZ | 3) H$_2$, Pd/C |
| 4) Fmoc | 4) 20% Piperidine, DMF |

Coupling via Amine Adapters and Biscarboxylic acids

Coupling
Conditions 1) i-Pr₂NEt, PyBOP, HOBT, DMF
2) DCC, DMAP, CH₂Cl₂
3) HATU, HOAT, i-Pr₂NEt, NMP Coupling via Carboxylate Adapters and Bisamines Coupling
Conditions 1) i-Pr₂NEt, PyBOP, HOBT, DMF
2) DCC, DMAP, CH₂Cl₂
3) HATU, HOAT, i-Pr₂NEt, NMP Reagents and conditions. a) DEAD, PPh$_3$, RT 48 h.
b) Deprotection conditions c) [(CH$_3$O)$_2$-B]$_2$, PdCl$_2$ Coupling via bisboronic acid linkers Coupling
Conditions Pd(PPh₃)₄, Na₂CO₃, H₂O, Toluene, Reflux Coupling via bis-aryliodide linkers Coupling Conditions
Pd(Ph₃P)₄, H₂O, EtOH, PhCH₃, reflux Coupling via alkyne linkers Coupling
Conditions $PdCl_2(PPh_3)_2$, CuI, $i-Pr_2NEt$, DMF Coupling via acrylate linkers Coupling
Conditions $PdCl_2(PPh_3)_2$, $Et_3N$, DMF

MULTIBINDING INHIBITORS OF CYCLOOXYGENASE-2

CROSS-REFERENCE TO RELATED APPLICATIONS

This application claims the benefit of U.S. Ser. No. 60/088,448, filed Jun. 8, 1998; U.S. Ser. No. 60/093,072, filed Jul. 16, 1998; and U.S. Ser. No. 60/120,281, filed Feb. 16, 1999, the disclosures of which are incorporated herein by reference in their entirety.

BACKGROUND OF THE INVENTION

1. Field of the Invention

This invention relates to novel multibinding compounds (agents) that inhibit the enzyme cyclooxygenase-2 (COX-2) and to pharmaceutical compositions comprising such compounds. Accordingly, the multibinding compounds and pharmaceutical compositions of this invention are useful in the treatment and prevention of various disorders mediated by COX-2, such as inflammation, pain, fever and the like.

2. References

The following publications are cited in this application as superscript numbers:

1 W. L. Smith et al., *Adv. Immunol.* 1996, 62, 167–215.
2 D. Picot et al., *Nature* 1994, 367, 243–249.
3 C. Luong et al., *Nat. Struct. Biol.* 1996, 3, 927–933.
4 R. G. Kurumbail et al., *Nature* 1996, 384, 644–688.
5 J. K. Gierse et al, *J. Biol. Chem.* 1996, 271, 15810–15814.
6 E. Wong et al., *J. Biol. Chem.* 1997, 272, 9280–9286.
7 P. Prasit et al., *Annual Reports in Medicinal Chemistry* 1997, 32, 211–220.
8 *J. Med. Chem.* 1997, 40, 1619–1633; 1634–1647.

All of the above publications are herein incorporated by reference in their entirety to the same extent as if each individual publication was specifically and individually indicated to be incorporated by reference in its entirety.

State of the Art

Cyclooxygenase (COX) catalyzes the conversion of arachidonic acid to prostaglandin H2, the first committed step in the biosynthesis of prostaglandins, such as prostacyclin and thromoxanes.[1] It has been known for some time that the enzyme COX is the target of certain non-steroidal anti-inflammatory drugs (NSAIDs), such as aspirin, ibuprofen, naproxen, indomethacin and the like. More recently, it has been discovered that there are two isoforms of COX, designated COX-1 and COX-2.

The COX-1 isozyme is constitutively expressed in many tissue types where it produces relatively small amounts of prostaglandins necessary for maintaining organ and tissue homeostasis. In constrast, COX-2 is transiently expressed in a limited number of cell types, including synovial cells, fibroblasts, macrophages and monocytes. In such cells, high level expression of COX-2 is rapidly induced in response to certain inflammatory agents, hormones, growth factors, cytokines and the like, resulting in various disorders such as inflammation, pain, fever and the like.

Unfortunately, most currently-marketed NSAIDs are typically equipotent inhibitors of both isozymes of COX. Since such drugs inhibit COX-1 as well as COX-2, they interfere with various prostaglandin-regulated processes not associated with the inflammation process and other related disorders. As a result, many NSAIDs cause severe side effects, such as stomach ulcers and renal damage, which limit their effectiveness as therapeutics. Accordingly, selective inhibitors of COX-2 would have significant advantages over currently-marketed NSAIDs.

It has now been discovered that selective COX-2 inhibitors having surprising and unexpected properties can be prepared by linking from 2 to 10 ligands to one or more linkers, wherein each ligand is a moiety capable of binding to COX-2. Such multibinding compounds provide improved biological and/or therapeutic effects compared to the aggregate of the unlinked ligands due to their multibinding properties.

SUMMARY OF THE INVENTION

This invention is directed to novel multibinding compounds (agents) that inhibit cyclooxygenase-2 (COX-2). The multibinding compounds of this invention are useful in the treatment and prevention of disorders mediated by COX-2, such as inflammation, pain, fever and the like.

Accordingly, in one of its composition aspects, this invention provides a multibinding compound comprising from 2 to 10 ligands covalently attached to one or more linkers wherein each of said ligands independently comprises a moiety capable of binding to cyclooxygenase-2; and pharmaceutically-acceptable salts thereof.

In another of its composition aspects, this invention provides a multibinding compound of formula I:

$$(L)_p(X)_q \qquad \qquad \text{I}$$

wherein each L is independently a ligand comprising a moiety capable of binding to cyclooxygenase-2; each X is independently a linker; p is an integer of from 2 to 10; and q is an integer of from 1 to 20; and pharmaceutically-acceptable salts thereof.

Preferably, q is less than p in the multibinding compounds of this invention.

Preferably, each ligand, L, in the multibinding compound of formula I is independently selected from a compound of formula IA, IB or IC:

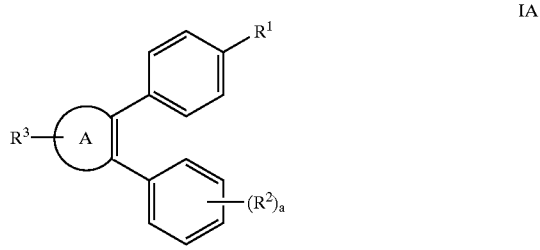

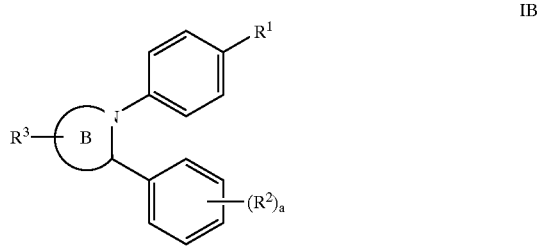

-continued

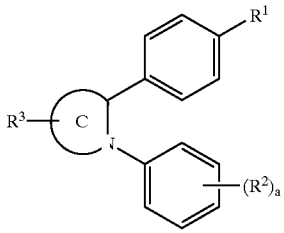

IC wherein
- ring A, together with the atoms to which it is attached, forms a 4, 5 or 6-membered carbocyclic or heterocyclic ring selected from the group consisting of aryl, cycloalkenyl, substituted cycloalkenyl, heteroaryl and heterocyclic;
- ring B, together with the atoms to which it is attached, forms a 4, 5 or 6-membered heterocyclic ring selected from the group consisting of heteroaryl and heterocyclic;
- ring C, together with the atoms to which it is attached, forms a 4, 5 or 6-membered heterocyclic ring selected from the group consisting of heteroaryl and heterocyclic;
- $R^1$ is selected from the group consisting of —SO$_2$CH$_3$, —SO$_2$NH$_2$, —SO$_2$NHC(O)CF$_3$, —SO(NH)NH$_2$ and —SO(NH)NHC(O)CF$_3$;
- each $R^2$ is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;
- $R^3$ is a covalent bond linking the ligand to a linker; and
- α is an integer from 0 to 3; and pharmaceutically-acceptable salts thereof.

Preferably, in the ligands of formula IA, ring A, together with the atoms to which it is attached, forms a cyclobut-2-en-1-one, thiazole, isothiazole, thiadiazole, oxazole, isoxazole, 5(H)-furanone, benzene, pyridine, imidazopyridine, imidazothiazole or thiazolotriazole ring.

In the ligands of formula IB, ring B, together with the atoms to which it is attached, preferably forms a pyrazole ring.

Preferably, in the ligands of formula IC, ring C, together with the atoms to which it is attached, forms an imidazole ring.

In still another of its composition aspects, this invention provides a multibinding compound of formula II:

$$L'-X'-L'$$   II wherein each L' is independently a ligand comprising a moiety capable of binding to cyclooxygenase-2 and X' is a linker; and pharmaceutically-acceptable salts thereof.

Preferably, in the multibinding compound of formula II, each ligand, L', is independently selected from the group consisting of:

(a) a compound of formula IIA:

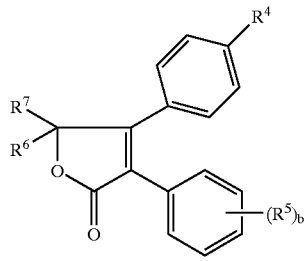

IIA wherein
- $R^4$ is selected from the group consisting of —SO$_2$CH$_3$, —SO$_2$NH$_2$, —SO$_2$NHC(O)CF$_3$, —SO(NH)NH$_2$ and —SO(NH)NHC(O)CF$_3$;
- each $R^5$ is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;
- $R^6$ is selected from the group consisting of hydrogen, alkyl, substituted alkyl, aryl, cyano, fluoro and heteroaryl;
- $R^7$ is a covalent bond linking the ligand to a linker; and
- b is an integer from 0 to 3;

(b) a compound of formula IIB:

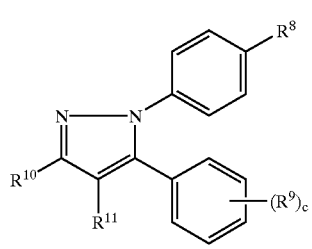

IIB wherein
- $R^8$ is selected from the group consisting of —SO$_2$CH$_3$, —SO$_2$NH$_2$, —SO$_2$NHC(O)CF$_3$, —SO(NH)NH$_2$ and —SO(NH)NHC(O)CF$_3$;
- each $R^9$ is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;
- $R^{10}$ is a covalent bond linking the ligand to a linker;
- $R^{11}$ is selected from the group consisting of hydrogen, alkyl, substituted alkyl and fluoro; and
- c is an integer from 0 to 3; and (c) a compound of formula IIC:

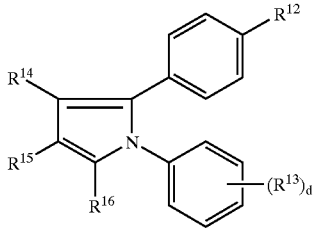

IIC wherein
$R^{12}$ is selected from the group consisting of —SO$_2$CH$_3$, —SO$_2$NH$_2$, —SO$_2$NHC(O)CF$_3$, —SO(NH)NH$_2$ and —SO(NH)NHC(O)CF$_3$;

each $R^{13}$ is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;

$R^{14}$ and $R^{16}$ are independently selected from the group consisting of hydrogen, alkyl, substituted alkyl and fluoro;

$R^{15}$ is a covalent bond linking the ligand to a linker; and d is an integer from 0 to 3;

and pharmaceutically-acceptable salts thereof.

In a preferred embodiment, this invention is also directed to a multibinding compound of formula III:

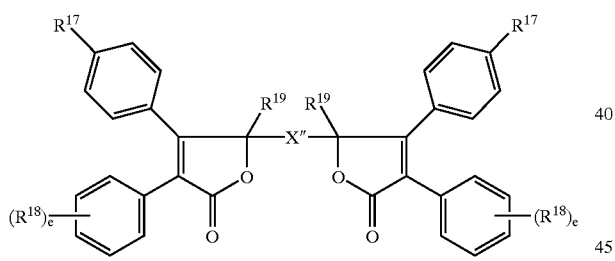

III wherein
each $R^{17}$ is independently selected from the group consisting of —SO$_2$CH$_3$, —SO$_2$NH$_2$, —SO$_2$NHC(O)CF$_3$, —SO(NH)NH$_2$ and —SO(NH)NHC(O)CF$_3$;

each $R^{18}$ is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;

each $R^{19}$ is selected from the group consisting of hydrogen, alkyl, substituted alkyl, aryl, cyano, fluoro and heteroaryl;

e is an integer from 0 to 3; and

X" is a linker; and pharmaceutically-acceptable salts thereof.

In another preferred embodiment, this invention is directed to a multibinding compound of formula IV:

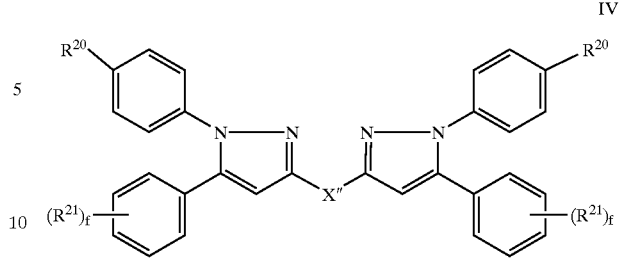

IV wherein
each $R^{20}$ is independently selected from the group consisting of —SO$_2$CH$_3$, —SO$_2$NH$_2$, —SO$_2$NHC(O)CF$_3$, —SO(NH)NH$_2$ and —SO(NH)NHC(O)CF$_3$;

each $R^{21}$ is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;

f is an integer from 0 to 3; and

X" is a linker; and pharmaceutically-acceptable salts thereof.

In still another preferred embodiment, this invention is directed to a multibinding compound of formula V:

V wherein
each $R^{22}$ is independently selected from the group consisting of —SO$_2$CH$_3$, —SO$_2$NH$_2$, —SO$_2$NHC(O)CF$_3$, —SO(NH)NH$_2$ and —SO(NH)NHC(O)CF$_3$;

each $R^{23}$ is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;

each $R^{24}$ is selected from the group consisting of hydrogen, alkyl, substituted alkyl, aryl, cyano, fluoro and heteroaryl;

g is an integer from 0 to 3; and

X" is a linker; and pharmaceutically-acceptable salts thereof.

Preferably, in the above embodiments, each linker (i.e., X, X' or X") independently has the formula:

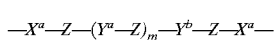

wherein
m is an integer of from 0 to 20;

$X^a$ at each separate occurrence is selected from the group consisting of —O—, —S—, —NR—, —C(O)—, —C(O)O—, —C(O)NR—, —C(S), —C(S)O—, —C(S)NR— or a covalent bond where R is as defined below;

Z is at each separate occurrence is selected from the group consisting of alkylene, substituted alkylene, cycloalkylene, substituted cycloalkylene, alkenylene, substituted alkenylene, alkynylene, substituted alkynylene, cycloalkenylene, substituted cycloalkenylene, arylene, heteroarylene, heterocyclene, or a covalent bond;

$Y^a$ and $Y^b$ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —N=C($X^a$)—NR'—, —P(O)(OR')—O—, —S(O)$_n$CR'R"—, —S(O)$_n$—NR'—, —S—S— and a covalent bond; where n is 0, 1 or 2; and R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic.

In yet another of its composition aspects, this invention provides a pharmaceutical composition comprising a pharmaceutically acceptable carrier and an effective amount of a multibinding compound comprising from 2 to 10 ligands covalently attached to one or more linkers wherein each of said ligands independently comprises a moiety capable of binding to cyclooxygenase-2; and pharmaceutically-acceptable salts thereof.

This invention is also directed to pharmaceutical compositions comprising a pharmaceutically acceptable carrier and an effective amount of a multibinding compound of formula I, II, III, IV or V.

The multibinding compounds of this invention are effective inhibitors of the enzyme cyclooxygenase-2 (COX-2), an enzyme involved in the biosynthesis of prostaglandins associated with inflammation. Accordingly, in one of its method aspects, this invention provides a method for treating inflammation or an inflammation-related disorder in a patient, the method comprising administering to a patient having inflammation or an inflammation-related disorder a pharmaceutical composition comprising a pharmaceutically-acceptable carrier and a therapeutically-effective amount of a multibinding compound comprising from 2 to 10 ligands covalently attached to one or more linkers wherein each of said ligands independently comprises a moiety capable of binding to cyclooxygenase-2; and pharmaceutically-acceptable salts thereof.

This invention is also directed to general synthetic methods for generating large libraries of diverse multimeric compounds which multimeric compounds are candidates for possessing multibinding properties for cyclooxygenase-2. The diverse multimeric compound libraries provided by this invention are synthesized by combining a library of linkers with a library of ligands each having complementary functional groups permitting covalent linkage. The library of linkers is preferably selected to have diverse properties such as valency, linker length, linker geometry and rigidity, hydrophilicity or hydrophobicity, amphiphilicity, acidity, basicity and polarization. The library of ligands is preferably selected to have diverse attachment points on the same ligand, different functional groups at the same site of otherwise the same ligand, and the like.

Additionally, this invention is directed to libraries of diverse multimeric compounds which multimeric compounds are candidates for possessing multibinding properties for cyclooxygenase-2. These libraries are prepared via the methods described above and permit the rapid and efficient evaluation of what molecular constraints impart multibinding properties to a ligand or a class of ligands for cyclooxygenase-2.

Accordingly, in one of its method aspects, this invention is directed to a method for identifying multimeric ligand compounds possessing multibinding properties for cyclooxygenase-2, which method comprises:

(a) identifying a ligand or a mixture of ligands wherein each ligand contains at least one reactive functionality;

(b) identifying a library of linkers wherein each linker in said library comprises at least two functional groups having complementary reactivity to at least one of the reactive functional groups of the ligand;

(c) preparing a multimeric ligand compound library by combining at least two stoichiometric equivalents of the ligand or mixture of ligands identified in (a) with the library of linkers identified in (b) under conditions wherein the complementary functional groups react to form a covalent linkage between said linker and at least two of said ligands; and (d) assaying the multimeric ligand compounds produced in the library prepared in (c) above to identify multimeric ligand compounds possessing multibinding properties for cyclooxygenase-2.

In another of its method aspects, this invention is directed to a method for identifying multimeric ligand compounds possessing multibinding properties for cyclooxygenase-2, which method comprises:

(a) identifying a library of ligands wherein each ligand contains at least one reactive functionality;

(b) identifying a linker or mixture of linkers wherein each linker comprises at least two functional groups having complementary reactivity to at least one of the reactive functional groups of the ligand;

(c) preparing a multimeric ligand compound library by combining at least two stoichiometric equivalents of the library of ligands identified in (a) with the linker or mixture of linkers identified in (b) under conditions wherein the complementary functional groups react to form a covalent linkage between said linker and at least two of said ligands; and (d) assaying the multimeric ligand compounds produced in the library prepared in (c) above to identify multimeric ligand compounds possessing multibinding properties for cyclooxygenase-2.

Preferably, in these methods, the preparation of the multimeric ligand compound library is achieved by either the sequential or concurrent combination of the two or more stoichiometric equivalents of the ligands identified in (a) with the linkers identified in (b).

Additionally, the multimeric ligand compounds comprising the multimeric ligand compound library are preferably dimeric. In one embodiment, the dimeric ligand compounds comprising the dimeric ligand compound library are heterodimeric. The heterodimeric ligand compound library is preferably prepared by sequential addition of a first and second ligand.

In a preferably embodiment of the above methods, prior to procedure (d), each member of the multimeric ligand compound library is isolated from the library. More preferably, each member of the library is isolated by preparative liquid chromatography mass spectrometry (LCMS).

In the above methods, the linker or linkers employed are preferably selected from the group comprising flexible linkers, rigid linkers, hydrophobic linkers, hydrophilic linkers, linkers of different geometry, acidic linkers, basic linkers, linkers of different polarization and/or polarizability and amphiphilic linkers. More preferably, the linkers comprise linkers of different chain length and/or having different complementary reactive groups. Still more preferably, the linkers are selected to have different linker lengths ranging from about 2 to 100 Å.

The ligand or mixture of ligands employed in the above methods is preferably selected to have reactive functionality at different sites on said ligands. More preferably, the reactive functionality is selected from the group consisting of carboxylic acids, carboxylic acid halides, carboxyl esters, amines, halides, pseudohalides, isocyanates, vinyl unsaturation, ketones, aldehydes, thiols, alcohols, anhydrides, boronates, and precursors thereof wherein the reactive functionality on the ligand is selected to be complementary to at least one of the reactive groups on the linker so that a covalent linkage can be formed between the linker and the ligand.

In one preferred embodiment of the above methods, the multimeric ligand compound library comprises homomeric ligand compounds. In another preferred embodiment, the multimeric ligand compound library comprises heteromeric ligand compounds.

In one of its composition aspects, this invention is directed to a library of multimeric ligand compounds which may possess multivalent properties. for cyclooxygenase-2, which library is prepared by the method comprising:
  (a) identifying a ligand or a mixture of ligands wherein each ligand contains at least one reactive functionality;
  (b) identifying a library of linkers wherein each linker in said library comprises at least two functional groups having complementary reactivity to at least one of the reactive functional groups of the ligand; and
  (c) preparing a multimeric ligand compound library by combining at least two stoichiometric equivalents of the ligand or mixture of ligands identified in (a) with the library of linkers identified in (b) under conditions wherein the complementary functional groups react to form a covalent linkage between said linker and at least two of said ligands.

In another of its composition aspects, this invention is directed to a library of multimeric ligand compounds which may possess multivalent properties for cyclooxygenase-2, which library is prepared by the method comprising:
  (a) identifying a library of ligands wherein each ligand contains at least one reactive functionality;
  (b) identifying a linker or mixture of linkers wherein each linker comprises at least two functional groups having complementary reactivity to at least one of the reactive functional groups of the ligand; and
  (c) preparing a multimeric ligand compound library by combining at least two stoichiometric equivalents of the library of ligands identified in (a) with the linker or mixture of linkers identified in (b) under conditions wherein the complementary functional groups react to form a covalent linkage between said linker and at least two of said ligands.

In a preferred embodiment, the linker or linkers employed are preferably selected from the group comprising flexible linkers, rigid linkers, hydrophobic linkers, hydrophilic linkers, linkers of different geometry, acidic linkers, basic linkers, linkers of different polarization and/or polarizability and amphiphilic linkers. More preferably, the linkers comprise linkers of different chain length and/or having different complementary reactive groups. Still more preferably, the linkers are selected to have different linker lengths ranging from about 2 to 100 Å.

In the above libraries, the ligand or mixture of ligands is preferably selected to have reactive functionality at different sites on said ligands. Preferably, the reactive functionality is selected from the group consisting of carboxylic acids, carboxylic acid halides, carboxyl esters, amines, halides, pseudohalides, isocyanates, vinyl unsaturation, ketones, aldehydes, thiols, alcohols, anhydrides, boronates, and precursors thereof wherein the reactive functionality on the ligand is selected to be complementary to at least one of the reactive groups on the linker so that a covalent linkage can be formed between the linker and the ligand.

In one embodiment, the multimeric ligand compound library comprises homomeric ligand compounds (i.e., each of the ligands is the same, although it may be attached at different points). In another embodiment, the multimeric ligand compound library comprises heteromeric ligand compounds (i.e., at least one of the ligands is different from the other ligands).

In another of its method aspects, this invention is directed to an iterative method for identifying multimeric ligand compounds possessing multibinding properties for cyclooxygenase-2, which method comprises:
  (a) preparing a first collection or iteration of multimeric compounds which is prepared by contacting at least two stoichiometric equivalents of the ligand or mixture of ligands which target a receptor with a linker or mixture of linkers wherein said ligand or mixture of ligands comprises at least one reactive functionality and said linker or mixture of linkers comprises at least two functional groups having complementary reactivity to at least one of the reactive functional groups of the ligand wherein said contacting is conducted under conditions wherein the complementary functional groups react to form a covalent linkage between said linker and at least two of said ligands;
  (b) assaying said first collection or iteration of multimeric compounds to assess which if any of said multimeric compounds possess multibinding properties for cyclooxygenase-2;
  (c) repeating the process of (a) and (b) above until at least one multimeric compound is found to possess multibinding properties for cyclooxygenase-2;
  (d) evaluating what molecular constraints imparted or are consistent with imparting multibinding properties to the multimeric compound or compounds found in the first iteration recited in (a)–(c) above;
  (e) creating a second collection or iteration of multimeric compounds which elaborates upon the particular molecular constraints imparting multibinding properties to the multimeric compound or compounds found in said first iteration;
  (f) evaluating what molecular constraints imparted or are consistent with imparting enhanced multibinding properties to the multimeric compound or compounds found in the second collection or iteration recited in (e) above;
  (g) optionally repeating steps (e) and (f) to further elaborate upon said molecular constraints.

Preferably, steps (e) and (f) are repeated from 2–50 times. More preferably, steps (e) and (f) are repeated from 5–50 times.

Preferably, the ligands employed in the above methods and library compositions are selected from ligands of formula IA-IC, more preferably, from ligands of formula IIA–IIC.

DETAILED DESCRIPTION OF THE INVENTION

Figure 1A:
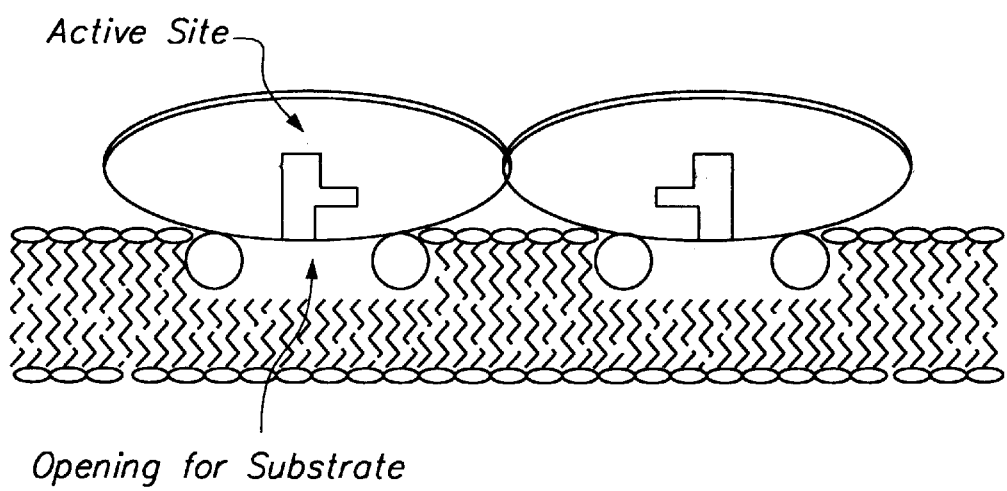
FIG. 1A illustrates a COX-2 dimer inserted into a membrane.
Figure 1B:
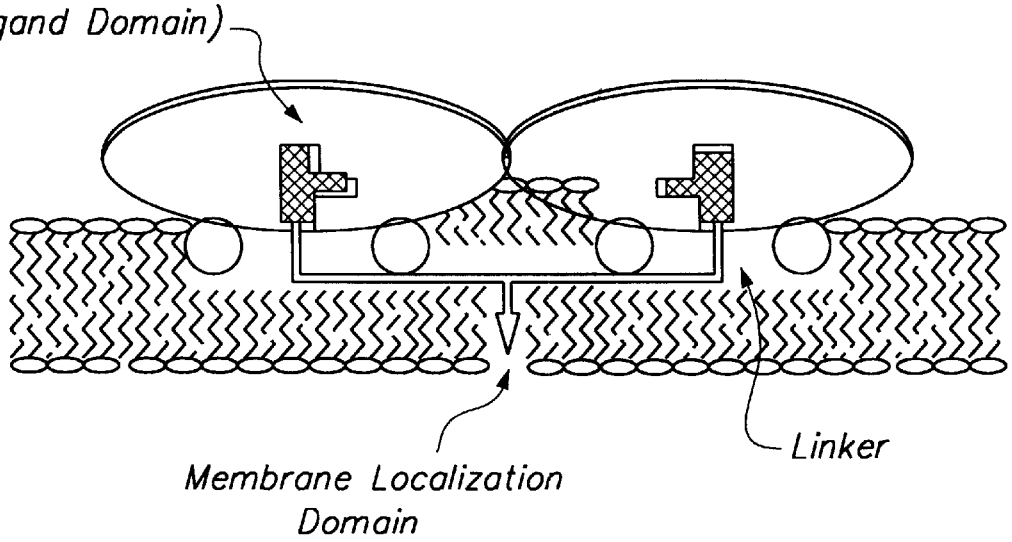
FIG. 1B illustrates a dimeric membrane-anchored COX-2 selective inhibitor.

This invention is directed to multibinding compounds which inhibit the enzyme cyclooxygenase-2, pharmaceutical compositions containing such compounds and methods for treating inflammation or an inflammation-related disorder. When discussing such compounds, compositions or methods, the following terms have the following meanings unless otherwise indicated. Any undefined terms have their art recognized meanings.

The term "alkyl" refers to a monoradical branched or unbranched saturated hydrocarbon chain preferably having from 1 to 40 carbon atoms, more preferably 1 to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkylene" refers to a diradical of a branched or unbranched saturated hydrocarbon chain, preferably having from 1 to 40 carbon atoms, more preferably 1 to 10 carbon atoms and even more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to an alkylene group, as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures.

The term "alkaryl" refers to the groups -alkylene-aryl and -substituted alkylene-aryl where alkylene, substituted alkylene and aryl are defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkylalkoxy" refers to the groups -alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Preferred alkylalkoxy groups are alkylene-O-alkyl and include, by way of example, methylenemethoxy (—CH$_2$CH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$) and the like.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkenylene" refers to a diradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. This term is exemplified by groups such as ethenylene (—CH=CH—), the propenylene isomers (e.g., —CH$_2$CH=CH— and —C(CH$_3$)=CH—) and the like.

The term "substituted alkenylene" refers to an alkenylene group as defined above having from 1 to 5 substituents, and preferably from 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

The term "alkynyl" refers to a monoradical of an unsaturated hydrocarbon preferably having from 2 to 40 carbon atoms, more preferably 2 to 20 carbon atoms and even more preferably 2 to 6 carbon atoms and having at least 1 and preferably from 1–6 sites of acetylene (triple bond) unsaturation. Preferred alkynyl groups include ethynyl (—C≡CH), propargyl (—CH$_2$C≡CH) and the like.

The term "substituted alkynyl" refers to an alkynyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkynylene" refers to a diradical of an unsaturated hydrocarbon preferably having from 2 to 40 carbon atoms, more preferably 2 to 10 carbon atoms and even more preferably 2 to 6 carbon atoms and having at least 1 and preferably from 1–6 sites of acetylene (triple bond) unsaturation. Preferred alkynylene groups include ethynylene (—C≡C—), propargylene (—CH$_2$C≡—C—) and the like.

The term "substituted alkynylene" refers to an alkynylene group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that both R's are not hydrogen.

The term "carboxyalkyl" or "alkoxycarbonyl" refers to the groups "—C(O)O-alkyl", "—C(O)O-substituted alkyl", "—C(O)O-cycloalkyl", "—C(O)O-substituted cycloalkyl", "—C(O)O-alkenyl", "—C(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cycloocт-3-enyl and the like.

The term "substituted cycloalkenyl" refers to cycloalkenyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl and trihalomethyl. Preferred aryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

The term "halo" or "halogen" refers to fluoro, chloro, bromo and iodo.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "heteroaryloxy" refers to the group heteroaryl-O—.

The term "heteroarylene" refers to the diradical group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridnylene, 2,5-indolenyl and the like.

The term "heterocycle" or "heterocyclic" refers to a monoradical saturated unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "heterocyclooxy" refers to the group heterocyclic-O—.

The term "thioheterocyclooxy" refers to the group heterocyclic-S—.

The term "heterocyclene" refers to the diradical group formed from a heterocycle, as defined herein, and is exemplified by the groups 2,6-morpholino, 2,5-morpholino and the like.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "spiro-attached cycloalkyl group" refers to a cycloalkyl group attached to another ring via one carbon atom common to both rings.

The term "thiol" refers to the group —SH.

The term "thioalkoxy" refers to the group —S-alkyl.

The term "substituted thioalkoxy" refers to the group —S-substituted alkyl.

The term "ethioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

The term "pharmaceutically-acceptable salt" refers to salts which retain the biological effectiveness and properties of the multibinding compounds of this invention and which are not biologically or otherwise undesirable. In many cases, the multibinding compounds of this invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "pharmaceutically-acceptable cation" refers to the cation of a pharmaceutically-acceptable salt.

The term "protecting group" or "blocking group" refers to any group which when bound to one or more hydroxyl, thiol, amino or carboxyl groups of the compounds (including intermediates thereof) prevents reactions from occurring at these groups and which protecting group can be removed by conventional chemical or enzymatic steps to reestablish the hydroxyl, thiol, amino or carboxyl group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product.

Preferred removable thiol blocking groups include disulfide groups, acyl groups, benzyl groups, and the like.

Preferred removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC), and the like which can be removed by conventional conditions compatible with the nature of the product.

Preferred carboxyl protecting groups include esters such as methyl, ethyl, propyl, t-butyl etc. which can be removed by mild conditions compatible with the nature of the product.

The term "optional" or "optionally" means that the subsequently described event, circumstance or substituent may or may not occur, and that the description includes instances where said event or circumstance occurs and instances where it does not.

The term "ligand" as used herein denotes a moiety or compound that is capable of binding to the enzyme cyclooxygenase-2. The specific region or regions of the ligand that is (are) recognized by the enzyme is designated as the "ligand domain". A ligand may be either capable of binding to an enzyme by itself, or may require the presence of one or more non-ligand components for binding (e.g., $Ca^{+2}$, $Mg^{+2}$ or a water molecule is required for the binding of a ligand to various ligand binding sites).

Examples of ligands useful in this invention are described herein. Those skilled in the art will appreciate that portions of the ligand structure that are not essential for specific molecular recognition and binding activity may be varied substantially, replaced or substituted with unrelated structures (for example, with ancillary groups as defined below) and, in some cases, omitted entirely without affecting the binding interaction. The primary requirement for a ligand is that it has a ligand domain as defined above. It is understood that the term ligand is not intended to be limited to compounds known to be useful in binding to cyclooxygenase-2 (e.g., known drugs). Those skilled in the art will understand that the term ligand can equally apply to a molecule that is not normally associated with enzyme binding properties. In addition, it should be noted that ligands that exhibit marginal activity or lack useful activity as monomers can be highly active as multivalent compounds because of the benefits conferred by multivalency.

The term "multibinding compound or agent" refers to a compound that is capable of multivalency, as defined below, and which has 2–10 ligands covalently bound to one or more linkers which may be the same or different. Multibinding compounds provide a biological and/or therapeutic effect greater than the aggregate of unlinked ligands equivalent thereto which are made available for binding. That is to say that the biological and/or therapeutic effect of the ligands attached to the multibinding compound is greater than that achieved by the same amount of unlinked ligands made available for binding to the ligand binding sites (receptors). The phrase "increased biological or therapeutic effect" includes, for example: increased affinity, increased selectivity for target, increased specificity for target, increased potency, increased efficacy, decreased toxicity, improved duration of activity or action, decreased side effects, increased therapeutic index, improved bioavailibity, improved pharmacokinetics, improved activity spectrum, and the like. The multibinding compounds of this invention will exhibit at least one and preferably more than one of the above-mentioned affects.

The term "mulimeric compound" refers to a compound containing 2 to 10 ligands covalently connected through at least one linker which compound may or may not possess multibinding properties.

The term "potency" refers to the minimum concentration at which a ligand is able to achieve a desirable biological or therapeutic effect. The potency of a ligand is typically proportional to its affinity for its ligand binding site. In some cases, the potency may be non-linearly correlated with its affinity. In comparing the potency of two drugs, e.g., a multibinding agent and the aggregate of its unlinked ligand, the dose-response curve of each is determined under identical test conditions (e.g., in an in vitro or in vivo assay, in an appropriate animal model). The finding that the multbinding agent produces an equivalent biological or therapeutic effect at a lower concentration than the aggregate unlinked ligand is indicative of enhanced potency.

The term "univalency" as used herein refers to a single binding interaction between one ligand as defined herein with one ligand binding site as defined herein. It should be noted that a compound having multiple copies of a ligand (or ligands) exhibit univalency when only one ligand is interacting with a ligand binding site. Examples of univalent interactions are depicted below.

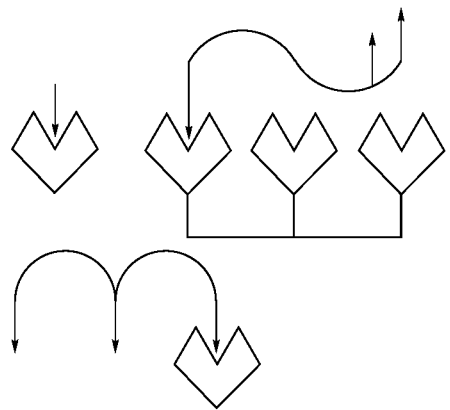

The term "multivalency" as used herein refers to the concurrent binding of from 2 to 10 linked ligands (which may be the same or different) and two or more corresponding receptors (ligand binding sites) on one or more enzymes which may be the same or different.

For example, two ligands connected through a linker that bind concurrently to two ligand binding sites would be considered as bivalency; three ligands thus connected would be an example of trivalency. An example of trivalent binding, illustrating a multibinding compound bearing three ligands versus a monovalent binding interaction, is shown below:

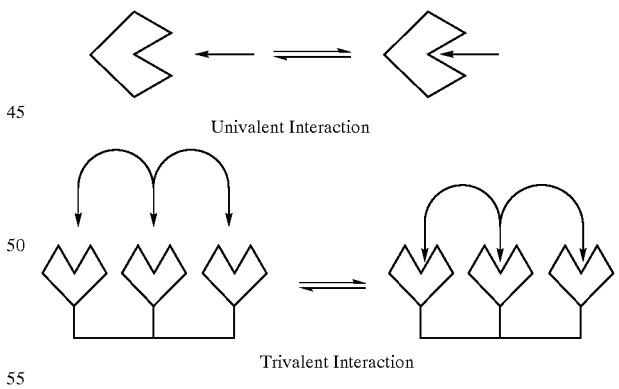

Univalent Interaction

Trivalent Interaction

It should be understood that all compounds that contain multiple copies of a ligand attached to a linker or to linkers do not necessarily exhibit the phenomena of multivalency, i.e., that the biological and/or therapeutic effect of the multibinding agent is greater than the sum of the aggregate of unlinked ligands made available for binding to the ligand binding site (receptor). For multivalency to occur, the ligands that are connected by a linker or linkers have to be presented to their ligand binding sites by the linker(s) in a specific manner in order to bring about the desired ligand-orienting result, and thus produce a multibinding event.

The term "selectivity" or "specificity" is a measure of the binding preferences of a ligand for different ligand binding sites (receptors). The selectivity of a ligand with respect to its target ligand binding site relative to another ligand binding site is given by the ratio of the respective values of $K_d$ (i.e., the dissociation constants for each ligand-receptor complex) or, in cases where a biological effect is observed below the $K_d$, the ratio of the respective $EC_{50}$'s (i.e., the concentrations that produce 50% of the maximum response for the ligand interacting with the two distinct ligand binding sites (receptors)).

The term "ligand binding site" denotes the site on the cyclooxygenase-2 enzyme that recognizes a ligand domain and provides a binding partner for the ligand. The ligand binding site may be defined by monomeric or multimeric structures. This interaction may be capable of producing a unique biological effect, for example, agonism, antagonism, modulatory effects, may maintain an ongoing biological event, and the like.

The terms "agonism" and "antagonism" are well known in the art. The term "modulatory effect" refers to the ability of the ligand to change the activity of an agonist or antagonist through binding to a ligand binding site.

It should be recognized that the ligand binding sites of the enzyme that participate in biological multivalent binding interactions are constrained to varying degrees by their intra- and inter-molecular associations (e.g., such macromolecular structures may be covalently joined to a single structure, noncovalently associated in a multimeric structure, embedded in a membrane or polymeric matrix, and so on) and therefore have less translational and rotational freedom than if the same structures were present as monomers in solution.

The term "inert organic solvent" or "inert solvent" means a solvent which is inert under the conditions of the reaction being described in conjunction therewith including, by way of example only, benzene, toluene, acetonitrile, tetrahydrofuran, dimethylformamide, chloroform, methylene chloride, diethyl ether, ethyl acetate, acetone, methylethyl ketone, methanol, ethanol, propanol, isopropanol, t-butanol, dioxane, pyridine, and the like. Unless specified to the contrary, the solvents used in the reactions described herein are inert solvents.

The term "treatment" refers to any treatment of a pathologic condition in a mammal, particularly a human, and includes:

(i) preventing the pathologic condition from occurring in a subject which may be predisposed to the condition but has not yet been diagnosed with the condition and, accordingly, the treatment constitutes prophylactic treatment for the disease condition;

(ii) inhibiting the pathologic condition, i.e., arresting its development;

(iii) relieving the pathologic condition, i.e., causing regression of the pathologic condition; or (iv) relieving the conditions mediated by the pathologic condition.

The term "pathologic condition which is modulated by treatment with a ligand" covers all disease states (i.e., pathologic conditions) which are generally acknowledged in the art to be usefully treated with a ligand for the enzyme cyclooygenase-2 in general, and those disease states which have been found to be usefully treated by a specific multibinding compound of our invention. Such disease states include, by way of example only, the treatment of a mammal afflicted with inflammation, pain, fever and the like.

The term "therapeutically effective amount" refers to that amount of multibinding compound which is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "linker", identified where appropriate by the symbol X, X' or X", refers to a group or groups that covalently links from 2 to 10 ligands (as identified above) in a manner that provides for a compound capable of multivalency. Each linker may be chiral or achiral. Among other features, the linker is a ligand-orienting entity that permits attachment of multiple copies of a ligand (which may be the same or different) thereto. In some cases, the linker may itself be biologically active. The term "linker" does not, however, extend to cover solid inert supports such as beads, glass particles, fibers, and the like. But it is understood that the multibinding compounds of this invention can be attached to a solid support if desired. For example, such attachment to solid supports can be made for use in separation and purification processes and similar applications.

The extent to which multivalent binding is realized depends upon the efficiency with which the linker or linkers that joins the ligands presents these ligands to the array of available ligand binding sites. Beyond presenting these ligands for multivalent interactions with ligand binding sites, the linker or linkers spatially constrains these interactions to occur within dimensions defined by the linker or linkers. Thus, the structural features of the linker (valency, geometry, orientation, size, flexibility, chemical composition, etc.) are features of multibinding agents that play an important role in determining their activities.

The linkers used in this invention are selected to allow multivalent binding of ligands to the ligand binding sites of cyclooxygenase-2, whether such sites are located interiorly, both interiorly and on the periphery of the enzyme structure, or at any intermediate position thereof. Crystal structures of COX-1 and COX-2 with bound inhibitors are known.[2,3,4] FIG. 1A illustrates a COX-2 dimer inserted into a membrane. While not intending to be limited by theory, it is believed that both isozymes are membrane-bound homodimers localized to the lumenal side of the ER membrane. In each, the monomer subunit consists of three substructures, an EGF-like domain, a catalytic domain, and a membrane-binding domain. The membrane-binding domain consists of four amphipathic helices arranged in a box-like structure around the mouth of the active site. The active site itself is a long, deep cavity extending vertically from the plane of the membrane (defined by the hydrophobic faces of the four helices in the membrane binding domain), roughly 8×25 angstroms in size. There is a single biochemically and structurally distinct active site in each monomer, representing parallel channels perpendicular to the membrane and spaced roughly 40 angstroms apart. Accordingly, in the present invention, the distance between the nearest neighboring ligand domains is preferably greater than about 10 Å, more preferably in the range of about 40 Å to about 100 Å.

It is also known that there are subtle but important differences between the active sites of COX-1 and COX-2. Calculations of solvent-accessible surface area reveal that while the COX-1 active site has a relatively straight and cylindrical shape, that of COX-2 possesses a side pocket extending from the main cylinder.[3] This pocket is created by an Ile to Val mutation, opening a channel parallel to the membrane and leading to a net increase of 25% in the total volume of the active site. Mutation of this residue in COX-1 confers COX-2 selectivity for one class of NSAIDs, providing biochemical confirmation of the significance of this structural observation.[5,6]

Another critical observation in the COX-2 crystal structure concerns the binding mode of NSAID inhibitors. In the structure of flurbiprofen-inhibited COX-1, the inhibitor is observed to be totally enclosed within the protein, exposing less than 4% of its total surface area to bulk solvent.[2] In the structure of COX-2 with a selective inhibitor, a portion of the inhibitor is clearly protruding from the mouth of the active site, pointing into the region occupied by the membrane. A structure of COX-2 with a different NSAID shows the active site mouth shut, comparable to the COX-1/flurbiprofen structure. Together, these structures suggest considerable flexibility in the mouth of the COX-2 active site and show that at least one class of inhibitors can bind with portions of the molecule protruding into the membrane.[3]

The ligands are covalently attached to the linker or linkers using conventional chemical techniques providing for covalent linkage of the ligand to the linker or linkers. Reaction chemistries resulting in such linkages are well known in the art and involve the use of complementary functional groups on the linker and ligand. Preferably, the complementary functional groups on the linker are selected relative to the functional groups available on the ligand for bonding or which can be introduced onto the ligand for bonding. Again, such complementary functional groups are well known in the art. For example, reaction between a carboxylic acid of either the linker or the ligand and a primary or secondary amine of the ligand or the linker in the presence of suitable, well-known activating agents results in formation of an amide bond covalently linking the ligand to the linker; reaction between an amine group of either the linker or the ligand and a sulfonyl halide of the ligand or the linker results in formation of a sulfonamide bond covalently linking the ligand to the linker; and reaction between an alcohol or phenol group of either the linker or the ligand and an alkyl or aryl halide of the ligand or the linker results in formation of an ether bond covalently linking the ligand to the linker.

Table I below illustrates numerous complementary reactive groups and the resulting bonds formed by reaction there between.

TABLE I

Representative Complementary Binding Chemistries

| First Reactive Group | Second Reactive Group | Linkage |
|---|---|---|
| hydroxyl | isocyanate | urethane |
| amine | epoxide | β-hydroxyamine |
| sulfonyl halide | amine | sulfonamide |
| carboxyl | amine | amide |
| hydroxyl | alkyl/aryl halide | ether |

The linker is attached to the ligand at a position that retains ligand domain-ligand binding site interaction and specifically which permits the ligand domain of the ligand to orient itself to bind to the ligand binding site. Such positions and synthetic protocols for linkage are well known in the art. The term linker embraces everything that is not considered to be part of the ligand.

The relative orientation in which the ligand domains are displayed derives from the particular point or points of attachment of the ligands to the linker, and on the framework geometry. The determination of where acceptable substitutions can be made on a ligand is typically based on prior knowledge of structure-activity relationships (SAR) of the ligand and/or congeners and/or structural information about ligand-receptor complexes (e.g., X-ray crystallography, NMR, and the like). Such positions and the synthetic methods for covalent attachment are well known in the art. Following attachment to the selected linker (or attachment to a significant portion of the linker, for example 2–10 atoms of the linker), the univalent linker-ligand conjugate may be tested for retention of activity in the relevant assay.

Suitable linkers are discussed more fully below.

At present, it is preferred that the multibinding agent is a bivalent compound, e.g., two ligands which are covalently linked to linker X.

The term "library" refers to at least 3, preferably from $10^2$ to $10^9$ and more preferably from $10^2$ to $10^4$ multimeric compounds. Preferably, these compounds are prepared as a multiplicity of compounds in a single solution or reaction mixture which permits the facile synthesis thereof. In one embodiment, the library of multimeric compounds can be directly assayed for multibinding properties. In another embodiment, each member of the library of multimeric compounds is first isolated and, optionally, characterized. This member is then assayed for multibinding properties.

The term "collection" refers to a set of multimeric compounds which are prepared either sequentially or concurrently (e.g., combinatorially). The collection comprises at least 2 members; preferably from 2 to $10^9$ members and still more preferably from 10 to $10^4$ members.

The term "pseudohalide" refers to a functional group which react in a displacement reaction in a manner similar to a halogen, e.g., functions as a leaving group is a displacement reaction. Such functional groups include, by way of example, mesyl, tosyl, azido, cyano and the like.

Methodology

The linker, when covalently attached to multiple copies of the ligands, provides a biocompatible, substantially non-immunogenic multibinding compound. The biological activity of the multibinding compound is highly sensitive to the valency, geometry, composition, size, flexibility or rigidity, etc. of the linker and, in turn, on the overall structure of the multibinding compound, as well as the presence or absence of anionic or cationic charge, the relative hydrophobicity/hydrophilicity of the linker, and the like on the linker. Accordingly, the linker is preferably chosen to maximize the biological activity of the multibinding compound. The linker may be chosen to enhance the biological activity of the molecule. In general, the linker may be chosen from any organic molecule construct that orients two or more ligands to their ligand binding sites to permit multivalency. In this regard, the linker can be considered as a "framework" on which the ligands are arranged in order to bring about the desired ligand-orienting result, and thus produce a multibinding compound.

For example, different orientations can be achieved by including in the framework groups containing mono- or polycyclic groups, including aryl and/or heteroaryl groups, or structures incorporating one or more carbon-carbon multiple bonds (alkenyl, alkenylene, alkynyl or alkynylene groups). Other groups can also include oligomers and polymers which are branched- or straight-chain species. In preferred embodiments, rigidity is imparted by the presence of cyclic groups (e.g., aryl, heteroaryl, cycloalkyl, heterocyclic, etc.). In other preferred embodiments, the ring is a six or ten member ring. In still further preferred embodiments, the ring is an aromatic ring such as, for example, phenyl or naphthyl.

Different hydrophobic/hydrophilic characteristics of the linker as well as the presence or absence of charged moieties can readily be controlled by the skilled artisan. For example, the hydrophobic nature of a linker derived from hexamethylene diamine ($H_2N(CH_2)_6NH_2$) or related polyamines can be modified to be substantially more hydrophilic by replacing the alkylene group with a poly(oxyalkylene) group such as found in the commercially available "Jeffamines".

The intersection of the framework (linker) and the ligand group, and indeed, the framework (linker) itself can have many different bonding patterns. Examples of acceptable patterns of three contiguous atom arrangements are shown in the following diagram:

| CCC | NCC | OCC | SCC | PCC |
|-----|-----|-----|-----|-----|
| CCN | NCN | OCN | SCN | PCN |
| CCO | NCO | OCO | SCO | PCO |
| CCS | NCS | OCS | SCS | PCS |
| CCP | NCP | OCP | SCP | PCP |
| CNC | NNC | ONC | SNC | PNC |
| CNN | NNN | ONN | SNN | PNN |
| CNO | NNO | ONO | SNO | PNO |
| CNS | NNS | ONS | SNS | PNS |
| CNP | NNP | ONP | SNP | PNP |
| COC | NOC | OOC | SOC | POC |
| CON | NON | OON | SON | PON |
| COO | NOO | OOO | SOO | POO |
| COS | NOS | OOS | SOS | POS |
| COP | NOP | OOP | SOP | POP |
| CSC | NSC | OSC | SSC | PSC |
| CSN | NSN | OSN | SSN | PSN |
| CSO | NSO | OSO | SSO | PSO |
| CSS | NSS | OSS | SSS | PSS |
| CSP | NSP | OSP | SSP | PSP |
| CPC | NPC | OPC | SPC | PPC |
| CPN | NPN | OPN | SPN | PPN |
| CPO | NPO | OPO | SPO | PPO |
| CPS | NPS | OPS | SPS | PPS |
| CPP | NPP | OPP | SPP | PPP |

One skilled in the art would be able to identify bonding patterns that would produce multivalent compounds. Methods for producing these bonding arrangements are described in March, "Advanced Organic Chemistry", 4th Edition, Wiley-Interscience, New York, N.Y. (1992). These arrangements are described in the grid of dots shown in the scheme above. All of the possible arrangements for the five most preferred atoms are shown. Each atom has a variety of acceptable oxidation states. The bonding arrangements underlined are less acceptable and are not preferred.

Examples of molecular structures in which the above bonding patterns could be employed as components of the linker are shown below.

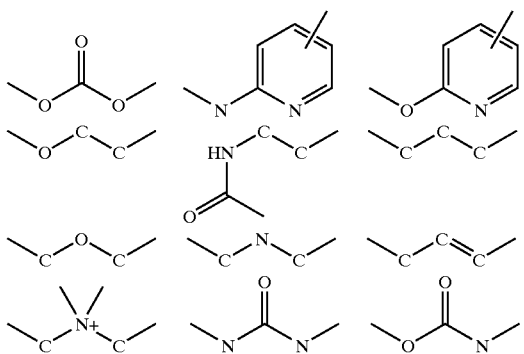

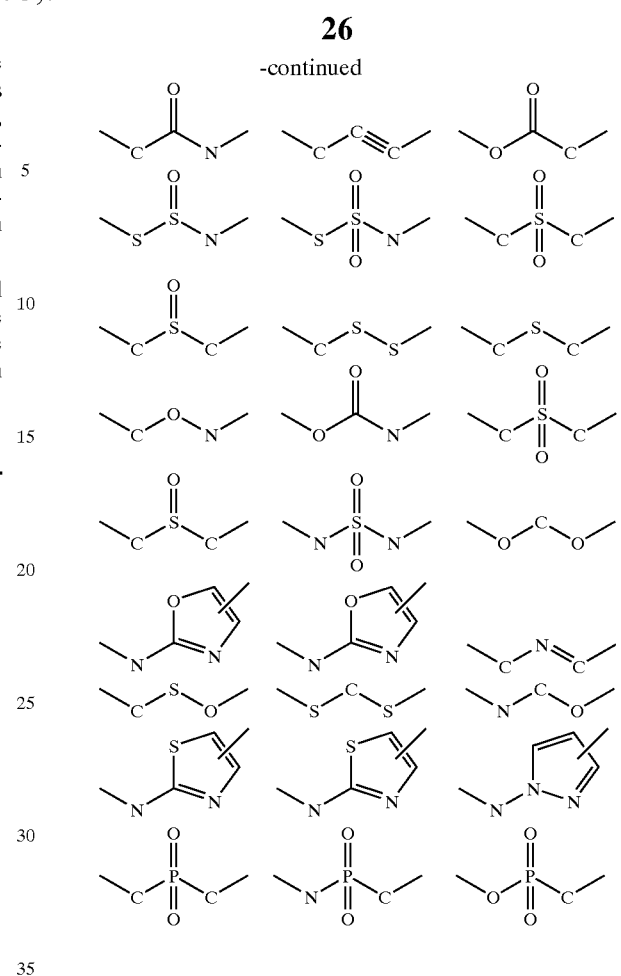

Figure 2:
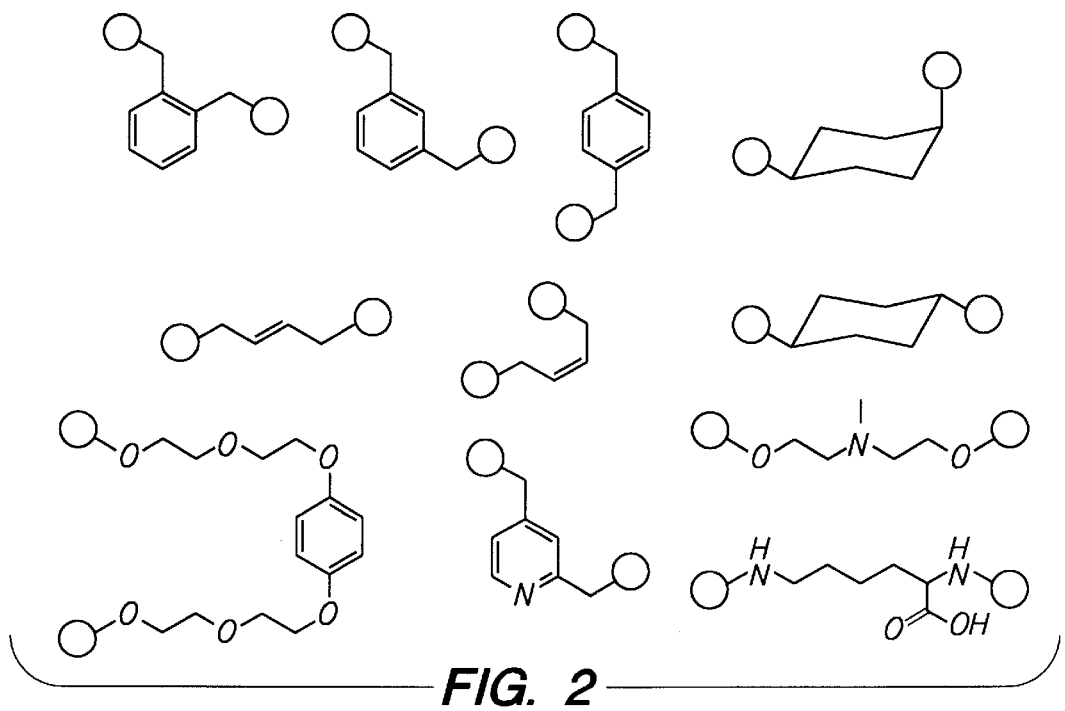
FIG. 2 illustrates examples of multibinding compounds comprising 2 ligands attached in different formats to a linker.

The identification of an appropriate framework geometry and size for ligand domain presentation are important steps in the construction of a multibinding compound with enhanced activity. Systematic spatial searching strategies can be used to aid in the identification of preferred frameworks through an iterative process. FIG. 2 illustrates a useful strategy for determining an optimal framework display orientation for ligand domains. Various other strategies are known to those skilled in the art of molecular design and can be used for preparing compounds of this invention.

As shown in FIG. 2, display vectors around similar central core structures such as a phenyl structure and a cyclohexane structure can be varied, as can the spacing of the ligand domain from the core structure (i.e., the length of the attaching moiety). It is to be noted that core structures other than those shown here can be used for determining the optimal framework display orientation of the ligands. The process may require the use of multiple copies of the same central core structure or combinations of different types of display cores.

Figure 3:
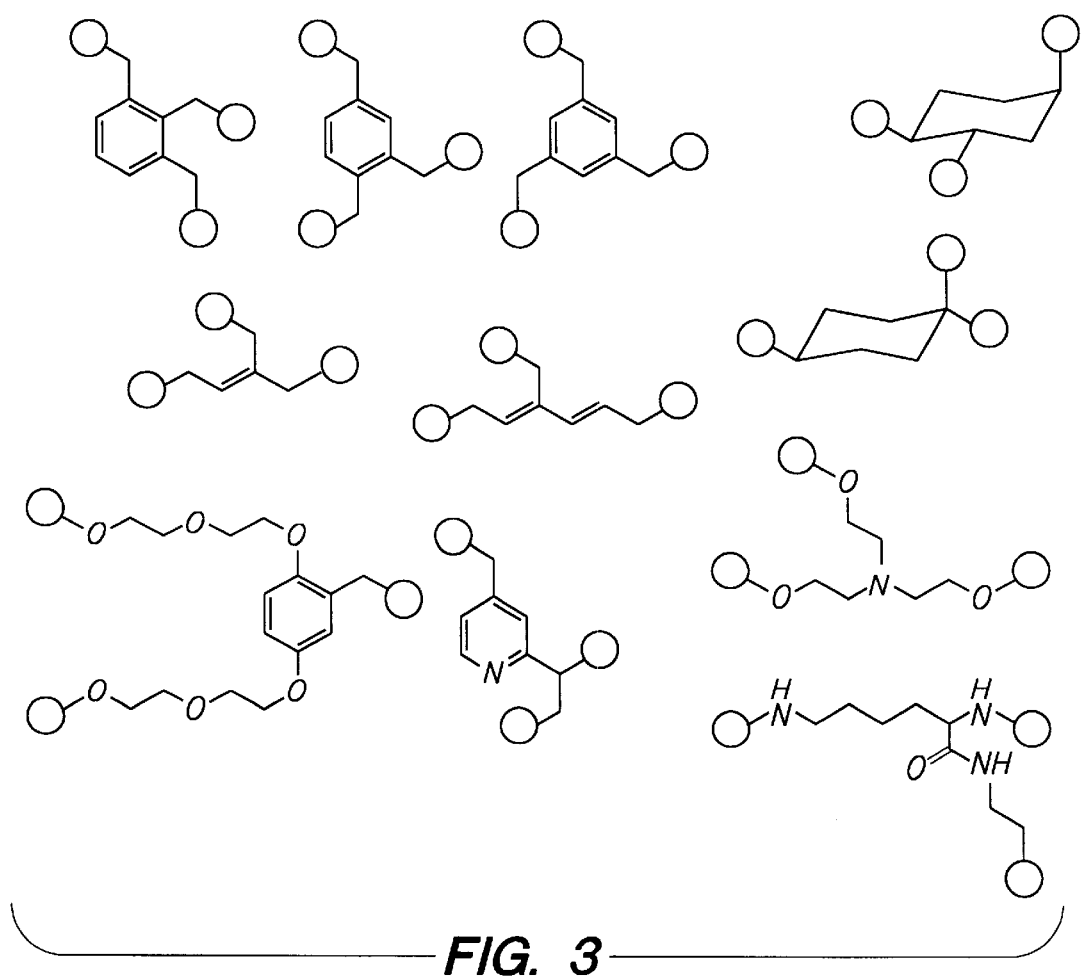
FIG. 3 illustrates examples of multibinding compounds comprising 3 ligands attached in different formats to a linker.
Figure 4:
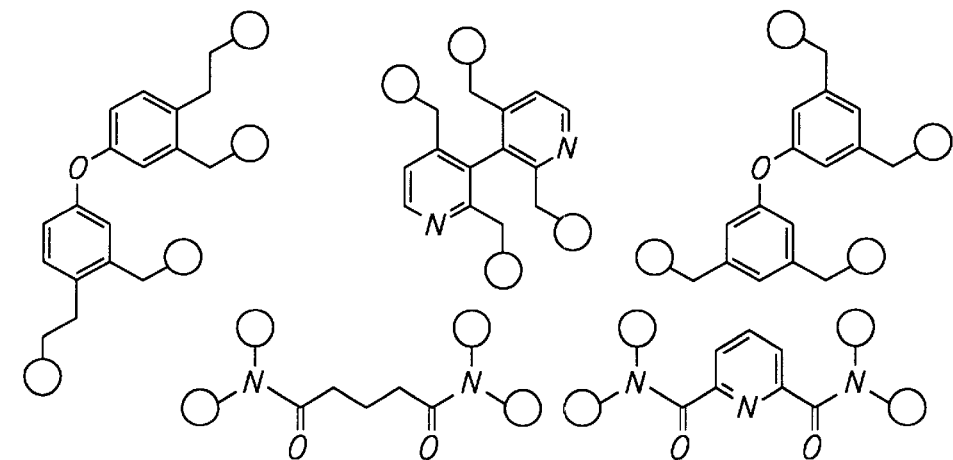
FIG. 4 illustrates examples of multibinding compounds comprising 4 ligands attached in different formats to a linker.
Figure 4:
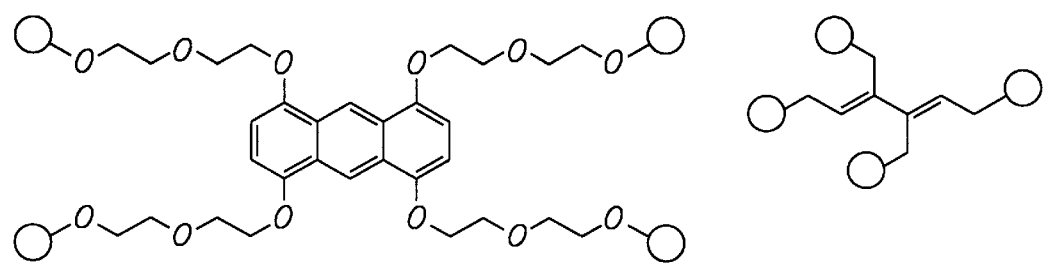
Figure 4:
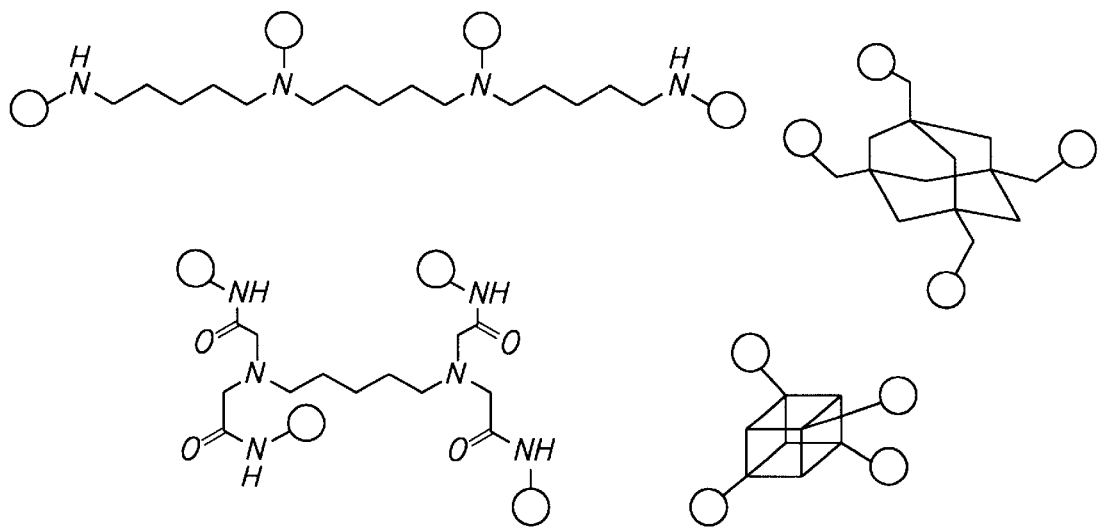
Figure 5:
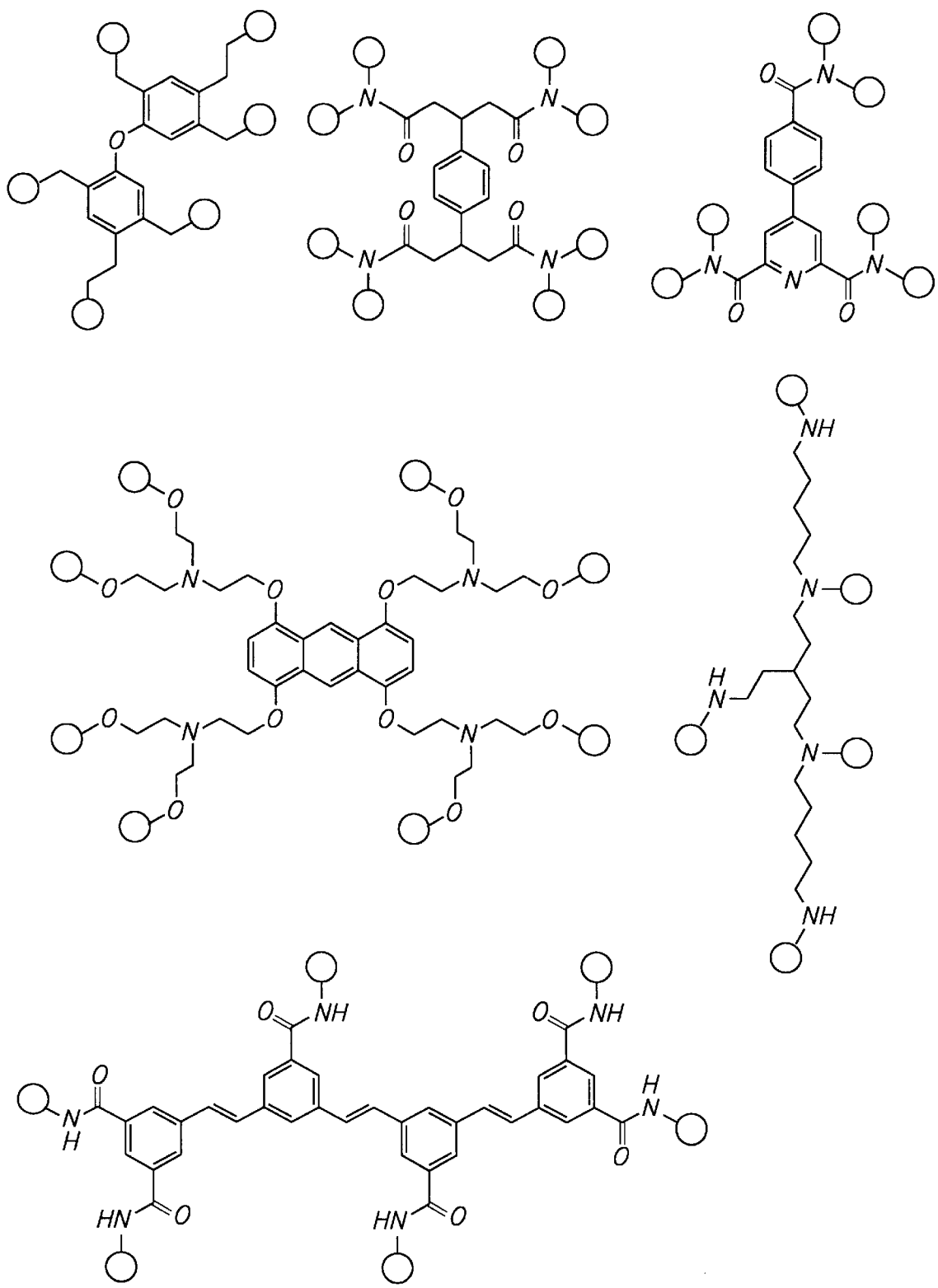
FIG. 5 illustrates examples of multibinding compounds comprising >4 ligands attached in different formats to a linker.

The above-described process can be extended to trimers (FIG. 3) and compounds of higher valency (FIG. 4 and FIG. 5).

Assays of each of the individual compounds of a collection generated as described above will lead to a subset of compounds with the desired enhanced activities (e.g., potency, selectivity, etc.). The analysis of this subset using a technique such as Ensemble Molecular Dynamics will provide a framework orientation that favors the properties desired. A wide diversity of linkers is commercially available (see, e.g., Available Chemical Directory (ACD)). Many of the linkers that are suitable for use in this invention fall into this category. Other can be readily synthesized by methods well known in the art and/or are described below.

Having selected a preferred framework geometry, the physical properties of the linker can be optimized by varying the chemical composition thereof. The composition of the linker can be varied in numerous ways to achieve the desired physical properties for the multibinding compound.

It can therefore be seen that there is a plethora of possibilities for the composition of a linker. Examples of linkers include aliphatic moieties, aromatic moieties, steroidal moieties, peptides, and the like. Specific examples are peptides or polyamides, hydrocarbons, aromatic groups, ethers, lipids, cationic or anionic groups, or a combination thereof.

Examples are given below, but it should be understood that various changes may be made and equivalents may be substituted without departing from the true spirit and scope of the invention. For example, properties of the linker can be modified by the addition or insertion of ancillary groups into or onto the linker, for example, to change the solubility of the multibinding compound (in water, fats, lipids, biological fluids, etc.), hydrophobicity, hydrophilicity, linker flexibility, antigenicity, stability, and the like. For example, the introduction of one or more poly(ethylene glycol) (PEG) groups onto or into the linker enhances the hydrophilicity and water solubility of the multibinding compound, increases both molecular weight and molecular size and, depending on the nature of the unPEGylated linker, may increase the in vivo retention time. Further PEG may decrease antigenicity and potentially enhances the overall rigidity of the linker.

Ancillary groups which enhance the water solubility/hydrophilicity of the linker and, accordingly, the resulting multibinding compounds are useful in practicing this invention. Thus, it is within the scope of the present invention to use ancillary groups such as, for example, small repeating units of ethylene glycols, alcohols, polyols (e.g., glycerin, glycerol propoxylate, saccharides, including mono-, oligosaccharides, etc.), carboxylates (e.g., small repeating units of glutamic acid, acrylic acid, etc.), amines (e.g., tetraethylenepentamine), and the like) to enhance the water solubility and/or hydrophilicity of the multibinding compounds of this invention. In preferred embodiments, the ancillary group used to improve water solubility/hydrophilicity will be a polyether .

The incorporation of lipophilic ancillary groups within the structure of the linker to enhance the lipophilicity and/or hydrophobicity of the multibinding compounds described herein is also within the scope of this invention. Lipophilic groups useful with the linkers of this invention include, by way of example only, aryl and heteroaryl groups which, as above, may be either unsubstituted or substituted with other groups, but are at least substituted with a group which allows their covalent attachment to the linker. Other lipophilic groups useful with the linkers of this invention include fatty acid derivatives which do not form bilayers in aqueous medium until higher concentrations are reached.

Also within the scope of this invention is the use of ancillary groups which result in the multibinding compound being incorporated or anchored into a vesicle or other membranous structure such as a liposome or a micelle. The term "lipid" refers to any fatty acid derivative that is capable of forming a bilayer or a micelle such that a hydrophobic portion of the lipid material orients toward the bilayer while a hydrophilic portion orients toward the aqueous phase. Hydrophilic characteristics derive from the presence of phosphato, carboxylic, sulfato, amino, sulfhydryl, nitro and other like groups well known in the art. Hydrophobicity could be conferred by the inclusion of groups that include, but are not limited to, long chain saturated and unsaturated aliphatic hydrocarbon groups of up to 20 carbon atoms and such groups substituted by one or more aryl, heteroaryl, cycloalkyl, and/or heterocyclic group(s). Preferred lipids are phosphglycerides and sphingolipids, representative examples of which include phosphatidylcholine, phosphatidylethanolamine, phosphatidylserine, phosphatidylinositol, phosphatidic acid, palmitoyleoyl phosphatidylcholine, lysophosphatidylcholine, lysophosphatidyl-ethanolamine, dipalmitoylphosphatidylcholine, dioleoylphosphatidylcholine, distearoyl-phosphatidylcholine or dilinoleoylphosphatidylcholine could be used. Other compounds lacking phosphorus, such as sphingolipid and glycosphingolipid families are also within the group designated as lipid. Additionally, the amphipathic lipids described above may be mixed with other lipids including triglycerides and sterols.

The flexibility of the linker can be manipulated by the inclusion of ancillary groups which are bulky and/or rigid. The presence of bulky or rigid groups can hinder free rotation about bonds in the linker or bonds between the linker and the ancillary group(s) or bonds between the linker and the functional groups. Rigid groups can include, for example, those groups whose conformational lability is restrained by the presence of rings and/or multiple bonds within the group, for example, aryl, heteroaryl, cycloalkyl, cycloalkenyl, and heterocyclic groups. Other groups which can impart rigidity include polypeptide groups such as oligo- or polyproline chains.

Rigidity may also be imparted by internal hydrogen bonding or by hydrophobic collapse.

Bulky groups can include, for example, large atoms, ions (e.g., iodine, sulfur, metal ions, etc.) or groups containing large atoms, polycyclic groups, including aromatic groups, non-aromatic groups and structures incorporating one or more carbon-carbon multiple bonds (i.e., alkenes and alkynes). Bulky groups can also include oligomers and polymers which are branched- or straight-chain species. Species that are branched are expected to increase the rigidity of the structure more per unit molecular weight gain than are straight-chain species.

In preferred embodiments, rigidity is imparted by the presence of cyclic groups (e.g., aryl, heteroaryl, cycloalkyl, heterocyclic, etc.). In other preferred embodiments, the linker comprises one or more six-membered rings. In still further preferred embodiments, the ring is an aryl group such as, for example, phenyl or naphthyl.

Rigidity can also be imparted electrostatically. Thus, if the ancillary groups are either positively or negatively charged, the similarly charged ancillary groups will force the presenter linker into a configuration affording the maximum distance between each of the like charges. The energetic cost of bringing the like-charged groups closer to each other will tend to hold the linker in a configuration that maintains the separation between the like-charged ancillary groups. Further ancillary groups bearing opposite charges will tend to be attracted to their oppositely charged counterparts and potentially may enter into both inter- and intramolecular ionic bonds. This non-covalent mechanism will tend to hold the linker into a conformation which allows bonding between the oppositely charged groups. The addition of ancillary groups which are charged, or alternatively, bear a latent charge when deprotected, following addition to the linker, include deprotectation of a carboxyl, hydroxyl, thiol or amino group by a change in pH, oxidation, reduction or other mechanisms known to those skilled in the art which result in removal of the protecting group, is within the scope of this invention.

In view of the above, it is apparent that the appropriate selection of a linker group providing suitable orientation, restricted/unrestricted rotation, the desired degree of hydrophobicity/hydrophilicity, etc. is well within the skill of the art. Eliminating or reducing antigenicity of the multibinding compounds described herein is also within the scope of this invention. In certain cases, the antigenicity of a multibinding compound may be eliminated or reduced by use of groups such as, for example, poly(ethylene glycol).

As explained above, the multibinding compounds described herein comprise 2–10 ligands attached to a linker that links the ligands in such a manner that they are presented to the enzyme for multivalent interactions with ligand binding sites thereon/therein. The linker spatially constrains these interactions to occur within dimensions defined by the linker. This and other factors increases the biological activity of the multibinding compound as compared to the same number of ligands made available in monobinding form.

The compounds of this invention are preferably represented by the empirical formula $(L)_p(X)_q$ where L, X, p and q are as defined above. This is intended to include the several ways in which the ligands can be linked together in order to achieve the objective of multivalency, and a more detailed explanation is described below.

As noted previously, the linker may be considered as a framework to which ligands are attached. Thus, it should be recognized that the ligands can be attached at any suitable position on this framework, for example, at the termini of a linear chain or at any intermediate position.

The simplest and most preferred multibinding compound is a bivalent compound which can be represented as L—X—L, where each L is independently a ligand which may be the same or different and each X is independently the linker. Examples of such bivalent compounds are provided in FIG. 2 where each shaded circle represents a ligand. A trivalent compound could also be represented in a linear fashion, i.e., as a sequence of repeated units L—X—L—X—L, in which L is a ligand and is the same or different at each occurrence, as can X. However, a trimer can also be a radial multibinding compound comprising three ligands attached to a central core, and thus represented as $(L)_3X$, where the linker X could include, for example, an aryl or cycloalkyl group. Illustrations of trivalent and tetravalent compounds of this invention are found in FIGs. 3 and 4 respectively where, again, the shaded circles represent ligands. Tetravalent compounds can be represented in a linear array, e.g.,

L—X—L—X—L—X—L in a branched array, e.g.,

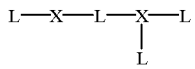

(a branched construct analogous to the isomers of butane— n-butyl, iso-butyl, sec-butyl, and t-butyl) or in a tetrahedral array, e.g.,

where X and L are as defined herein. Alternatively, it could be represented as an alkyl, aryl or cycloalkyl derivative as above with four (4) ligands attached to the core linker.

The same considerations apply to higher multibinding compounds of this invention containing 5–10 ligands as illustrated in FIG. 5 where, as before, the shaded circles represent ligands. However, for multibinding agents attached to a central linker such as aryl or cycloalkyl, there is a self-evident constraint that there must be sufficient attachment sites on the linker to accommodate the number of ligands present; for example, a benzene ring could not directly accommodate more than 6 ligands, whereas a multi-ring linker (e.g., biphenyl) could accommodate a larger number of ligands.

Certain of the above described compounds may alternatively be represented as cyclic chains of the form:

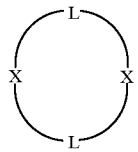

and variants thereof.

All of the above variations are intended to be within the scope of the invention defined by the formula $(L)_p(X)_q$.

With the foregoing in mind, a preferred linker may be represented by the following formula:

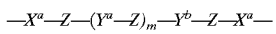

in which:

m is an integer of from 0 to 20;

$X^a$ at each separate occurrence is selected from the group consisting of —O—, —S—, —NR—, —C(O)—, —C(O)O—, —C(O)NR—, —C(S), —C(S)O—, —C(S)NR— or a covalent bond where R is as defined below;

Z is at each separate occurrence is selected from the group consisting of alkylene, substituted alkylene, cycloalkylene, substituted cycloalkylene, alkenylene, substituted alkenylene, alkynylene, substituted alkynylene, cycloalkenylene, substituted cycloalkenylene, arylene, heteroarylene, heterocyclene, or a covalent bond;

$Y^a$ and $Y^b$ at each separate occurrence are selected from the group consisting of:

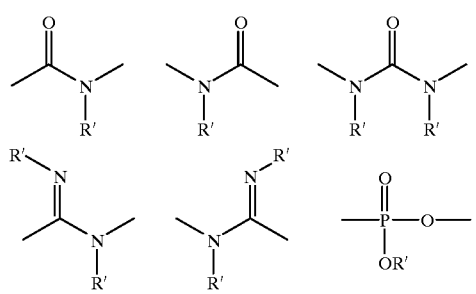

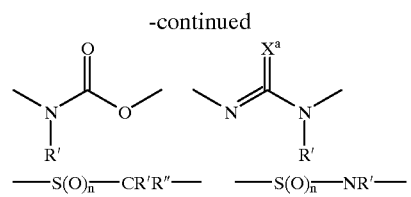

—S—S— or a covalent bond;
in which:
n is 0, 1 or 2; and

R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic.

Additionally, the linker moiety can be optionally substituted at any atom therein by one or more alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic group.

In one embodiment of this invention, the linker (i.e., X, X' or X") is selected those shown in Table II:

TABLE II

Representative Linkers

| Linker |
|---|
| —HN—$(CH_2)_2$—NH—C(O)—$(CH_2)$—C(O)—NH—$(CH_2)_2$—NH— |
| —HN—$(CH_2)_2$—NH—C(O)—$(CH_2)_2$—C(O)—NH—$(CH_2)_2$—NH— |
| —HN—$(CH_2)_2$—NH—C(O)—$(CH_2)_3$—C(O)—NH—$(CH_2)_2$—NH— |
| —HN—$(CH_2)_2$—NH—C(O)—$(CH_2)_4$—C(O)—NH—$(CH_2)_2$—NH— |
| —HN—$(CH_2)_2$—NH—C(O)—$(CH_2)_5$—C(O)—NH—$(CH_2)_2$—NH— |
| —HN—$(CH_2)_2$—NH—C(O)—$(CH_2)_6$—C(O)—NH—$(CH_2)_2$—NH— |
| —HN—$(CH_2)_2$—NH—C(O)—$(CH_2)_7$—C(O)—NH—$(CH_2)_2$—NH— |
| —HN—$(CH_2)_2$—NH—C(O)—$(CH_2)_8$—C(O)—NH—$(CH_2)_2$—NH— |
| —HN—$(CH_2)_2$—NH—C(O)—$(CH_2)_9$—C(O)—NH—$(CH_2)_2$—NH— |
| —HN—$(CH_2)_2$—NH—C(O)—$(CH_2)_{10}$—C(O)—NH—$(CH_2)_2$—NH— |
| —HN—$(CH_2)_2$—NH—C(O)—$(CH_2)_{11}$—C(O)—NH—$(CH_2)_2$—NH— |
| —HN—$(CH_2)_2$—NH—C(O)—$(CH_2)_{12}$—C(O)—NH—$(CH_2)_2$—NH— |
| —HN—$(CH_2)_2$—NH—C(O)—Z—C(O)—NH—$(CH_2)_2$—NH— where Z is 1,2-phenyl |
| —HN—$(CH_2)_2$—NH—C(O)—Z—C(O)—NH—$(CH_2)_2$—NH— where Z is 1,3-phenyl |
| —HN—$(CH_2)_2$—NH—C(O)—Z—C(O)—NH—$(CH_2)_2$—NH— where Z is 1,4-phenyl |
| —HN—$(CH_2)_2$—NH—C(O)—Z—O—Z—C(O)—NH—$(CH_2)_2$—NH— where Z is 1,4-phenyl |
| —HN—$(CH_2)_2$—NH—C(O)—$(CH_2)_2$—CH(NH—C(O)—$(CH_2)_8$—$CH_3$)—C(O)—NH—$(CH_2)_2$—NH— |
| —HN—$(CH_2)_2$—NH—C(O)—$(CH_2)_2$—O—$(CH_2)_2$—C(O)—NH—$(CH_2)_2$—NH— |
| —HN—$(CH_2)_2$—NH—C(O)—$(CH_2)_2$—CH(NH—C(O)—Z)—C(O)—NH—$(CH_2)_2$—NH— where Z is 5-(n-octadecyloxy)-1,3-phenyl |
| —HN—$(CH_2)_2$—NH—C(O)—Z—C(O)—NH—$(CH_2)_2$—NH— where Z is 4-biphenyl |
| —HN—$(CH_2)_2$—NH—C(O)—Z—C(O)—NH—$(CH_2)_2$—NH— where Z is 5-(n-butyloxy)-1,3-phenyl |

TABLE II-continued

Representative Linkers

| Linker | |
|---|---|
| —HN—(CH$_2$)$_2$—NH—C(O)—(CH$_2$)$_8$-trans-(CH=CH)—C(O)—NH—(CH$_2$)$_2$—NH— | |
| —HN—(CH$_2$)$_2$—NH—C(O)—(CH$_2$)$_2$—CH(NH—C(O)—(CH$_2$)$_{12}$—CH$_3$)—C(O)—NH—(CH$_2$)$_2$—NH— | |
| —HN—(CH$_2$)$_2$—NH—C(O)—(CH$_2$)$_2$—CH(NH—C(O)—Z)—C(O)—NH—(CH$_2$)$_2$—NH— | where Z is 4-(n-octyl)—phenyl |
| —HN—(CH$_2$)—Z—O—(CH$_2$)$_6$—O—Z—(CH$_2$)—NH— | where Z is 1,4-phenyl |
| —HN—(CH$_2$)$_2$—NH—C(O)—(CH$_2$)$_2$—NH—C(O)—(CH$_3$)$_3$—C(O)—NH—(CH$_2$)$_2$—C(O)—NH—(CH$_2$)$_2$—NH— | |
| —HN—(CH$_2$)$_2$—NH—C(O)—(CH$_2$)$_2$—CH(NH—C(O)—Ph)—C(O)—NH—(CH$_2$)$_2$—NH— | |
| —HN—(CH$_2$)$_2$—NH—C(O)—(CH$_2$)$_2$—N+((CH$_2$)$_9$—CH$_3$)(CH$_2$—C(O)—NH—(CH$_2$)$_2$—NH$_2$)—(CH$_2$)—C(O)—NH—(CH$_2$)$_2$—NH— | |
| —HN—(CH$_2$)$_2$—NH—C(O)—(CH$_2$)—N((CH$_2$)$_9$—CH$_3$)—(CH$_2$)—C(O)—NH—(CH$_2$)$_2$—NH— | |
| —HN—(CH$_2$)$_2$—NH—C(O)—(CH$_2$)$_2$—NH—C(O)—(CH$_2$)$_3$—NH—C(O)—(CH$_2$)$_2$—C(O)—NH—(CH$_2$)$_2$—C(O)—NH—(CH$_2$)$_2$—C(O)—NH—(CH$_2$)$_2$—NH— | |
| —HN—(CH$_2$)$_2$—NH—C(O)—Z—C(O)—NH—(CH$_2$)$_2$—NH— | where Z is 5-hydroxy-1,3-phenyl |

In another embodiment of this invention, the linker (i.e., X, X' or X") has the formula:

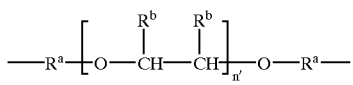

wherein each $R^a$ is independently selected from the group consisting of a covalent bond, alkylene, substituted alkylene and arylene;

each $R^b$ is independently selected from the group consisting of hydrogen, alkyl and substituted alkyl; and n' is an integer ranging from 1 to about 20.

In yet another embodiment, the linker (i.e., X or X') has the formula: —$(CH_2)_{n'}$—, where n' is an integer ranging from 1 to about 20, preferably from 2 to 6.

In view of the above description of the linker, it is understood that the term "linker" when used in combination with the term "multibinding compound" includes both a covalently contiguous single linker (e.g., L—X—L) and multiple covalently non-contiguous linkers (L—X—L—X—L) within the multibinding compound.

Preparation of Multibinding Compounds

The multibinding compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis*, Second Edition, Wiley, N.Y., 1991, and references cited therein.

Any compound which binds to or inhibits cyclooxygenase-2 can be used as a ligand in this invention. As discussed in further detail below, numerous such cyclooxygenase-2 inhibitors are known in the art[7] and any of these known compounds or derivatives thereof may be employed as ligands in this invention. Typically, a compound selected for use as a ligand will have at lease one functional group, such as an amino, hydroxyl, thiol or carboxyl group and the like, which allows the compound to be readily coupled to the linker. Compounds having such functionality are either known in the art or can be prepared by routine modification of known compounds using conventional reagents and procedures. The patents and publications set forth below provide numerous examples of suitably functionalized cyclooxygenase-2 inhibitors and intermediates thereof which may be used as ligands in this invention.

The ligand can be covalently attached to the linker through any available position on the ligand, provided that when the ligand is attached to the linker, the ligand retains its ability to bind to or inhibit cyclooxygenase-2. Certain sites of attachment of the linker to the ligand are preferred based on known structure-activity relationships.[7,8] Preferably, the linker is attached to a site on the ligand where structure-activity studies show that a wide variety of substituents are tolerated without loss of enzyme binding activity. For example, many known cyclooxygenase-2 inhibitors contain, among other structural features, a phenyl ring substituted typically in the 4-position with a sulfone or related type substituent. This sulfone-substituted phenyl ring is typically attached to a 4, 5 or 6-membered ring (i.e., rings A, B and C in formulas IA, IB and IC). Structure-activity studies show that only very minor modifications are tolerated on the sulfone-substituted phenyl ring.[8] Accordingly, the ligand is preferably not attached to the linker through this phenyl ring. On the other hand, structure-activity studies indicate that large groups are typically tolerated on the 4, 5 or 6 membered ring provide there is no lateral steric bulk associated with the substituent. Accordingly, the ligand is preferably attached to the linker via ring A, B or C in formulas IA, IB and IC.

A first group of preferred ligands for use in this invention are those ligands having formula IA, IB and IC:

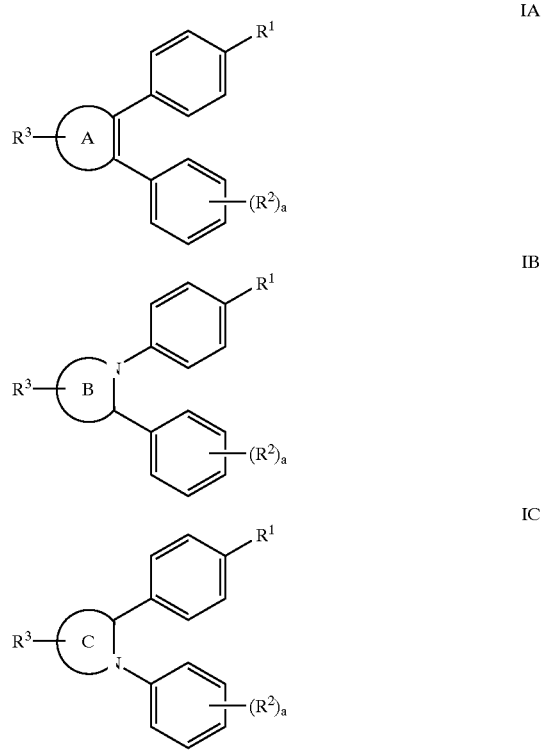

wherein ring A, ring B, ring C, $R^1$, $R^2$, $R^3$ and α are as defined herein.

Ligands of formula IA, IB and IC (and the precursors thereof) are well-known in the art and can be readily prepared using art-recognized starting materials, reagents and reaction conditions. By way of illustration, the following patents and publications disclose compounds, intermediates and procedures useful in the preparation of ligands of formula IA, IB, IC or related compounds suitable for use in this invention: U.S. Pat. No. 5,616,601, issued Apr. 1, 1997 to Khanna et al.; U.S. Pat. No. 5,643,933, issued Jul. 1, 1997 to Talley et al.; U.S. Pat. No. 5,691,374, issued Nov. 25, 1997 to Black et al.; and P. Prait et al., *Annual Reports in*

*Medicinal Chemistry* 1997, 32, 211–220. Each of these patents and publications is incorporated herein by reference in its entirety to the same extent as if each individual patent or publication was specifically and individually indicated to be incorporated by reference in its entirety.

Figure 6:
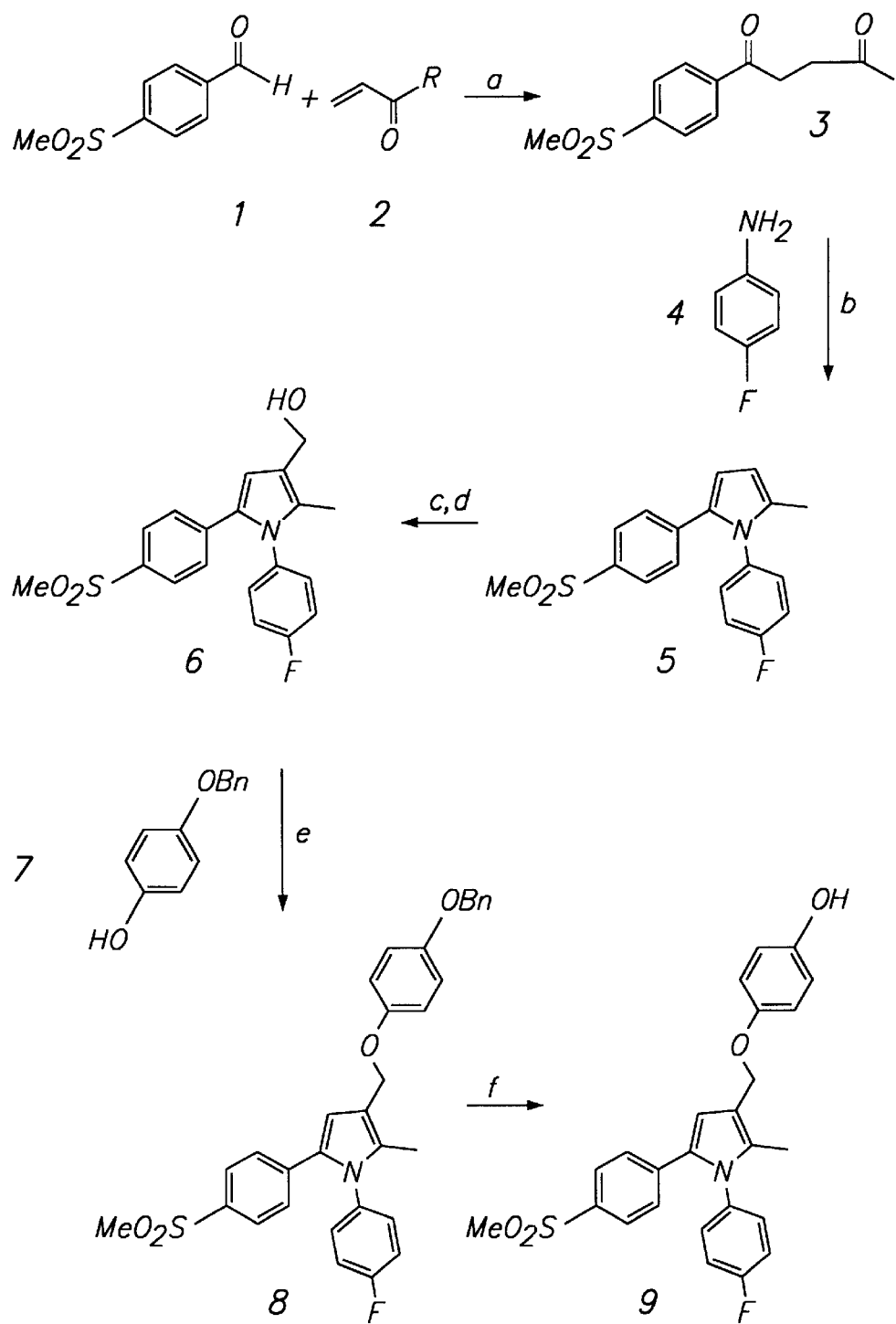
FIG. 6 illustrates a representative synthesis of a ligand precursor.

A representative synthesis of a ligand precursor is illustrated in FIG. 6. It will be understood by those skilled in the art that the following methods may be used to prepare other multibinding compounds of this invention. FIG. 6 illustrates the synthesis of a ligand precursor having a hydroxyl attachment site. As shown in FIG. 6, 4-(methysulfonyl) benzaldehyde, 1, is first reacted with methyl vinyl ketone, 2 (where R is methyl), in the presence of triethylamine and a catalytic amount of 3-ethyl-5-(2-hydroxyethyl)4-methylthiazolium bromide to form diketone 3. This reaction is typically conducted for about 5 hours in refluxing ethanol. Diketone 3 is then reacted with 4-fluoroaniline, 4, in the presence of a catalytic amount of p-toluenesulfonic acid to provide pyrrole 5. This reaction is typically conducted in refluxing toluene for about 20 hours.

Pyrrole 5 is then hydroxymethylated by first reacting 5 with N,N-dimethylformamide and phosphorus oxychloride (POCl$_3$) and then reducing the resulting aldehyde with a reducing agent, such as sodium cyanoborohydride, to afford hydroxymethyl pyrrole 6. 4-(Benzyloxy)phenol, 7, is then readily coupled to 6 using the Mitsunobu reaction to provide intermediate 8. This reaction is conducted by reacting 6 and 7 using diethyl azodicarboxylate (DEAD) and triphenylphosphine at ambient temperature for about 48 hours. Removal of the benzyl protecting group from intermediate 8 using conventional procedures, i.e., hydrogenolysis in the presence of a suitable catalyst, such as palladium on carbon, then affords ligand precursor 9.

Figure 7:
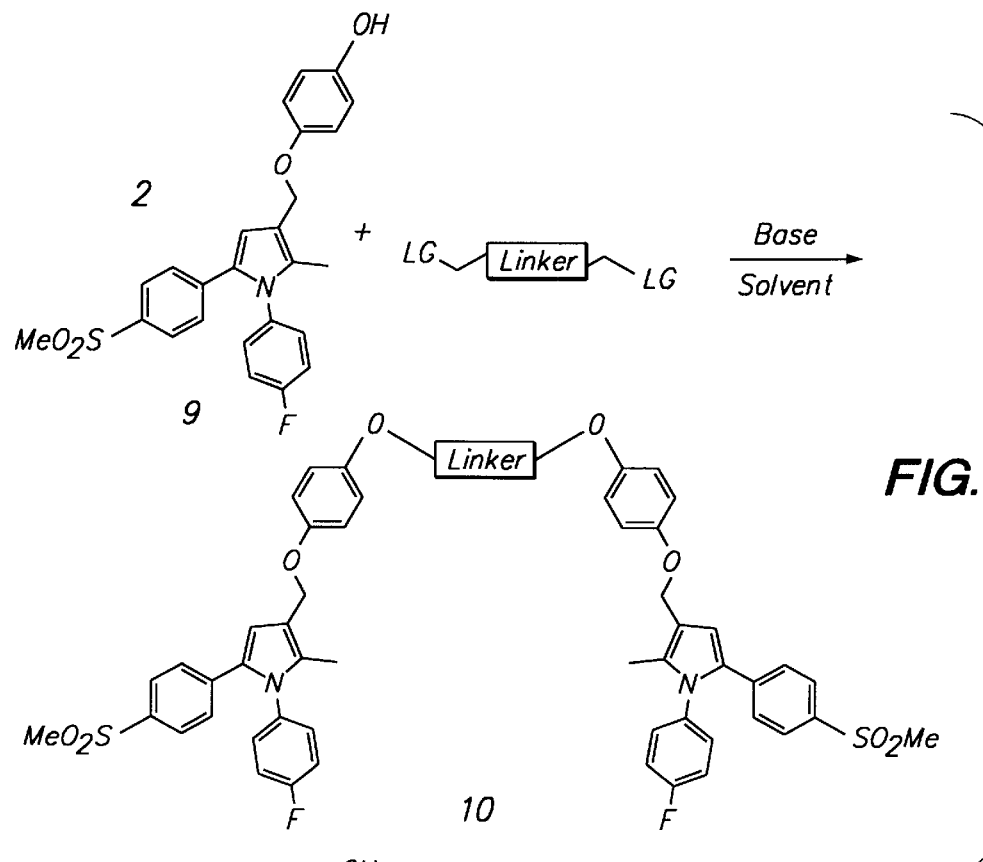
FIG. 7 and FIG. 8 illustrate dimer formation by alkylation of a hydroxyl-containing intermediate with a bis-electrophile.

Ligand precursor 9 can then be covalently linked to a linker using conventional reagents and conditions. For example, two equivalents of ligand precursor 9 can be readily coupled to a linker precursor to form a dimer as illustrated in FIG. 7. As shown in FIG. 7, ligand precursor 9 is reacted with a linker precursor having at least two leaving groups (i.e., as shown in FIG. 7 where "LG" is a leaving group and "Linker" is the non-reactive portion of the linker precursor) in the presence of base to form dimer 10. The leaving group employed in this reaction may be any conventional leaving group including, by way of example, a halogen such as chloro, bromo or iodo, or a sulfonate group such as tosyl, mesyl and the like. Any base which effectively deprotonates the phenolic hydroxyl group may be used in this reaction including, by way of illustration, sodium carbonate, potassium carbonate, cesium carbonate, sodium hydride, sodium hydroxide, potassium hydroxide, sodium ethoxide, triethylamine, diisopropylethylamine and the like. This reaction is typically conducted in an inert diluent, such as tetrahydrofuran, N,N-dimethylformamide, N,N-dimethylacetamide, acetone, 2-butanone, 1-methyl-2-pyrrolidinone, water and the like. After the reaction is complete, dimer 10 is typically isolated using conventional procedures, such as extraction, filtration, chromatography and the like.

Figure 8:
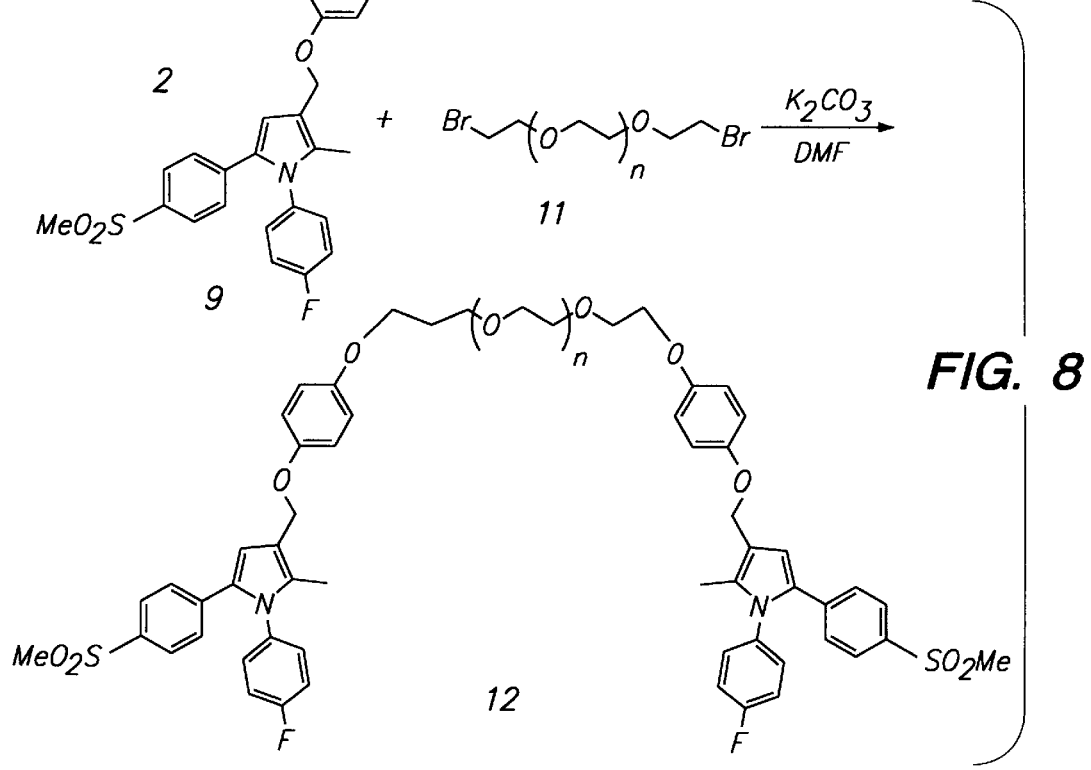

By way of further illustration, FIG. 8 shows the formation of a dimer using ligand precursor 9 and a poly(oxyethylene) dibromide, 11 (where n is typically an integer from 1 to about 20). In this reaction, two molar equivalents of 9 are reacted with one molar equivalent of the poly(oxyethylene) dibromide 11 in the presence of excess potassium carbonate to afford dimer 12. This reaction is typically conducted in N,N-dimethylformamide at a temperature ranging from about 25° C. to about 100° C. for about 6 to about 48 hours.

Figure 9:
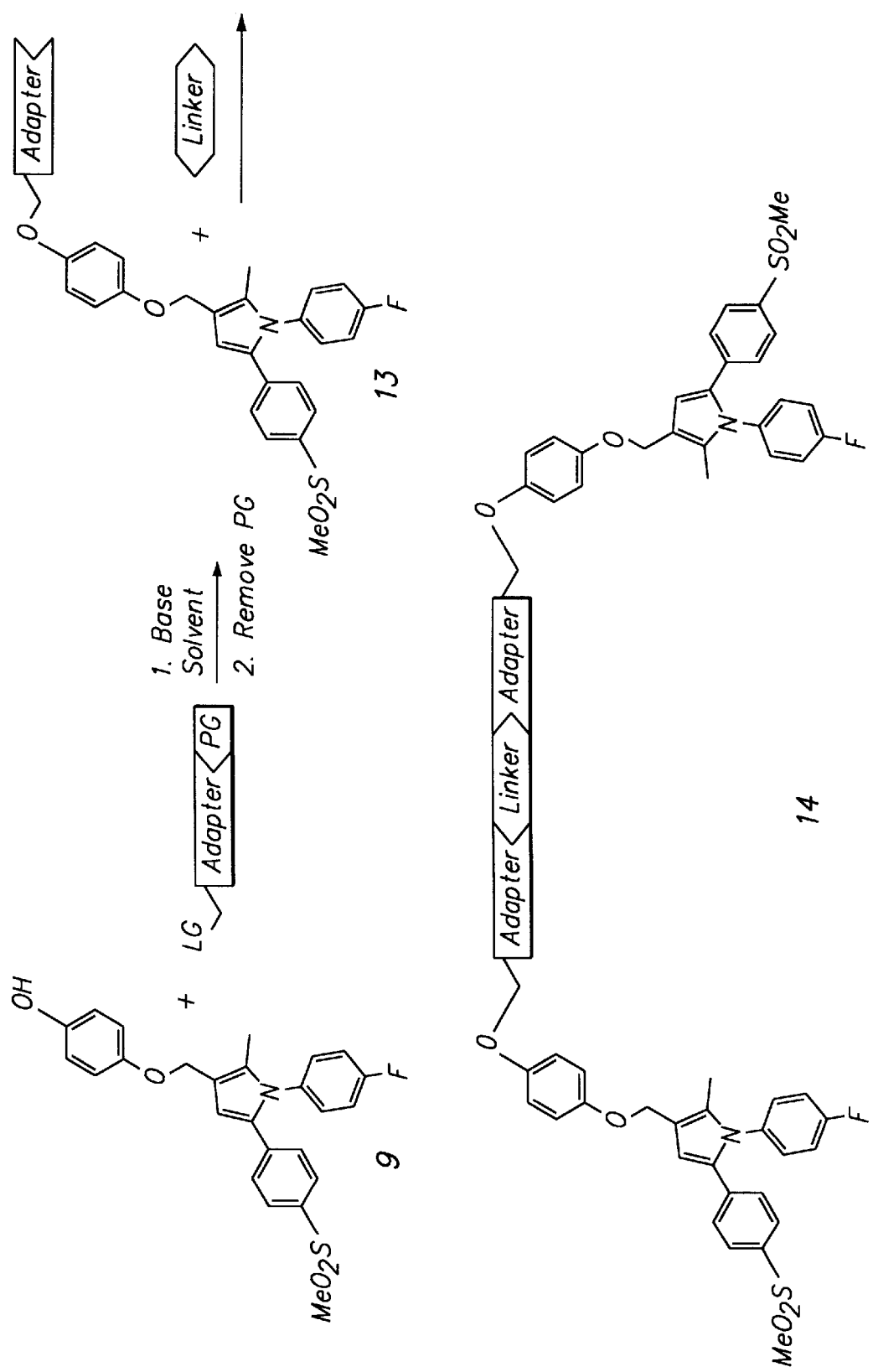
FIG. 9 illustrates dimer formation using an adapter.

Alternatively, the linker connecting the ligands may be prepared in several steps as illustrated in FIG. 9. Specifically, a ligand precursor, such as 9, can first be coupled to an "adapter", i.e., a bifunctional group having a leaving group at one end and another functional group at the other end which allows the adapter to be coupled to a intermediate linker group. In some cases, the functional group used to couple to the intermediate linker is temporarily masked with a protecting group ("PG"). Representative examples of adapters include, by way of illustration, tert-butyl bromoacetate, 1-Fmoc-2-bromoethylamine, 1-trityl-2-bromoethanethiol, 4-iodobenzyl bromide, propargyl bromide and the like. As further illustrated in FIG. 9, after the ligand precursor 9 is coupled to the adapter and the protecting group is removed from the adapter's functional group (if a protecting group is present) to form intermediate 13, two molar equivalents of intermediate 13 are then coupled with an intermediate linker to form dimer 14.

Figure 10:
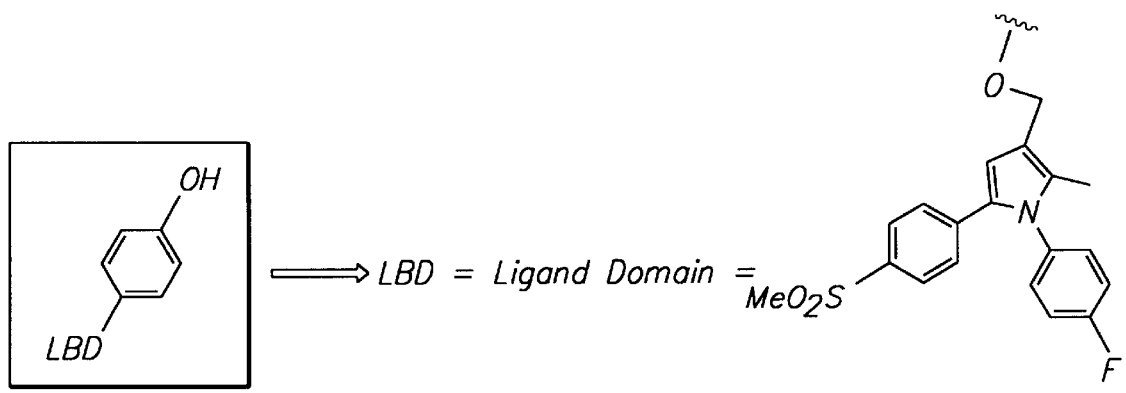
FIG. 10 and FIG. 11 illustrate representative syntheses of a ligand precursor containing an adaptor.
Figure 10:
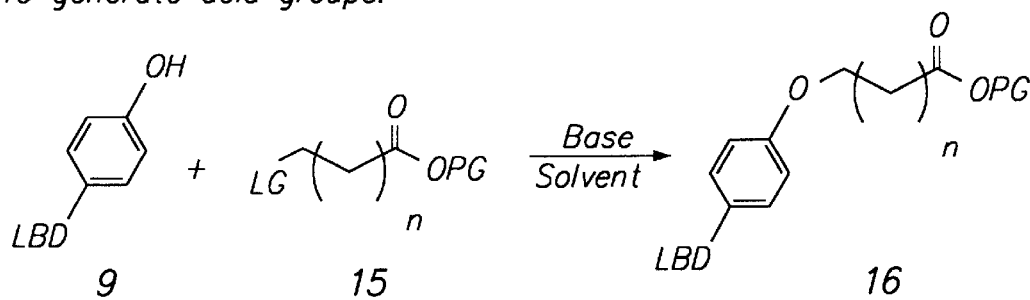
Figure 10:
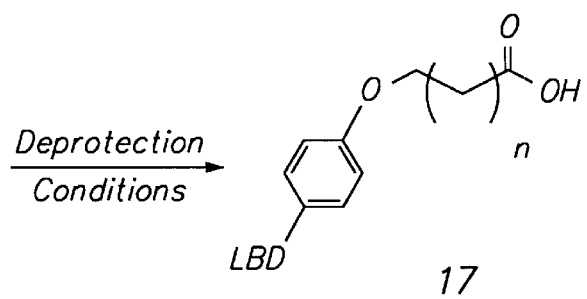
Figure 11:
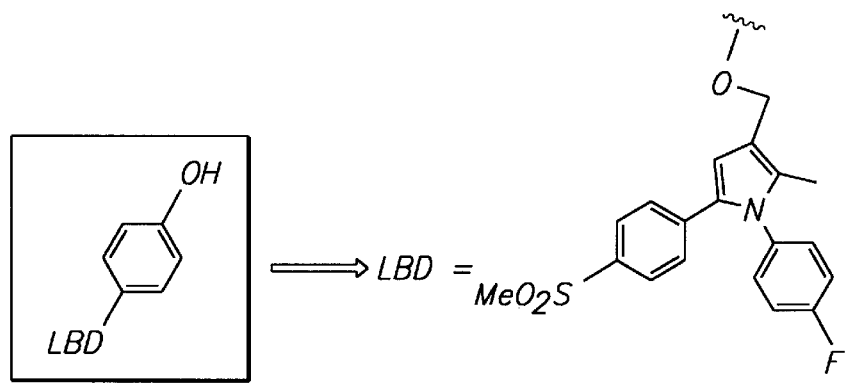
Figure 11:
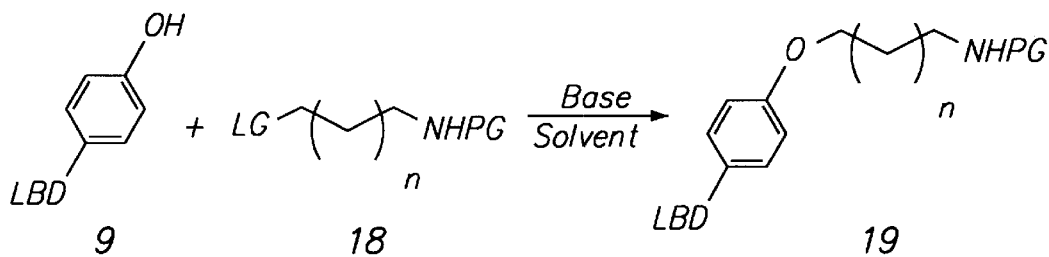
Figure 11:
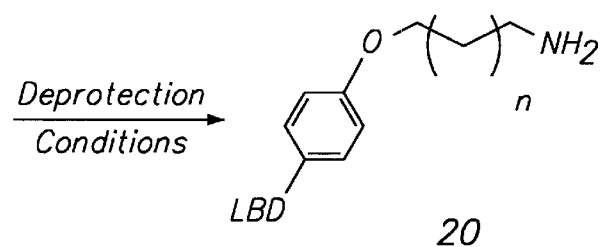

By way of further illustration, FIGS. 10 and 11 show the syntheses of ligand precursors containing representative adapters. In FIG. 10, ligand precursor 9 is coupled with adapter 15 (where "LG" is a leaving group, "PG" is a protecting group and n is typically an integer from 1 to about 20) to afford protected intermediate 16. The leaving group employed in this reaction may be any conventional leaving group including, by way of example, a halogen such as chloro, bromo or iodo, or a sulfonate group such as tosyl, mesyl and the like. Similarly, any conventional protecting group may be employed including, by way of example, esters such as the methyl, tert-butyl, benzyl ("Bn") and 9-fluorenylmethyl ("Fm") esters. Typically, this reaction is conducted using a base which effectively deprotonates the phenolic hydroxyl group, such as sodium carbonate, potassium carbonate, cesium carbonate, sodium hydride, sodium hydroxide, potassium hydroxide, sodium ethoxide, triethylamine, diisopropylethylamine and the like, in an inert diluent, such as tetrahydrofuran, N,N-dimethylformamide, N,N-dimethylacetamide, acetone, 2-butanone, 1-methyl-2-pyrrolidinone, water and the like, to provide protected intermediate 16.

Protected intermediate 16 is then deprotected using conventional procedures and reagents to afford carboxylic acid 17. For example, tert-butyl esters are readily hydrolyzed with 95% trifluoroacetic acid in dichloromethane; methyl ester can be hydrolyzed with lithium hydroxide in tetrahydrofuran/water; benzyl esters can be removed by hydrogenolysis in the presence of a catalyst, such as palladium on carbon; and 9-fluorenylmethyl esters are readily cleaved using 20% piperidine in DMF. If desired, other well-known protecting groups and deprotecting procedures may be employed in these reactions to form carboxylic acid intermediate 17 and related compounds.

Similarly, FIG. 11 illustrates the synthesis of a ligand precursor having an adapter with an amine functional group. In FIG. 11, ligand precursor 9 is coupled with adapter 18 (where "LG" is a leaving group, "PG" is a protecting group and n is typically an integer from 1 to about 20) to afford protected intermediate 19. As in FIG. 10, the leaving group employed in this reaction may be any conventional leaving group. Similarly, any conventional amine protecting group may be employed including, by way of example, trityl, tert-butoxycarbonyl ("Boc"), benzyloxycarbonyl ("CBZ") and 9-fluorenylmethoxy-carbonyl ("Fmoc"). After coupling the adapter 18 to ligand precursor 9, the resulting protected intermediate 19 is deprotected to afford ligand precursor 20 using conventional procedures and reagents. For example, a trityl group is readily removed using hydrogen chloride in acetone; a Boc group is removed using 95% trifluoroacetic acid in dichloromethane; a CBZ group can be removed by hydrogenolysis in the presence of a catalyst, such as palladium on carbon; and a 9-fluorenylmethoxycarbonyl group is readily cleaved using 20% piperidine in DMF to afford the deblocked amine. Other well-known amine protecting groups and deprotecting procedures may be employed in these reactions to form amine intermediate 20 and related compounds.

Figure 12:
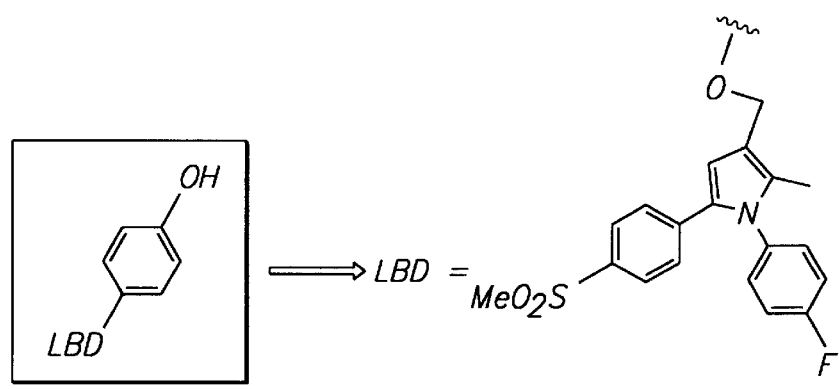
FIG. 12 and FIG. 13 illustrate dimer formation by coupling ligand precursors containing an adaptor.
Figure 12:
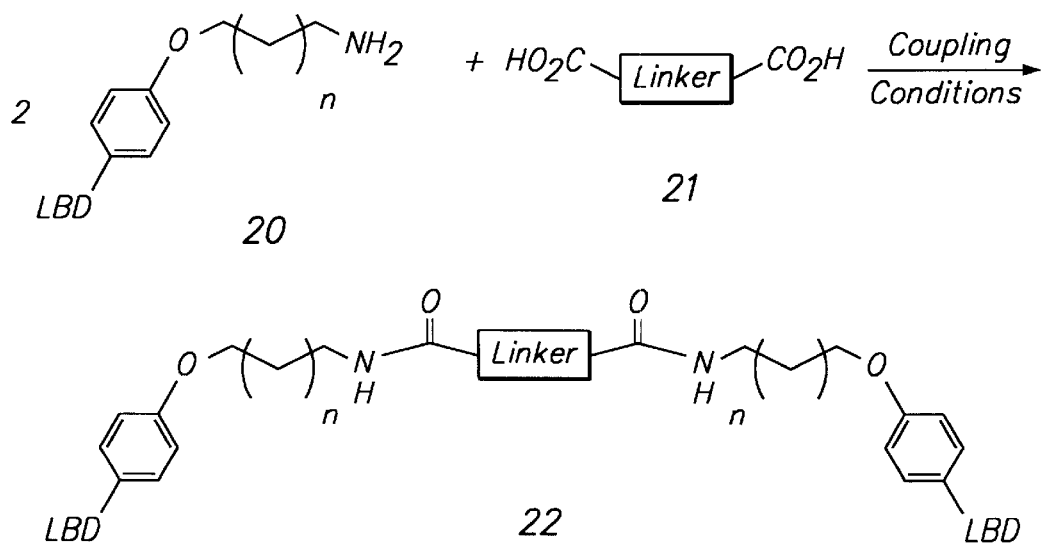
Figure 13:
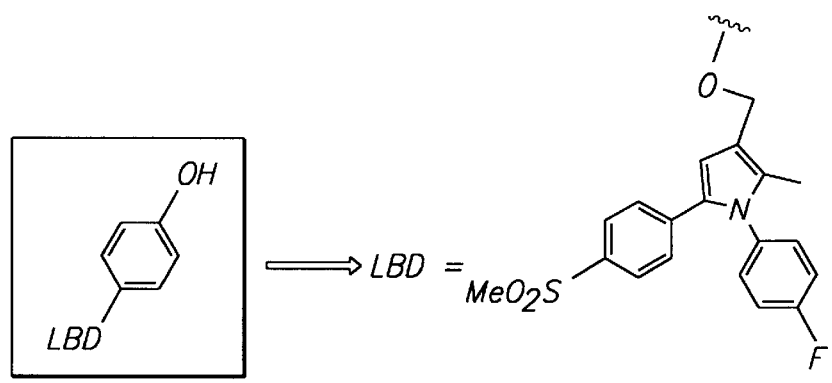
Figure 13:
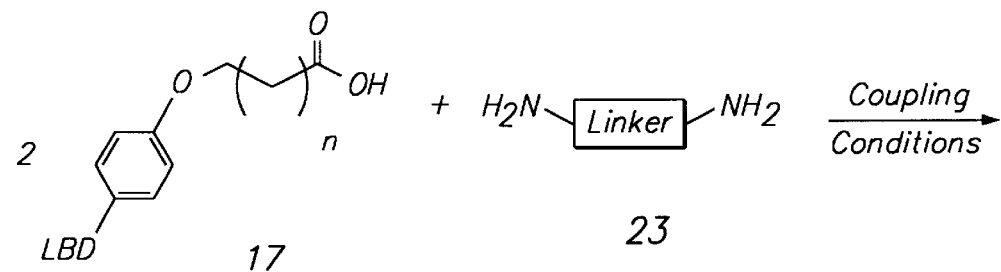
Figure 13:
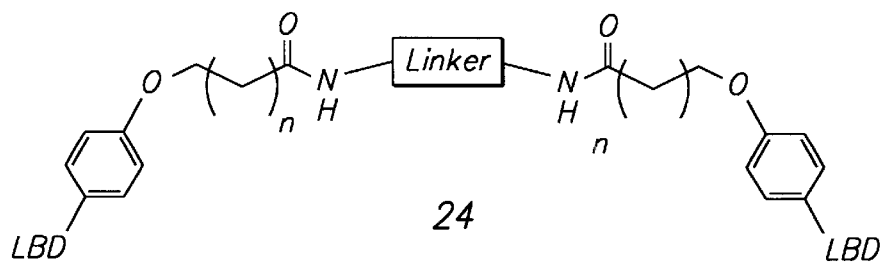

Ligand precursors having an adapter, such as the carboxylic acid intermediate 17 and the amine intermediate 20, can be readily coupled to intermediate linkers having complimentary functional groups to form multibinding compounds of this invention as illustrated in FIGS. 12 and 13. For example, in FIG. 12, amine intermediate 20 is coupled with bicarboxylic acid 21 to provide dimer 22. This reaction typically employs a conventional peptide coupling reagent and is conducted under conventional coupling reaction conditions, typically in the presence of a trialkylamine, such as ethyldiisopropylamine. Suitable coupling reagents for use in this reaction include, by way of example, carbodiimides, such as ethyl-3-(3-dimethylamino)propylcarbodiimide (EDC), dicyclohexylcarbodiimide (DCC), diisopropylcarbodiimide (DIC) and the like, and other well-known coupling reagents, such as N,N'-carbonyldiimidazole, 2-ethoxy-1-ethoxycarbonyl-1,2-dihydroquinoline (EEDQ), benzotriazol-1-yloxy-tris(dimethylamino)phosphonium hexafluorophosphate (BOP), O-(7-azabenzotriazol-1-yl)-N, N,N',N'-tetramethyluronium hexafluorophosphate (HATU) and the like. Optionally, well-known coupling promoters, such N-hydroxysuccinimide, 1-hydroxybenzotriazole (HOBT), 1-hydroxy-7-azabenzotriazole (HOAT), N,N-dimethylaminopyridine (DMAP) and the like, may be employed in this reaction. Typically, this coupling reaction is conducted at a temperature ranging from about 0° C. to about 60° C. for about 1 to about 72 hours in an inert diluent, such as THF, to afford dimer 22.

In a similar manner, ligand precursor 17 can be coupled to bis-amine 23 as shown in FIG. 13 to afford dimer 24. This reaction is typically conducted using the reagents and procedures described above for the preparation of dimer 22.

Figure 14:
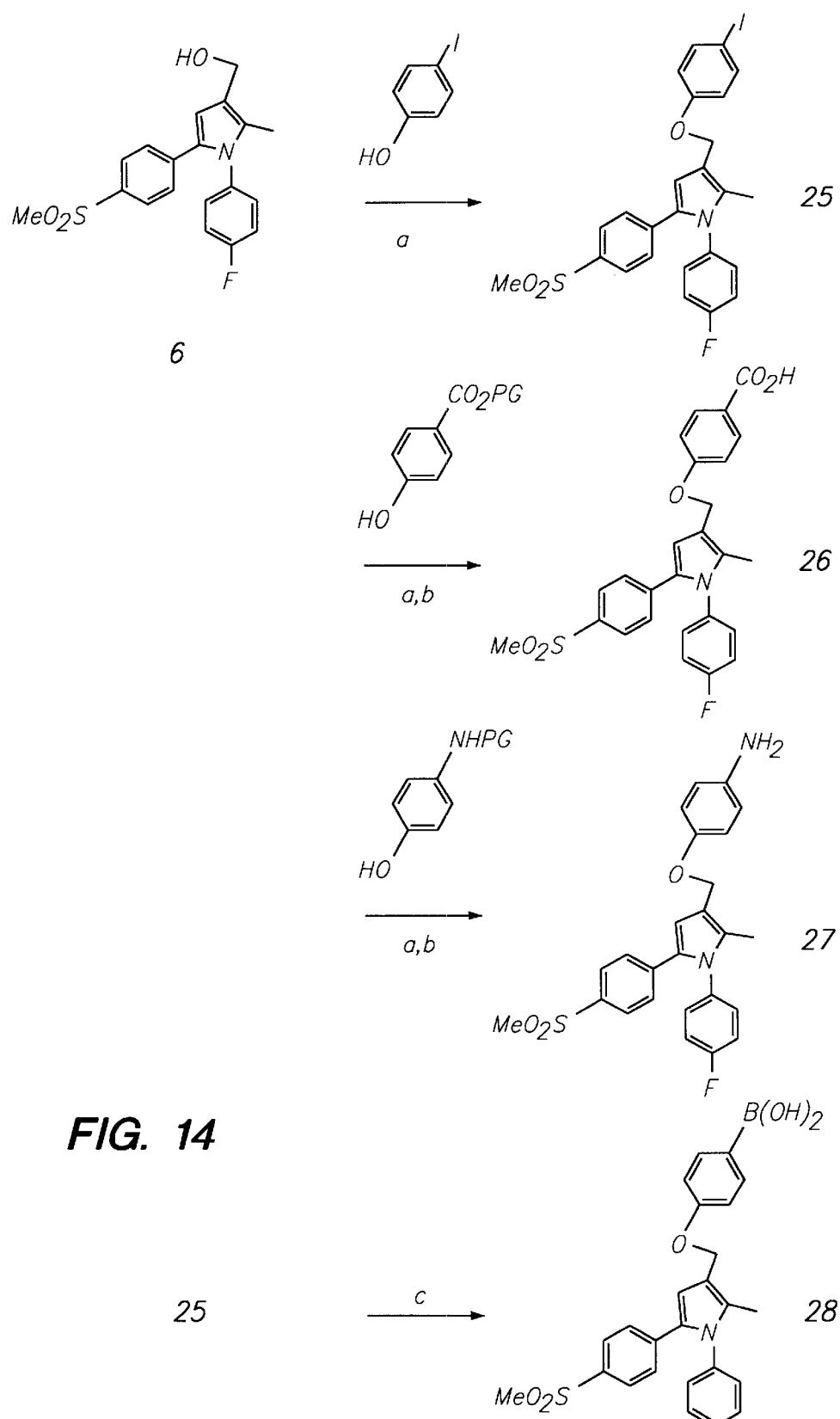
FIG. 14 illustrates the synthesis of ligand precursors having an aryl iodide, carboxylic acid, amine or boronic acid functional group.

The multibinding compound of this invention can also be prepared using a wide variety of other synthetic reactions and reagents. For example, FIG. 14 illustrates the synthesis of ligand precursors having aryliodide, carboxylic acid, amine and boronic acid functional groups. As shown in FIG. 14, hydroxymethyl pyrrole 6 (prepared as described herein) can be readily coupled under Mitsunobu reaction conditions to various phenols to provide, after deprotection, functionalized intermediates 25–28. The Mitsunobu reaction is typically conducted by reacting 6 and the appropriate phenol using diethyl azodicarboxylate (DEAD) and triphenylphosphine at ambient temperature for about 48 hours. Deprotection, if necessary, using conventional procedures and reagents then affords the functionalized intermediates 25–28.

Figure 15:
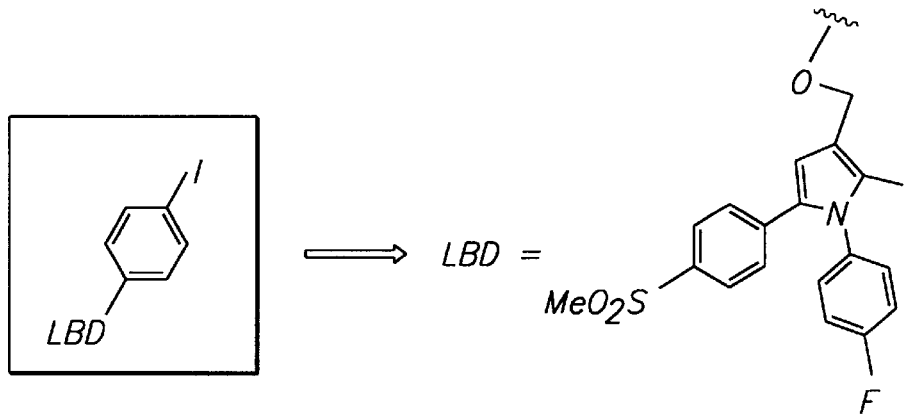
FIG. 15, FIG. 16, FIG. 17 and FIG. 18 illustrate dimer formation via carbon-carbon bond formation.
Figure 15:
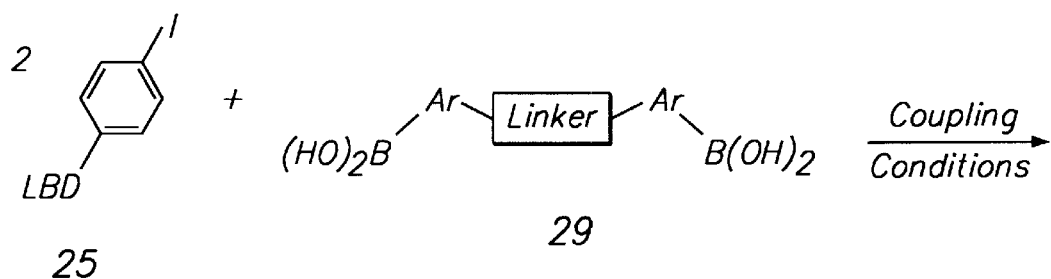
Figure 15:
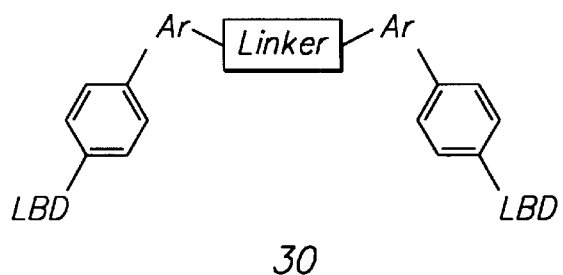
Figure 16:
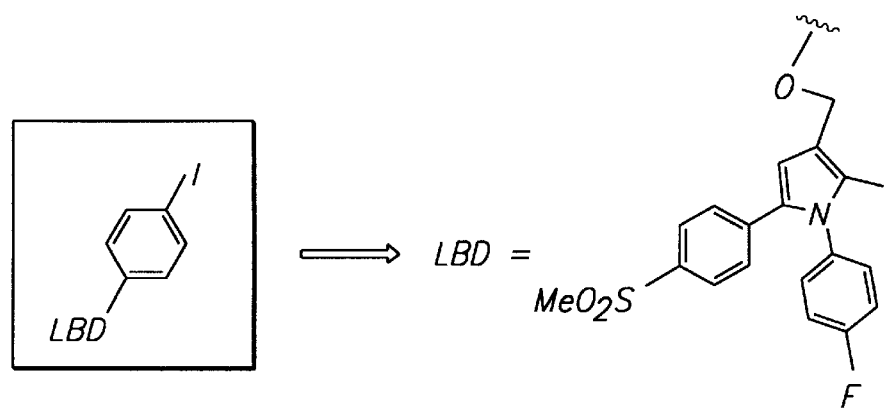
Figure 16:
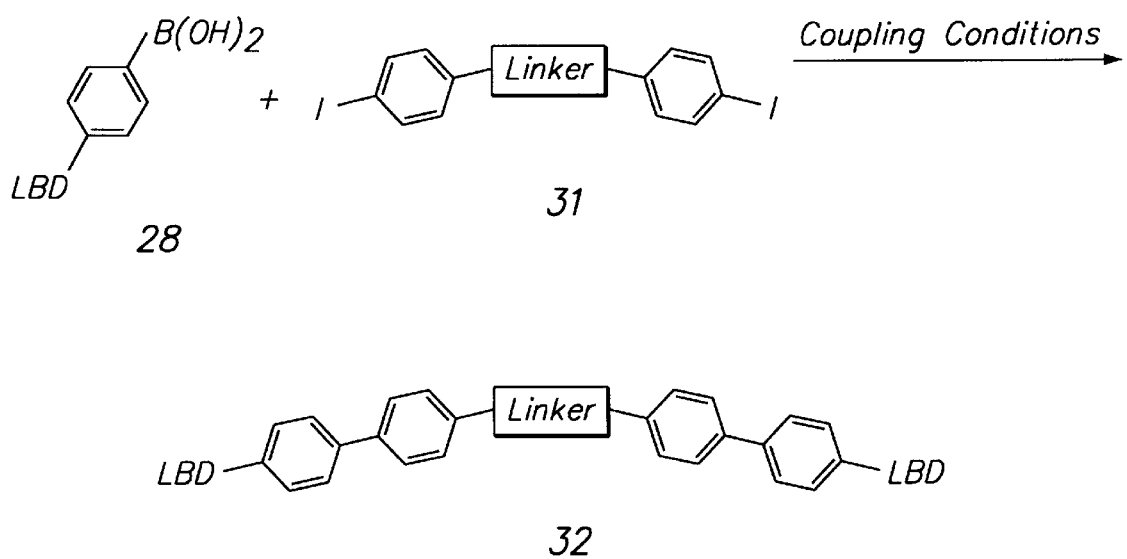

The functionalized intermediates prepared as shown in FIG. 14 can be employed in the synthesis of multibinding compounds of this invention. For example, FIG. 15 illustrates the coupling of aryliodide intermediate 25 with a bis-boronic acid linker, 29, to provide dimer 30. Typically, this reaction is conducted by contacting two molar equivalents of 25 and one molar equivalent of 29 in the presence of tetrakis(triphenylphosphine)palladium(0), sodium carbonate and water in refluxing toluene. Using similar reaction conditions, boronic acid intermediate 28 can be coupled with bis-aryliodide 31 to provide dimer 32 as shown in FIG. 16.

Figure 17:
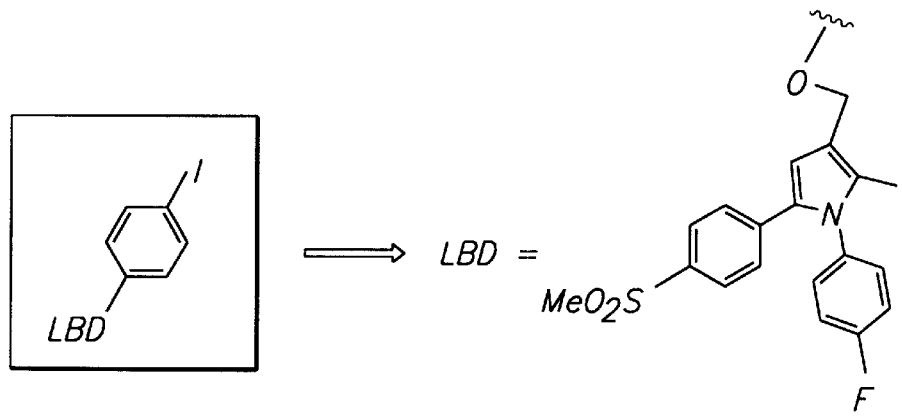
Figure 17:
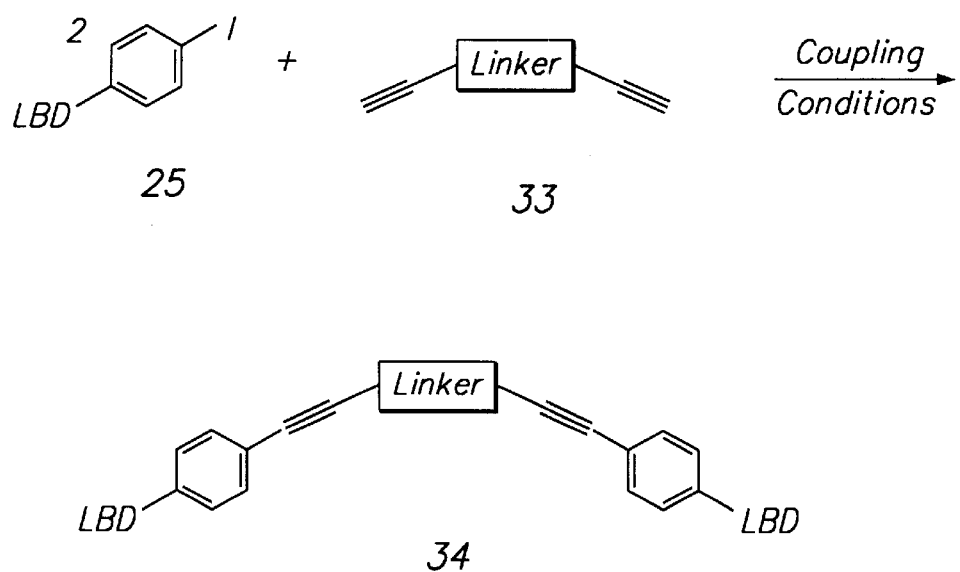
Figure 18:
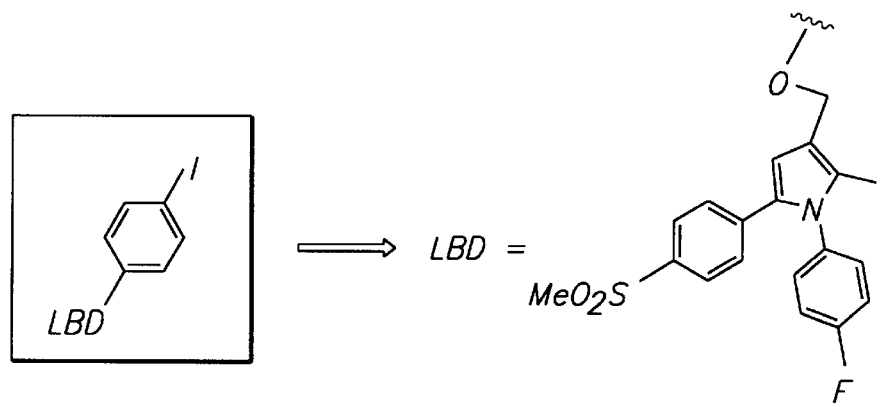
Figure 18:
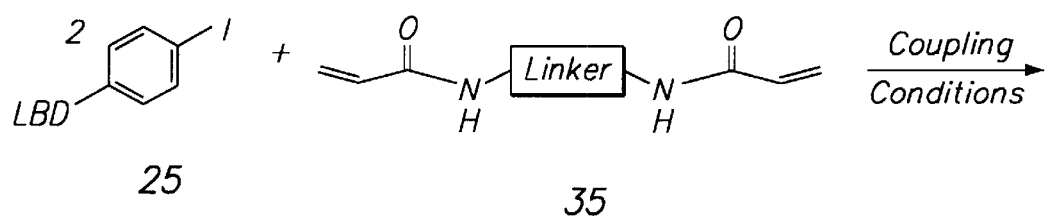
Figure 18:
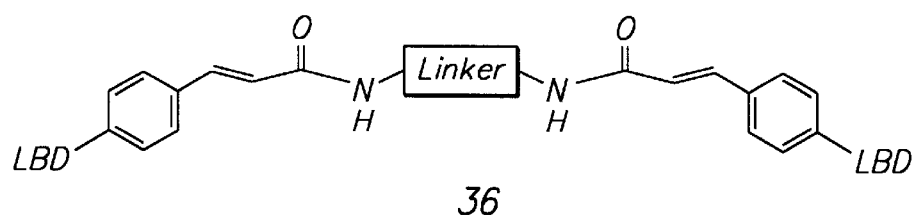

Aryliodide intermediate 25 can also be coupled with acrylate intermediate 33 or alkyne intermediate 35 to afford dimers 34 and 36 as shown in FIG. 17 and FIG. 18. These reactions are typically conducted by contacting two molar equivalents of aryliodide intermediate 25 with one molar equivalent of either 33 or 34 in the presence of dichlorobis (triphenylphosphine)palladium (II), copper (I) iodide and diisopropylethylamine in N,N-dimethylfomamide to afford 34 and 36, respectively.

As will be readily apparent to those of ordinary skill in the art, the synthetic procedures described herein or those known in the art may be readily modified to afford a wide variety of compounds within the scope of this invention.

Combinatorial Libraries

The methods described herein lend themselves to combinatorial approaches for identifying multimeric compounds which possess multibinding properties.

Specifically, factors such as the proper juxtaposition of the individual ligands of a multibinding compound with respect to the relevant array of binding sites on a target or targets is important in optimizing the interaction of the multibinding compound with its target(s) and to maximize the biological advantage through multivalency. One approach is to identify a library of candidate multibinding compounds with properties spanning the multibinding parameters that are relevant for a particular target. These parameters include: (1) the identity of ligand(s), (2) the orientation of ligands, (3) the valency of the construct, (4) linker length, (5) linker geometry, (6) linker physical properties, and (7) linker chemical functional groups.

Libraries of multimeric compounds potentially possessing multibinding properties (i.e., candidate multibinding compounds) and comprising a multiplicity of such variables are prepared and these libraries are then evaluated via conventional assays corresponding to the ligand selected and the multibinding parameters desired. Considerations relevant to each of these variables are set forth below:

Selection of Ligand(s)

A single ligand or set of ligands is (are) selected for incorporation into the libraries of candidate multibinding compounds which library is directed against a particular biological target or targets, i.e., inhibition of COX-2. The only requirement for the ligands chosen is that they are capable of interacting with the selected target(s). Thus, ligands may be known drugs, modified forms of known drugs, substructures of known drugs or substrates of modified forms of known drugs (which are competent to interact with the target), or other compounds. Ligands are preferably chosen based on known favorable properties that may be projected to be carried over to or amplified in multibinding forms. Favorable properties include demonstrated safety and efficacy in human patients, appropriate PK/ADME profiles, synthetic accessibility, and desirable physical properties such as solubility, logP, etc. However, it is crucial to note that ligands which display an unfavorable property from among the previous list may obtain a more favorable property through the process of multibinding compound formation; i.e., ligands should not necessarily be excluded on such a basis. For example, a ligand that is not sufficiently potent at a particular target so as to be efficacious in a human patient may become highly potent and efficacious when presented in multibinding form. A ligand that is potent and efficacious but not of utility because of a non-mechanism-related toxic side effect may have increased therapeutic index (increased potency relative to toxicity) as a multibinding compound. Compounds that exhibit short in vivo half-lives may have extended half-lives as multibinding compounds. Physical properties of ligands that limit their usefulness (e.g. poor bioavailability due to low solubility, hydrophobicity, hydrophilicity) may be rationally modulated in multibinding forms, providing compounds with physical properties consistent with the desired utility.

Orientation: Selection of Ligand Attachment Points and Linking Chemistry

Several points are chosen on each ligand at which to attach the ligand to the linker. The selected points on the ligand/linker for attachment are functionalized to contain complementary reactive functional groups. This permits probing the effects of presenting the ligands to their target binding site(s) in multiple relative orientations, an important multibinding design parameter. The only requirement for choosing attachment points is that attaching to at least one of these points does not abrogate activity of the ligand. Such points for attachment can be identified by structural information when available. For example, inspection of a co-crystal structure of a ligand bound to its target allows one to identify one or more sites where linker attachment will not preclude the ligand/target interaction. Alternatively, evaluation of ligand/target binding by nuclear magnetic resonance will permit the identification of sites non-essential for ligand/target binding. See, for example, Fesik, et al., U.S. Pat. No. 5,891,643, the disclosure of which is incorporated herein by reference in its entirety. When such structural information is not available, utilization of structure-activity relationships (SAR) for ligands will suggest positions where substantial structural variations are and are not allowed. In the absence of both structural and SAR information, a library is merely selected with multiple points of attachment to allow presentation of the ligand in multiple distinct orientations. Subsequent evaluation of this library will indicate what positions are suitable for attachment.

It is important to emphasize that positions of attachment that do abrogate the activity of the monomeric ligand may also be advantageously included in candidate multibinding compounds in the library provided that such compounds bear at least one ligand attached in a manner which does not abrogate intrinsic activity. This selection derives from, for example, heterobivalent interactions within the context of a single target molecule. For example, consider a ligand bound to its target, and then consider modifying this ligand by attaching to it a second copy of the same ligand with a linker which allows the second ligand to interact with the same target at sites proximal to the first binding site, which include elements of the target that are not part of the formal ligand binding site and/or elements of the matrix surrounding the formal binding site, such as the membrane. Here, the most favorable orientation for interaction of the second ligand molecule may be achieved by attaching it to the linker at a position which abrogates activity of the ligand at the first binding site. Another way to consider this is that the SAR of individual ligands within the context of a multibinding structure is often different from the SAR of those same ligands in momomeric form.

The foregoing discussion focused on bivalent interactions of dimeric compounds bearing two copies of the same ligand joined to a single linker through different attachment points, one of which may abrogate the binding/activity of the monomeric ligand. It should also be understood that bivalent advantage may also be attained with heterodimeric constructs bearing two different ligands that bind to common or different targets.

Once the ligand attachment points have been chosen, one identifies the types of chemical linkages that are possible at those points. The most preferred types of chemical linkages are those that are compatible with the overall structure of the ligand (or protected forms of the ligand) readily and generally formed, stable and intrinsically innocuous under typical chemical and physiological conditions, and compatible with a large number of available linkers. Amide bonds, ethers, amines, carbamates, ureas, and sulfonamides are but a few examples of preferred linkages.

Linker Selection

In the library of linkers employed to generate the library of candidate multibinding compounds, the selection of linkers employed in this library of linkers takes into consideration the following factors:

Valency: In most instances the library of linkers is initiated with divalent linkers. The choice of ligands and proper juxtaposition of two ligands relative to their binding sites permits such molecules to exhibit target binding affinities and specificities more than sufficient to confer biological advantage. Furthermore, divalent linkers or constructs are also typically of modest size such that they retain the desirable biodistribution properties of small molecules.

Linker Length: Linkers are chosen in a range of lengths to allow the spanning of a range of inter-ligand distances that encompass the distance preferable for a given divalent interaction. In some instances the preferred distance can be estimated rather precisely from high-resolution structural information of targets. In other instances where high-resolution structural information is not available, one can make use of simple models to estimate the maximum distance between binding sites either on adjacent receptors or at different locations on the same receptor. In situations where two binding sites are present on the same target (or target subunit for multisubunit targets), preferred linker distances are 2–20 Å, with more preferred linker distances of 3–12 Å. In situations where two binding sites reside on separate target sites, preferred linker distances are 20–100 Å, with more preferred distances of 30–70 Å.

Linker Geometry and Rigidity: The combination of ligand attachment site, linker length, linker geometry, and linker rigidity determine the possible ways in which the ligands of candidate multibinding compounds may be displayed in three dimensions and thereby presented to their binding sites. Linker geometry and rigidity are nominally determined by chemical composition and bonding pattern, which may be controlled and are systematically varied as another spanning function in a multibinding array. For example, linker geometry is varied by attaching two ligands to the ortho, meta, and para positions of a benzene ring, or in cis- or trans-arrangements at the 1,1- vs. 1,2- vs. 1,3- vs. 1,4- positions around a cyclohexane core or in cis- or trans-arrangements at a point of ethylene unsaturation. Linker rigidity is varied by controlling the number and relative energies of different conformational states possible for the linker. For example, a divalent compound bearing two ligands joined by 1,8-octyl linker has many more degrees of freedom, and is therefore less rigid than a compound in which the two ligands are attached to the 4,4' positions of a biphenyl linker.

Linker Physical Properties: The physical properties of linkers are nominally determined by the chemical constitution and bonding patterns of the linker, and linker physical properties impact the overall physical properties of the candidate multibinding compounds in which they are included. A range of linker compositions is typically selected to provide a range of physical properties (hydrophobicity, hydrophilicity, amphiphilicity, polarization, acidity, and basicity) in the candidate multibinding compounds. The particular choice of linker physical properties is made within the context of the physical properties of the ligands they join and preferably the goal is to generate molecules with favorable PK/ADME properties. For example, linkers can be selected to avoid those that are too hydrophilic or too hydrophobic to be readily absorbed and/or distributed in vivo.

Linker Chemical Functional Groups: Linker chemical functional groups are selected to be compatible with the chemistry chosen to connect linkers to the ligands and to impart the range of physical properties sufficient to span initial examination of this parameter.

Combinatorial Synthesis

Having chosen a set of n ligands (n being determined by the sum of the number of different attachment points for each ligand chosen) and m linkers by the process outlined above, a library of (n!)m candidate divalent multibinding compounds is prepared which spans the relevant multibinding design parameters or a particular target. For example, an array generated from two ligands, one which has two attachment points (A1, A2) and one which has three attachment points (B1, B2, B3) joined in all possible combinations provide for at least 15 possible combinations of multibinding compounds:

| A1-A1 | A1-A2 | A1-B1 | A1-B2 | A1-B3 | A2-A2 | A2-B1 | A2-B2 |
| A2-B3 | B1-B1 | B1-B2 | B1-B3 | B2-B2 | B2-B3 | B3-B3 | |

When each of these combinations is joined by 10 different linkers, a library of 150 candidate multibinding compounds results.

Given the combinatorial nature of the library, common chemistries are preferably used to join the reactive functionalies on the ligands with complementary reactive functionalities on the linkers. The library therefore lends itself to efficient parallel synthetic methods. The combinatorial library can employ solid phase chemistries well known in the art wherein the ligand and/or linker is attached to a solid support. Alternatively and preferably, the combinatorial libary is prepared in the solution phase. After synthesis, candidate multibinding compounds are optionally purified before assaying for activity by, for example, chromatographic methods (e.g., HPLC).

Analysis of the Library

Various methods are used to characterize the properties and activities of the candidate multibinding compounds in the library to determine which compounds possess multibinding properties. Physical constants such as solubility under various solvent conditions and logD/clogD values are determined. A combination of NMR spectroscopy and computational methods is used to determine low-energy conformations of the candidate multibinding compounds in fluid media. The ability of the members of the library to bind to the desired target and other targets is determined by various standard methods, which include radioligand displacement assays for receptor and ion channel targets, and kinetic inhibition analysis for many enzyme targets. In vitro efficacy, such as for receptor agonists and antagonists, ion channel blockers, and antimicrobial activity, are also determined. Pharmacological data, including oral absorption, everted gut penetration, other pharmacokinetic parameters and efficacy data are determined in appropriate models. In this way, key structure-activity relationships are obtained for multibinding design parameters which are then used to direct future work.

The members of the library which exhibit multibinding properties, as defined herein, can be readily determined by conventional methods. First those members which exhibit multibinding properties are identified by conventional methods as described above including conventional assays (both in vitro and in vivo).

Second, ascertaining the structure of those compounds which exhibit multibinding properties can be accomplished via art recognized procedures. For example, each member of the library can be encrypted or tagged with appropriate information allowing determination of the structure of relevant members at a later time. See, for example, Dower, et al., International Patent Application Publication No. WO 93/06121; Brenner, et al., Proc. Natl. Acad. Sci., USA, 89:5181 (1992); Gallop, et al., U.S. Pat. No. 5,846,839; each of which are incorporated herein by reference in its entirety. Alternatively, the structure of relevant multivalent compounds can also be determined from soluble and untagged libaries of candidate multivalent compounds by methods known in the art such as those described by Hindsgaul, et al., Canadian Patent Application No. 2,240,325 which was published on Jul. 11, 1998. Such methods couple frontal affinity chromatography with mass spectroscopy to determine both the structure and relative binding affinities of candidate multibinding compounds to receptors.

The process set forth above for dimeric candidate multibinding compounds can, of course, be extended to trimeric candidate compounds and higher analogs thereof.

Follow-up Synthesis and Analysis of Additional Libraries

Based on the information obtained through analysis of the initial library, an optional component of the process is to ascertain one or more promising multibinding "lead" compounds as defined by particular relative ligand orientations, linker lengths, linker geometries, etc. Additional libraries can then be generated around these leads to provide for further information regarding structure to activity relationships. These arrays typically bear more focused variations in linker structure in an effort to further optimize target affinity and/or activity at the target (antagonism, partial agonism, etc.), and/or alter physical properties. By iterative redesign/analysis using the novel principles of multibinding design along with classical medicinal chemistry, biochemistry, and pharmacology approaches, one is able to prepare and identify optimal multibinding compounds that exhibit biological advantage towards their targets and as therapeutic agents.

To further elaborate upon this procedure, suitable divalent linkers include, by way of example only, those derived from dicarboxylic acids, disulfonylhalides, dialdehydes, diketones, dihalides, diisocyanates, diamines, diols, mixtures of carboxylic acids, sulfonylhalides, aldehydes, ketones, halides, isocyanates, amines and diols. In each case, the carboxylic acid, sulfonylhalide, aldehyde, ketone, halide, isocyanate, amine and diol functional group is reacted with a complementary functionality on the ligand to form a covalent linkage. Such complementary functionality is well known in the art as illustrated in the following table:

| Representative Complementary Binding Chemistries | | |
|---|---|---|
| First Reactive Group | Second Reactive Group | Linkage |
| hydroxyl | isocyanate | urethane |
| amine | epoxide | β-hydroxyamine |
| sulfonyl halide | amine | sulfonamide |
| carboxyl acid | amine | amide |
| hydroxyl | alkyl/aryl halide | ether |
| aldehyde | amine(+reducing agent) | amine |
| ketone | amine(+reducing agent) | amine |
| amine | isocyanate | carbamate |

Exemplary linkers include the following linkers identified as X-1 through X-418 as set forth below:

Diacids

X-1
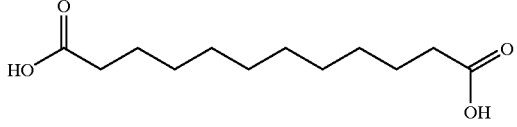

X-2
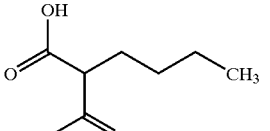

X-3
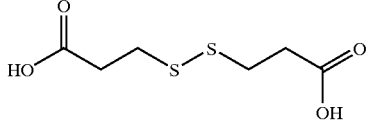

X-4
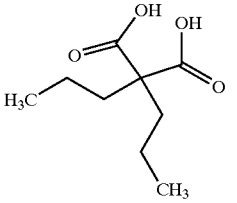

X-5
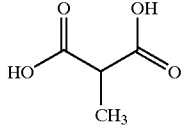

X-6
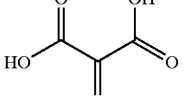

X-7
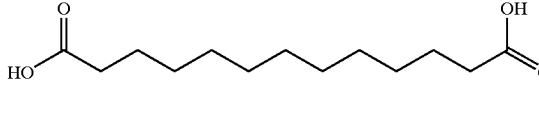

X-8
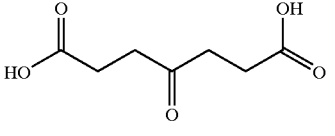

X-9
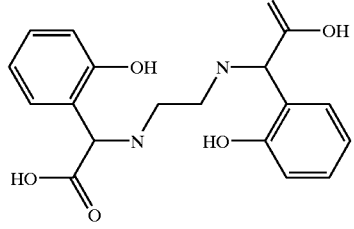

X-10
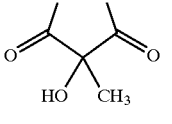

X-11
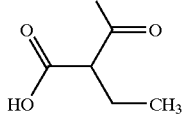

X-12
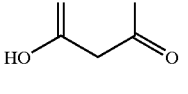

X-13
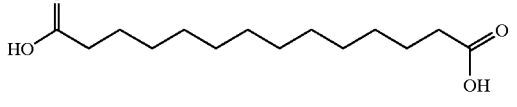

X-14
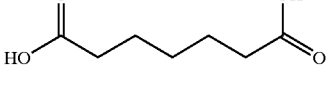

-continued
X-15
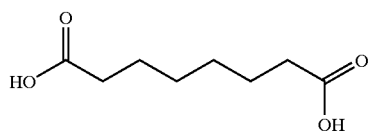
X-16
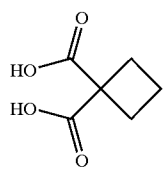
X-17
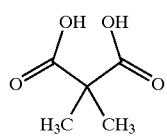
X-18
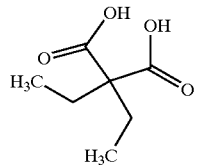
X-19
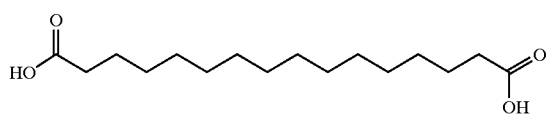
X-20
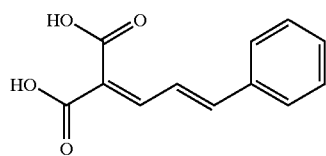
X-21
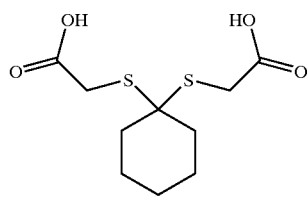
X-22
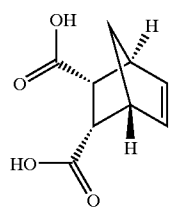
X-23
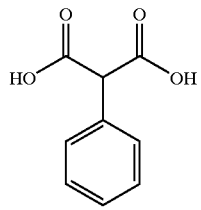
X-24
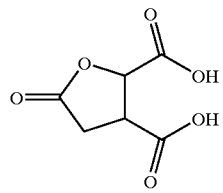
X-25
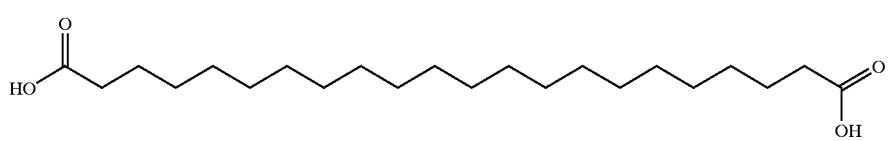
X-26
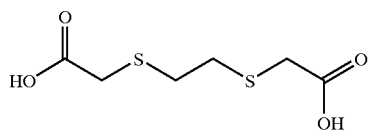
X-27
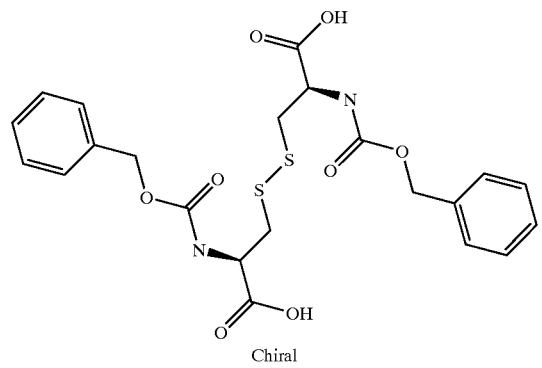
Chiral -continued
X-28
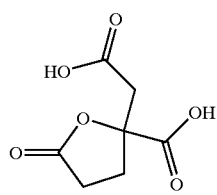
X-29
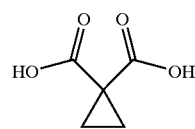
X-30
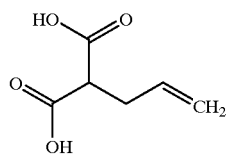
X-31
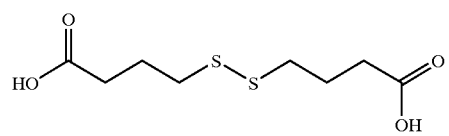
X-32
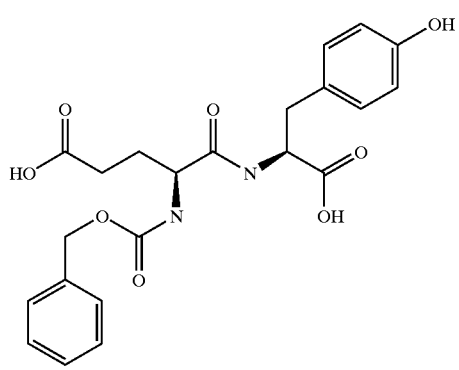
Chiral
X-33
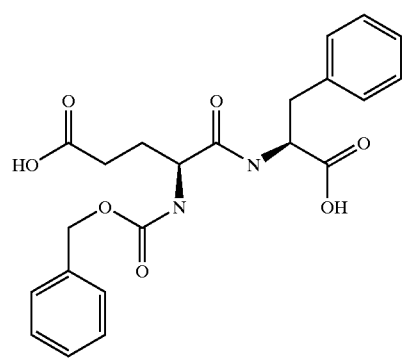
Chiral
X-34
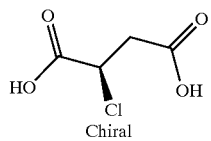
Chiral
X-35
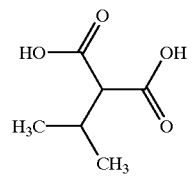
X-36
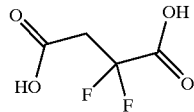
X-37
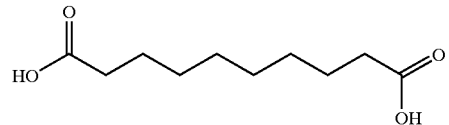
X-38
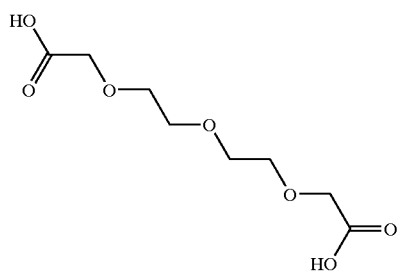
X-39
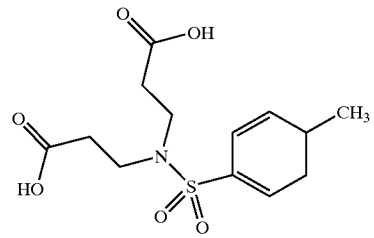

X-40
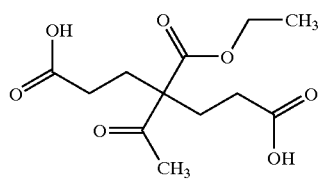
X-41
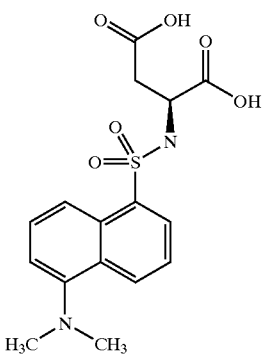
Chiral
X-42
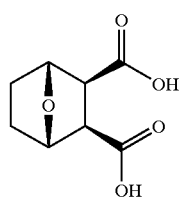
X-43
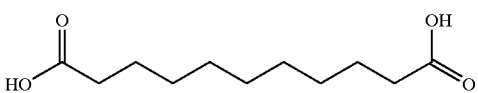
X-44
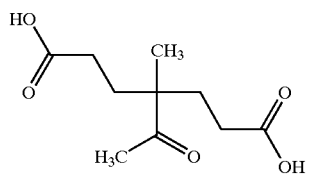
X-45
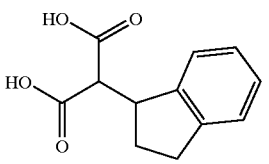
X-46
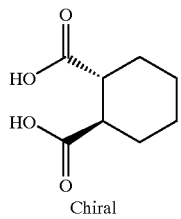
Chiral
X-47
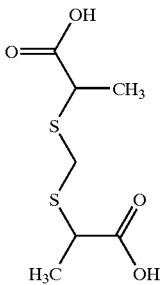
X-48
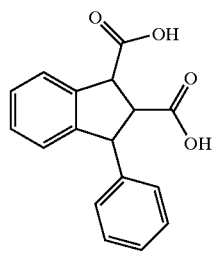
X-49
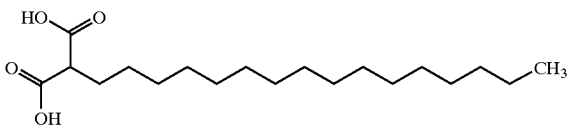
X-50
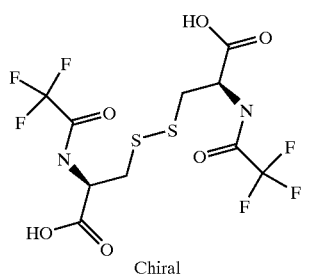
Chiral
X-51
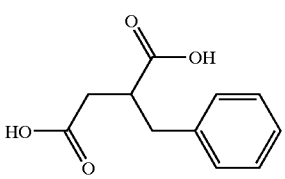

-continued
X-52
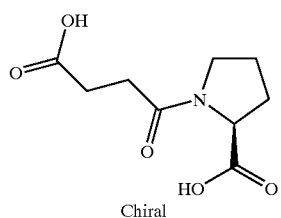
Chiral
X-53
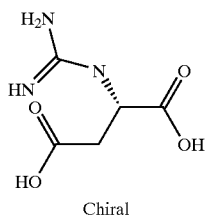
Chiral
X-54
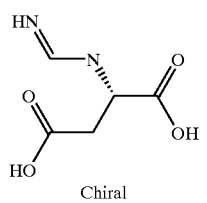
Chiral
X-55
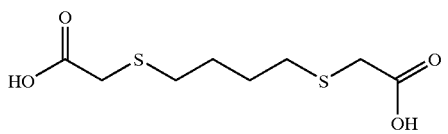
X-56
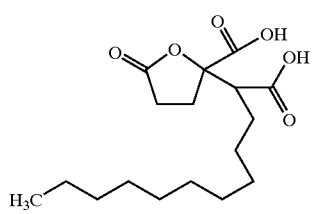
X-57
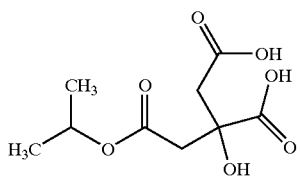
X-58
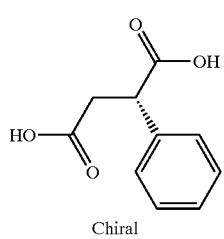
Chiral
X-59
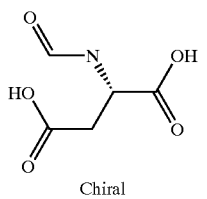
Chiral
X-60
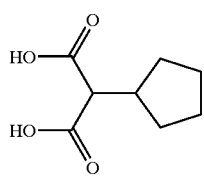
X-61
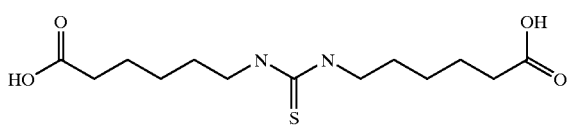
X-62
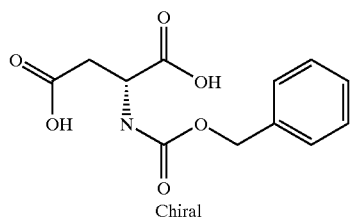
Chiral
X-63
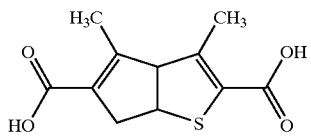
X-64
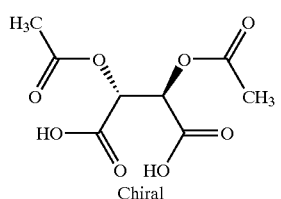
Chiral
X-65
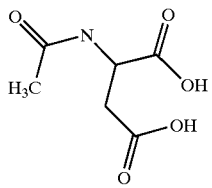

-continued
X-66
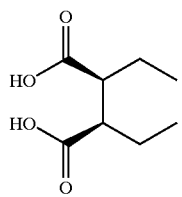
X-67
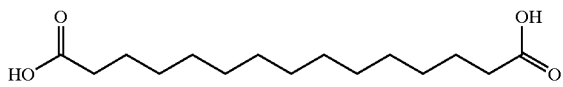
X-68
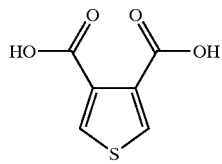
X-69
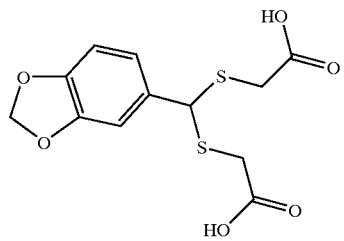
X-70
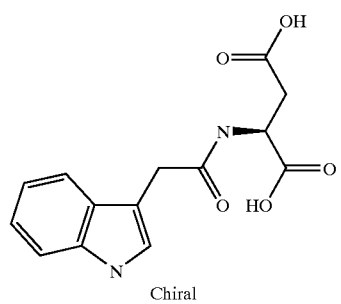
Chiral
X-71
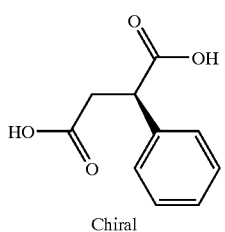
Chiral
X-72
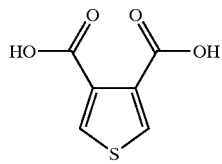
X-73
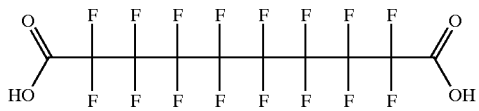
X-74
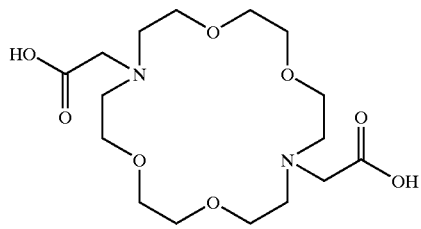
X-75
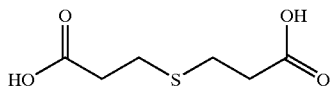
X-76
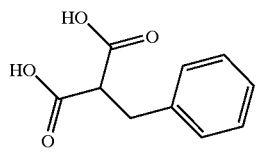
X-77
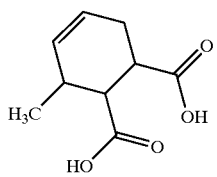
X-78
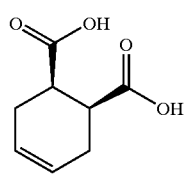

-continued
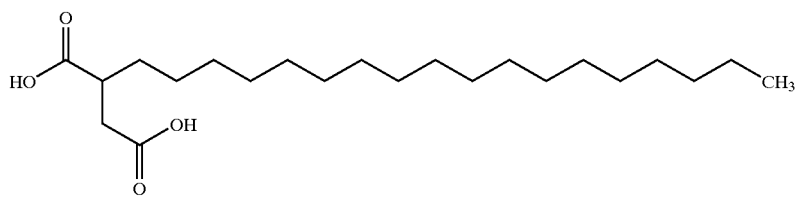
X-79
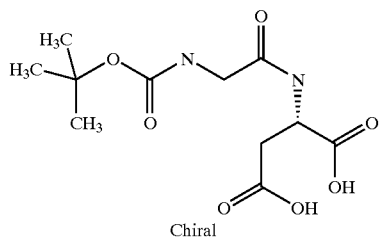
X-80
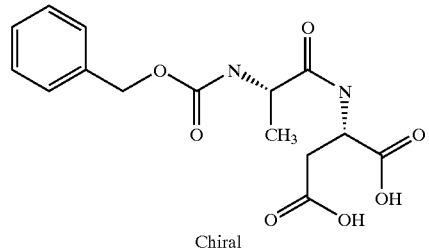
X-81
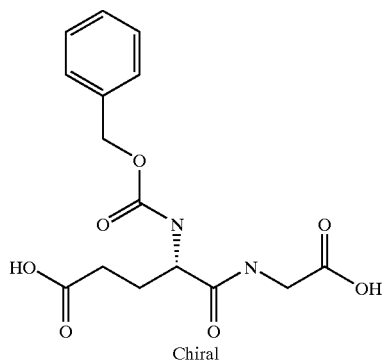
X-82
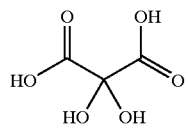
X-83
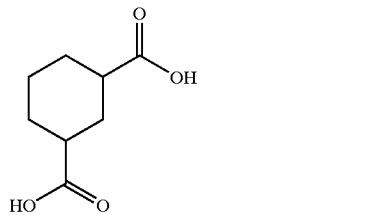
X-84
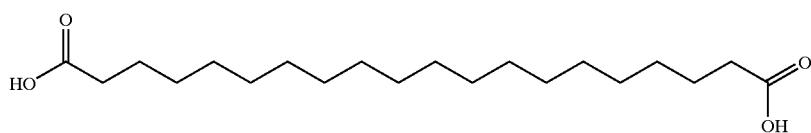
X-85
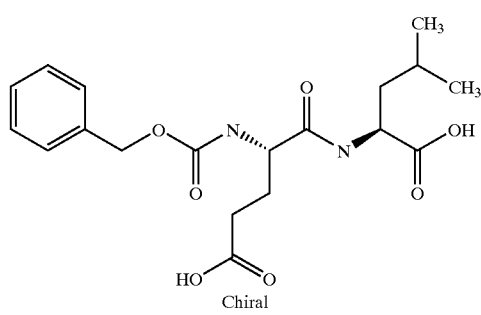
X-86
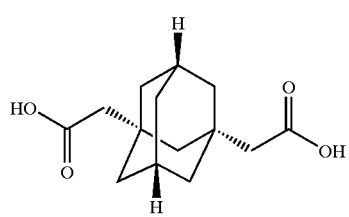
X-87

-continued
X-88 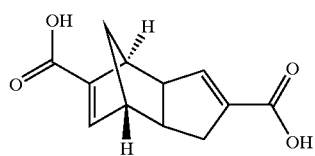
X-89 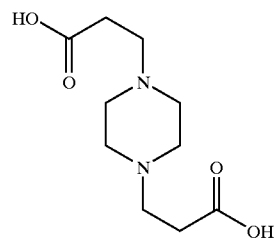
X-90 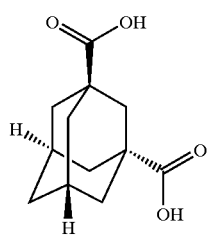
X-91 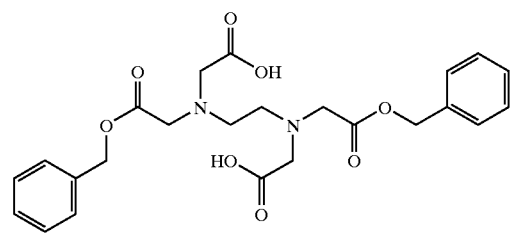
X-92 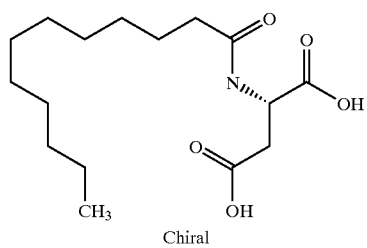
X-93 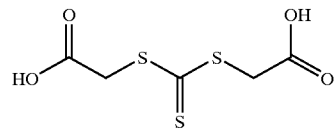
X-94 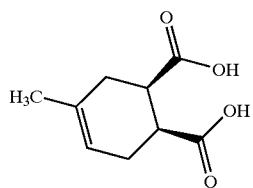
X-95 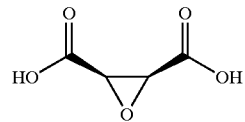
X-96 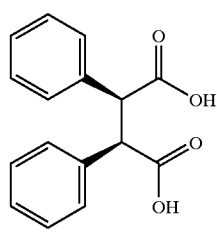
X-97 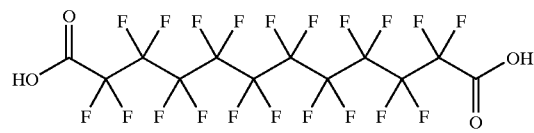
X-98 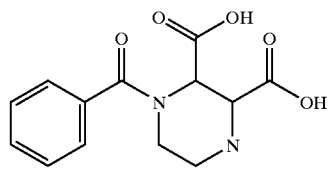
X-99 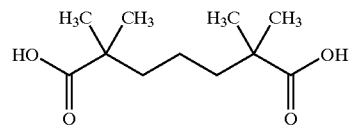
X-100 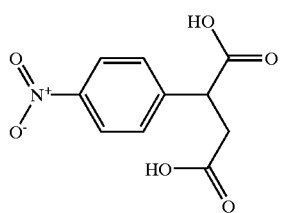
X-101 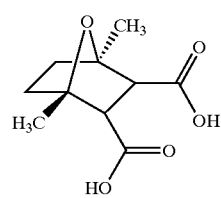

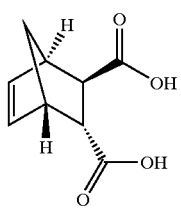
X-102
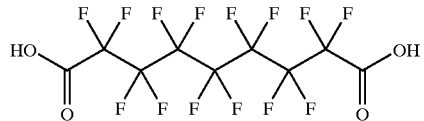
X-103
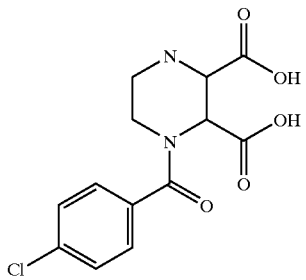
X-104
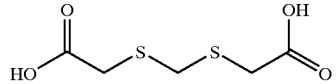
X-105
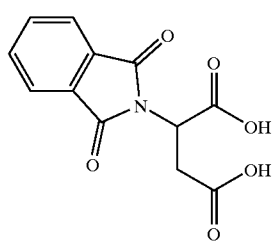
X-106
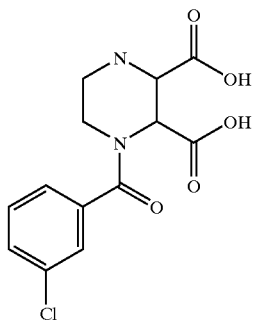
X-107
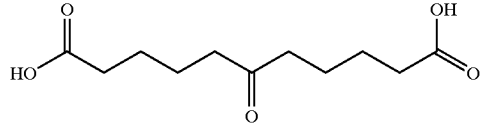
X-108
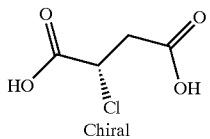
X-109
X-110
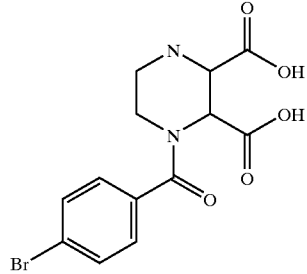
X-111

-continued
X-116
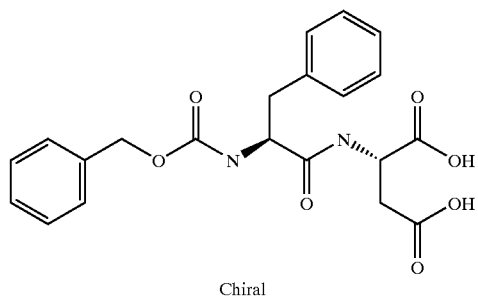
Chiral
X-117
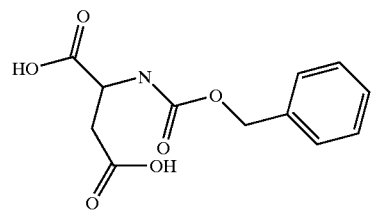
X-118
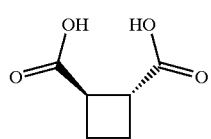
X-119
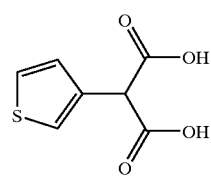
X-120
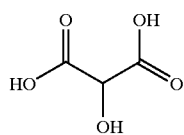
X-121
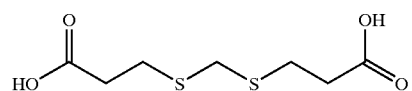
X-122
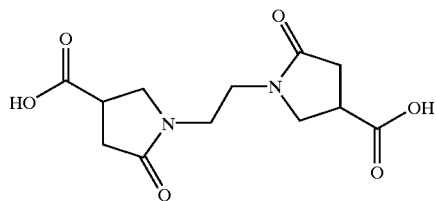
X-123
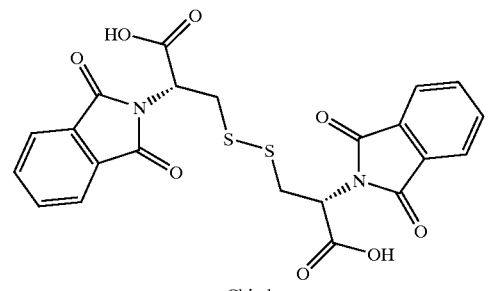
Chiral
X-124
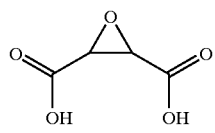
X-125
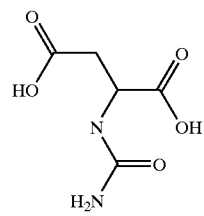
X-126
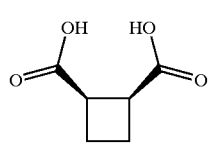
X-127
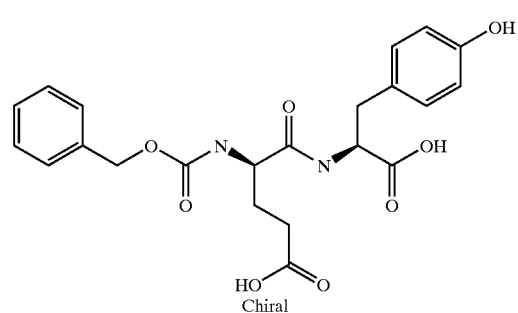
Chiral
X-128
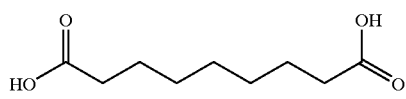
X-129
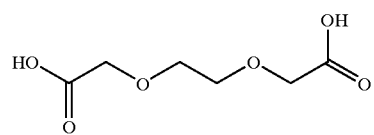

X-130 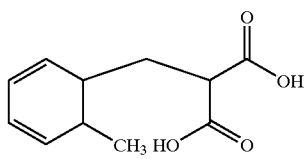
X-131 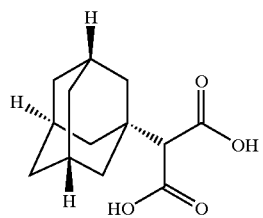
X-132 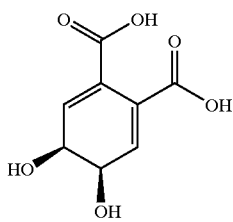
Disulfonyl Halides
X-133 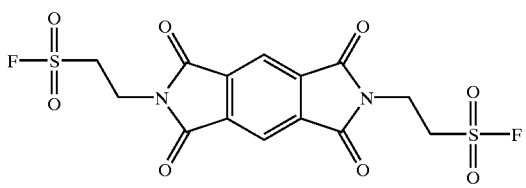
X-134 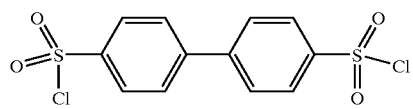
X-135 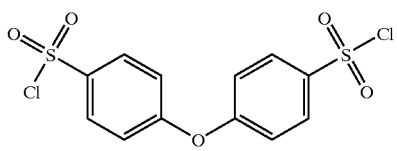
X-136 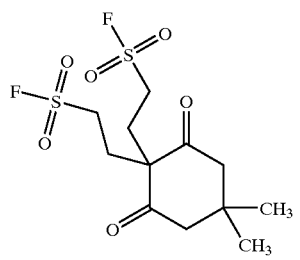
X-137 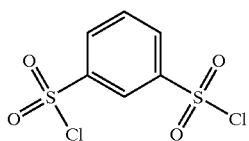
X-138 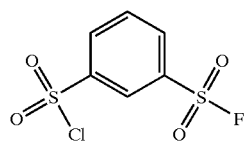
X-139 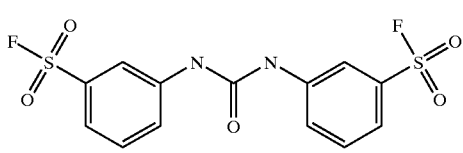
X-140 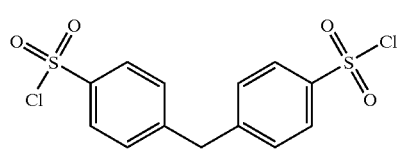
X-141 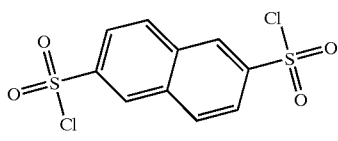
X-142 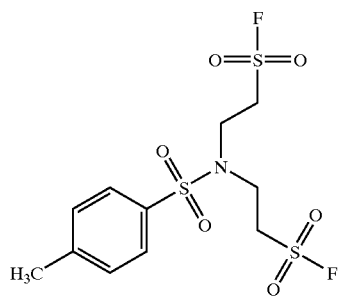

-continued

| X-143 | X-144 |
| X-145 | X-146 |
| X-147 | X-148 |
| X-149 | X-150 |
| X-151 | X-152 |

Dialdehydes

| X-153 | X-154 |
| X-155 | X-156 |

-continued
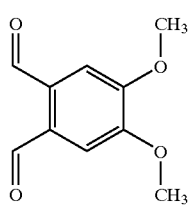
X-157
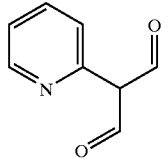
X-158
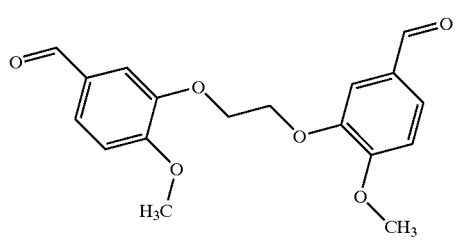
X-159
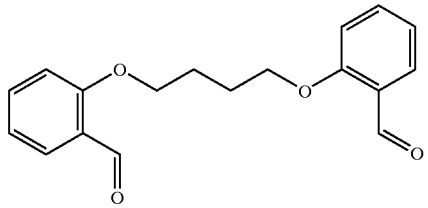
X-160
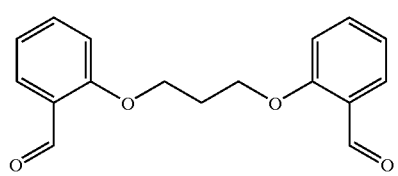
X-161
X-162
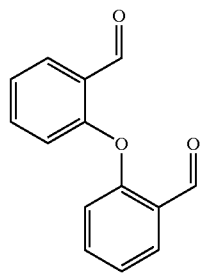
X-163
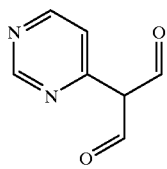
X-164
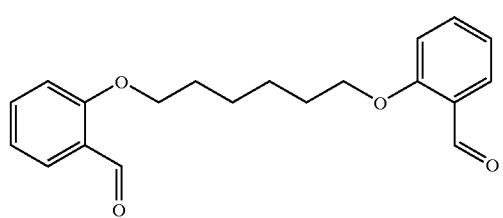
X-165
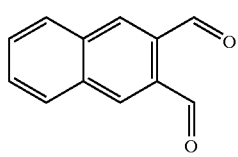
X-166
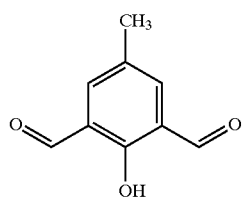
X-167
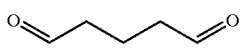
X-168
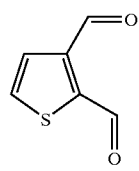
X-169
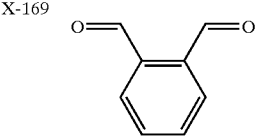
X-170

-continued
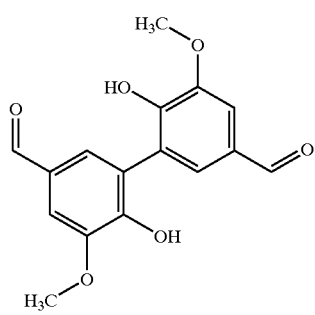 X-171
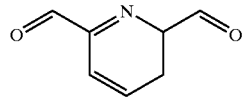 X-172
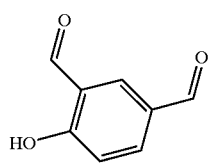 X-173
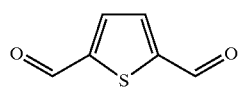 X-174
Dihalides
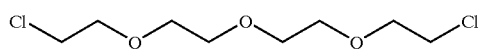 X-175
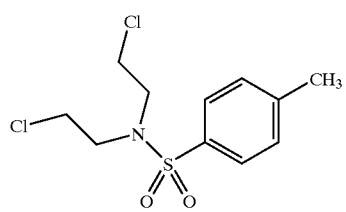 X-176
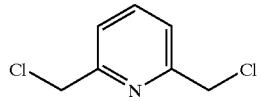 X-177
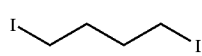 X-178
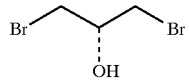 X-179
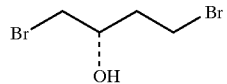 X-180
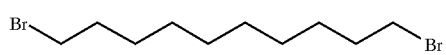 X-181
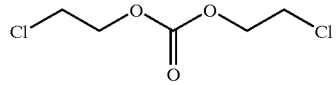 X-182
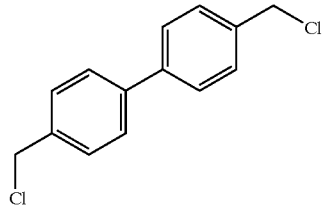 X-183
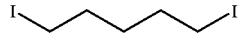 X-184
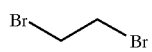 X-185
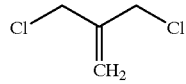 X-186
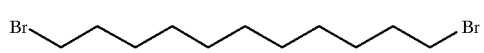 X-187
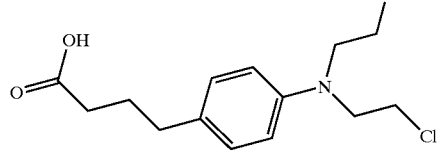 X-188

-continued
X-189 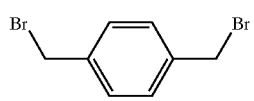 X-190 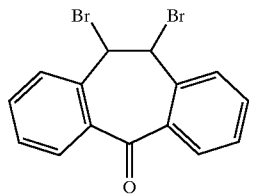
X-191 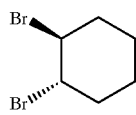 I~~~I X-192
X-193 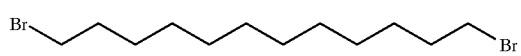 X-194 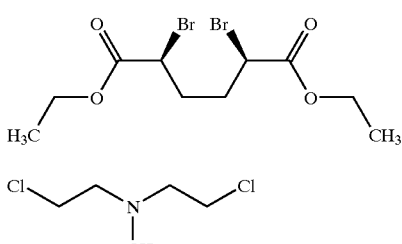
X-195 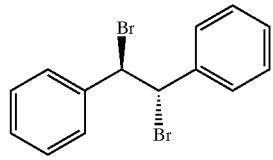 X-196
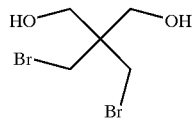
X-197 X-198 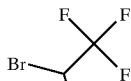
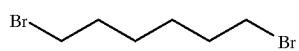
X-199 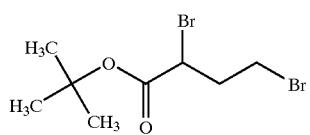 X-200
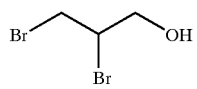
X-201 X-202 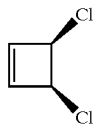
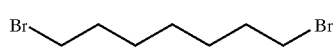
X-203 X-204
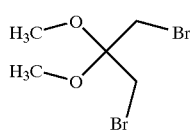
X-205 X-206
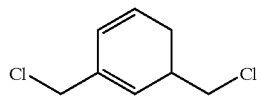
X-207 X-208
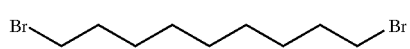
X-209 X-210
X-211 X-212 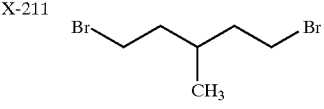

-continued
X-213
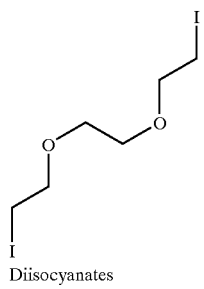
X-214
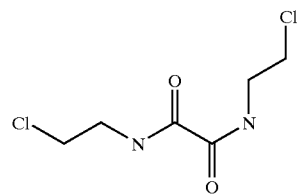
Diisocyanates
X-215
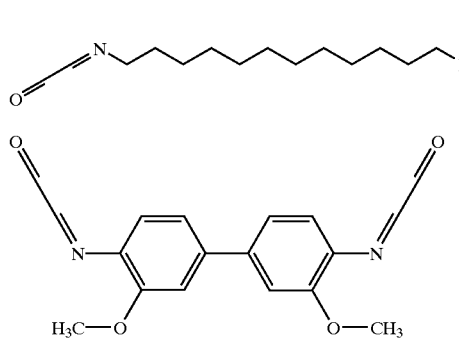
X-216
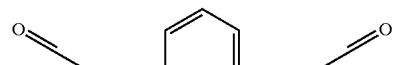
X-217
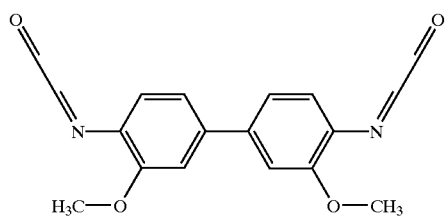
X-218
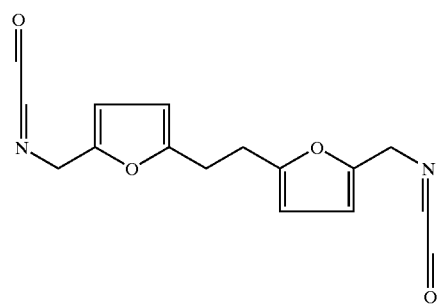
X-219
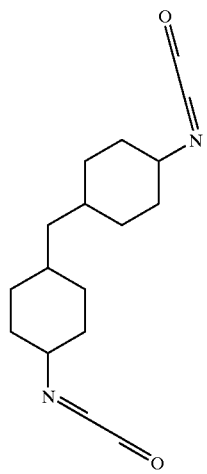
X-220
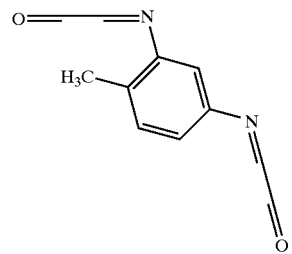
X-221
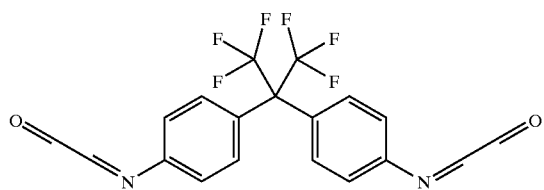
X-222
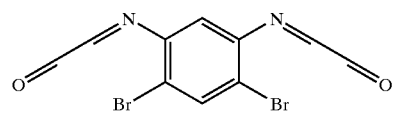
X-223
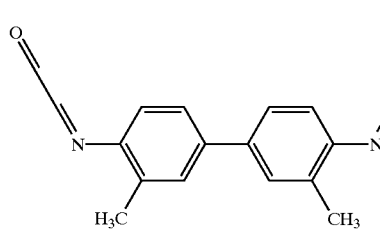
X-224
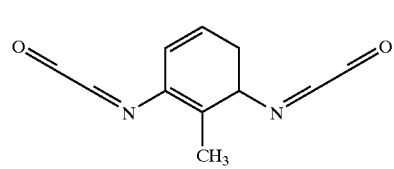

-continued
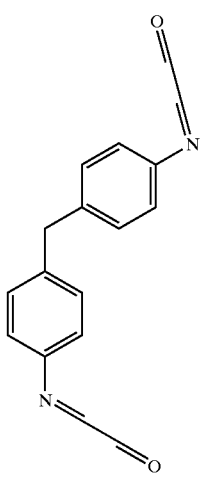
X-225
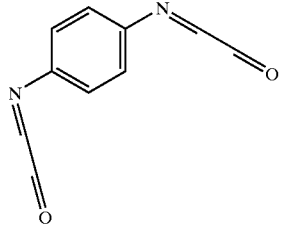
X-226
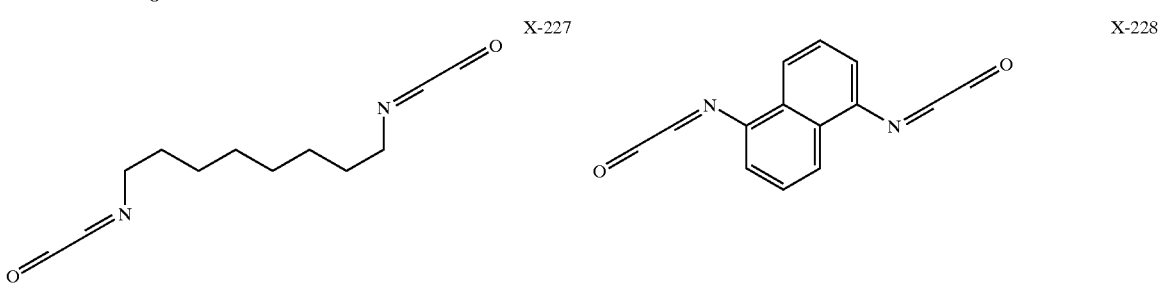
X-227   X-228
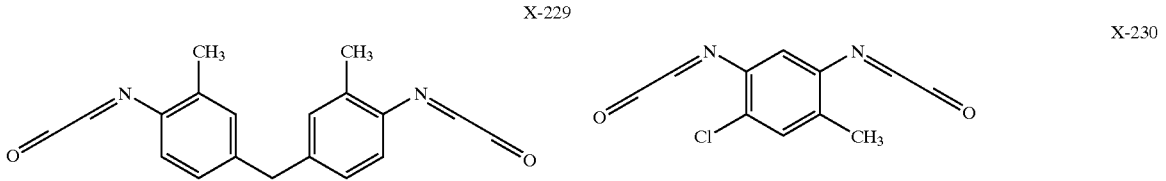
X-229   X-230
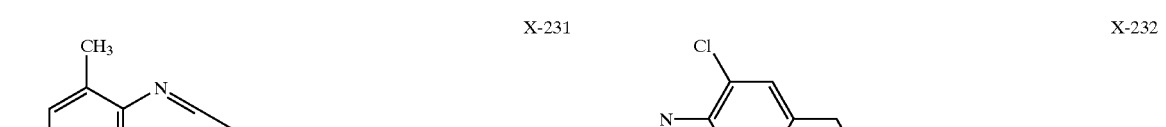
X-231   X-232
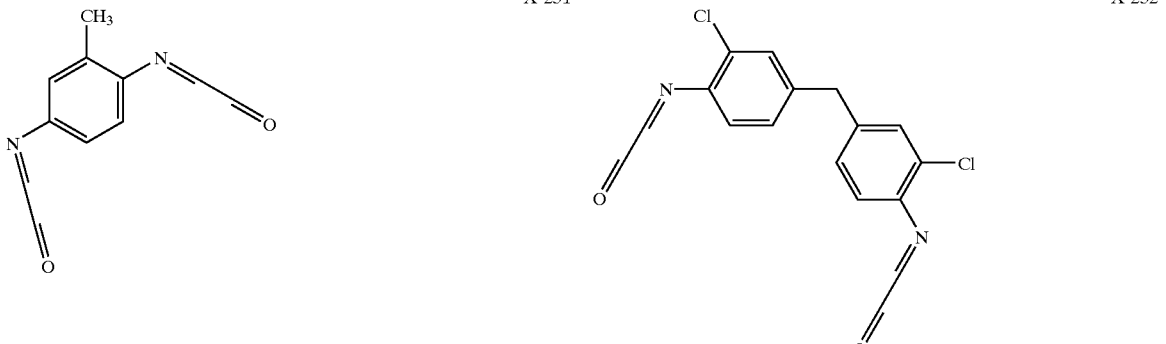
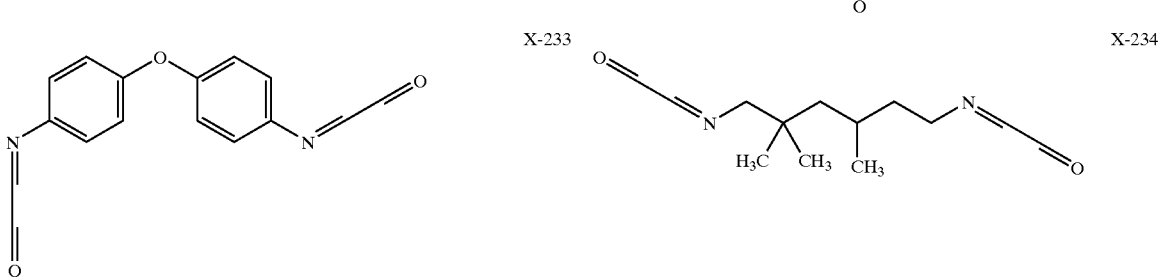
X-233   X-234

-continued
X-235
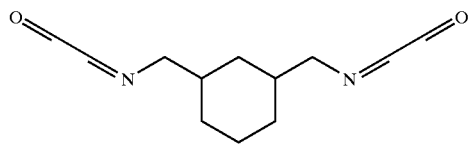
X-236
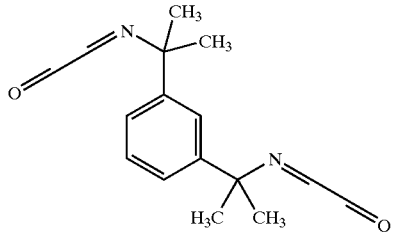
X-237
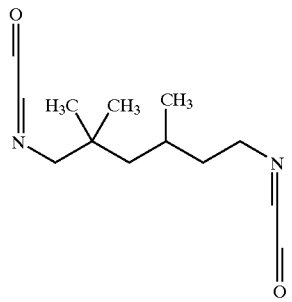
X-238
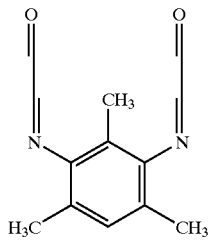
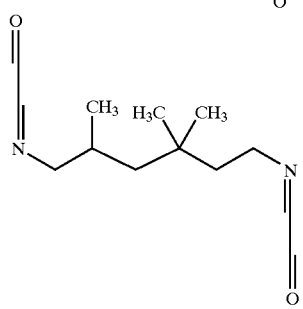
X-239
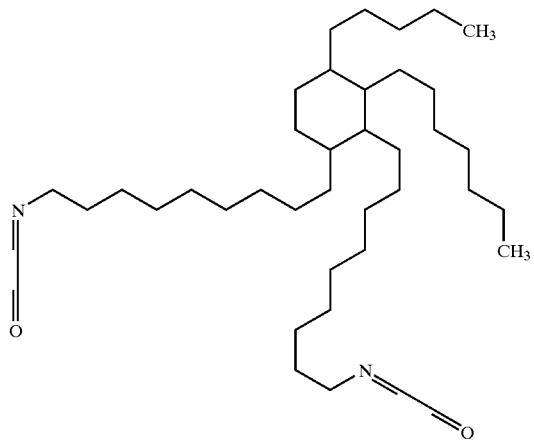
X-240
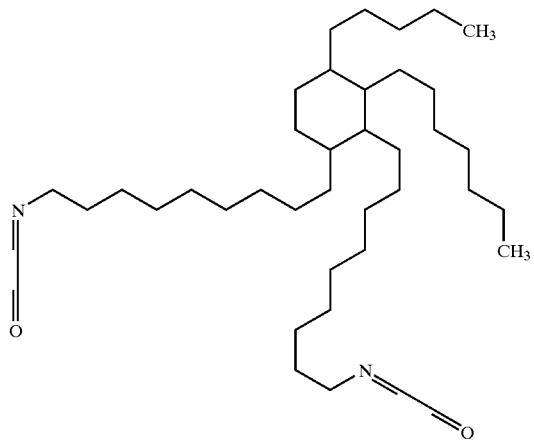
X-241
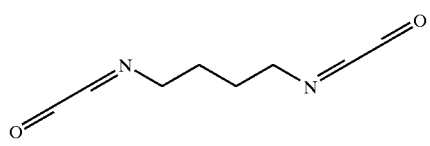
X-242
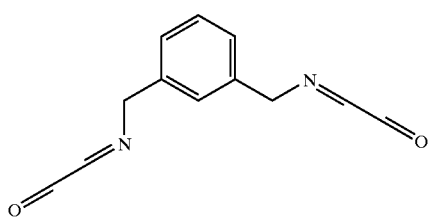

-continued
X-243 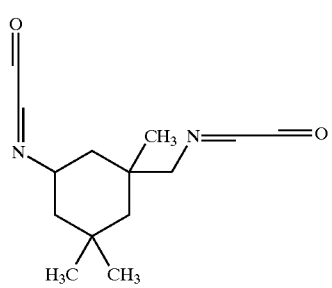
X-244 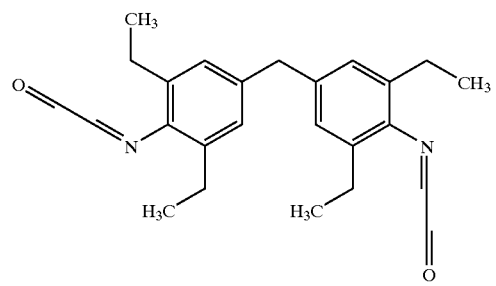
X-245 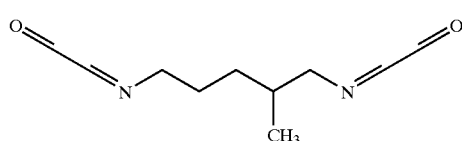
X-246 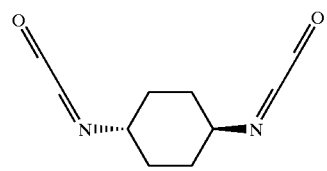
X-247 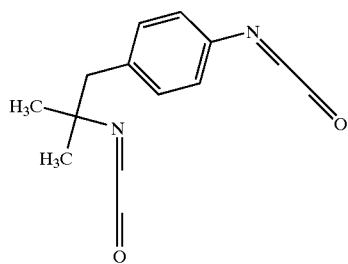
X-248 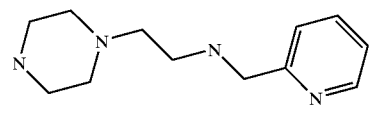
Diamines
X-249 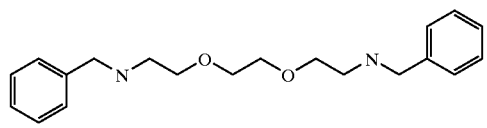
X-250 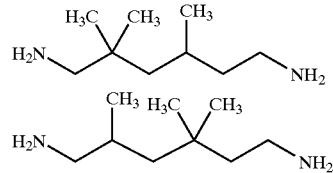
X-251 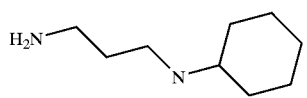
X-252 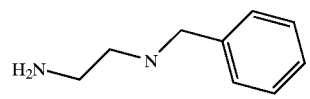
X-253 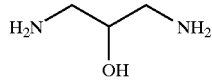
X-254 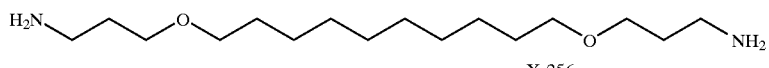
X-255 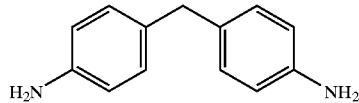
X-256 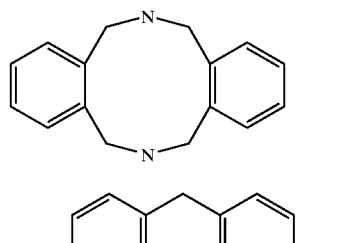
X-257 
X-258
X-259

-continued
X-260 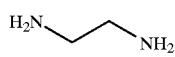
X-261 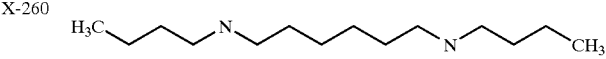
X-262 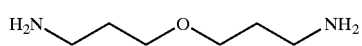
X-263 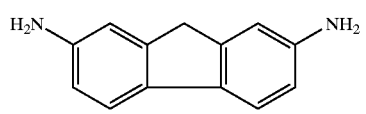
X-264
X-265 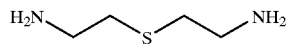
X-266
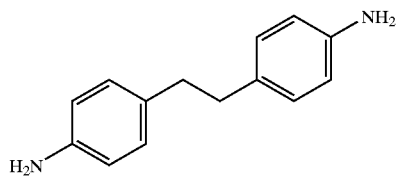
X-267
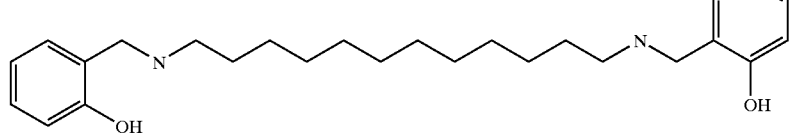
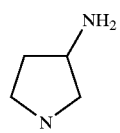
X-268 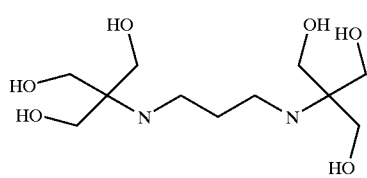
X-269 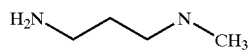
X-270
X-271 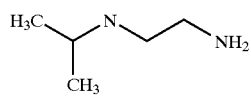
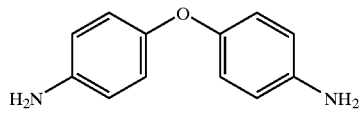
X-272 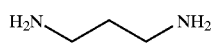
X-273 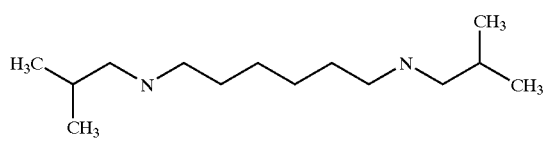
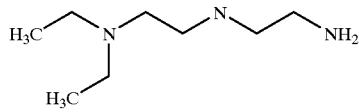
X-274 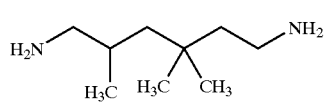
X-275
X-276 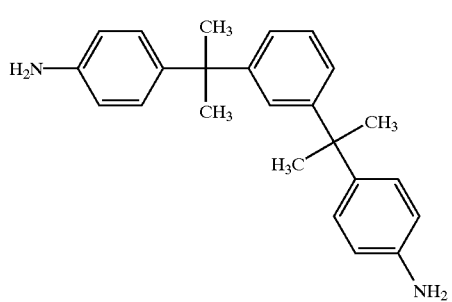
X-277 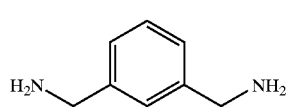

-continued
X-278 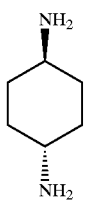 X-279 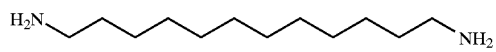
X-280 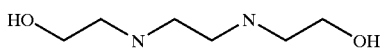 X-281 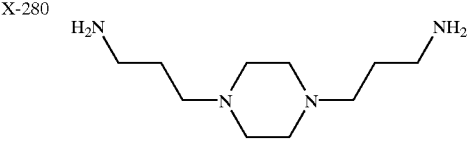
X-282 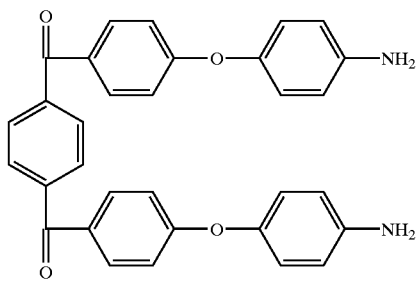 X-283 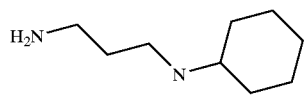
X-284 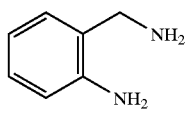 X-285 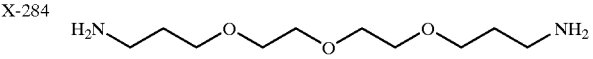
X-286 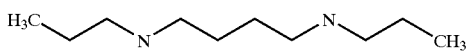 X-287 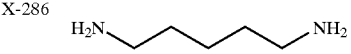
X-288 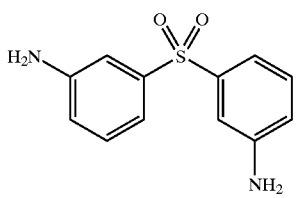 X-289 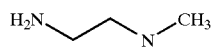
X-290  X-291 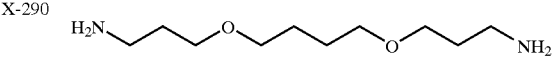
X-292 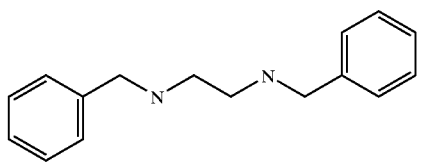 X-293 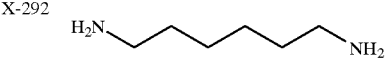
X-294 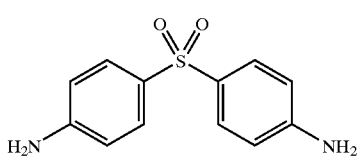 X-295 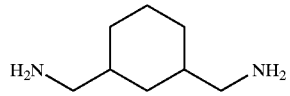

-continued
X-296 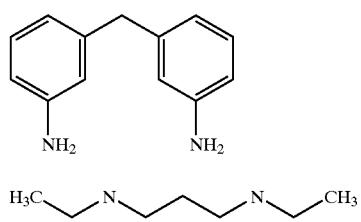
X-297 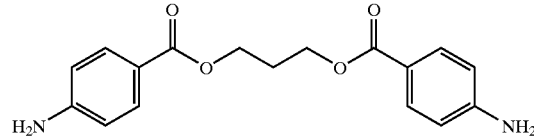
X-298 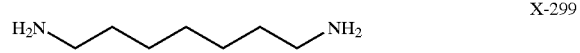  X-299
X-300 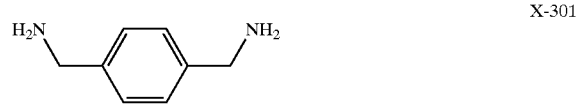 X-301
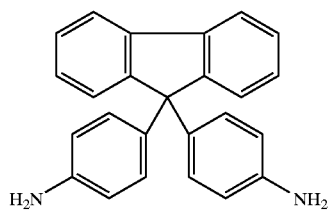
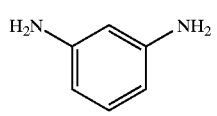 X-302
X-303 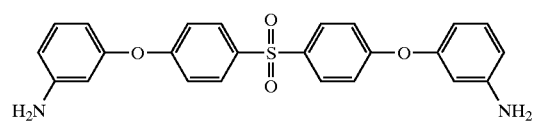
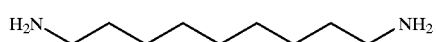
X-304 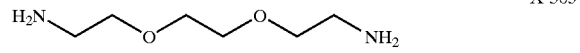 X-305
X-306  X-307
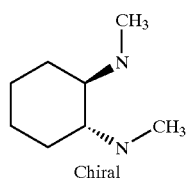
X-308
X-309 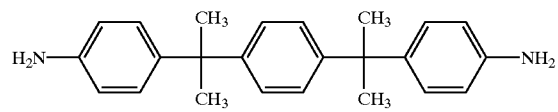
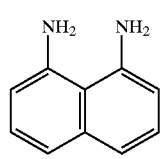
X-310 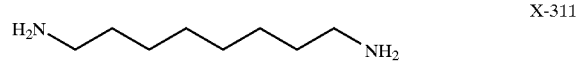 X-311
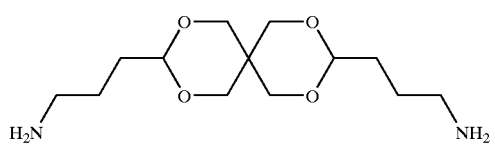
X-312 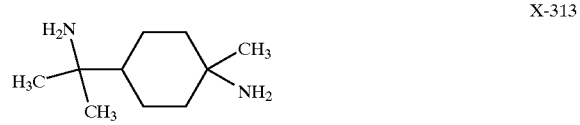 X-313
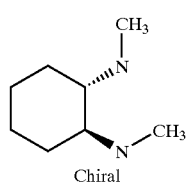
X-314 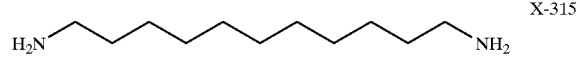 X-315
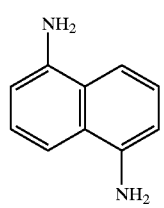

-continued
X-316 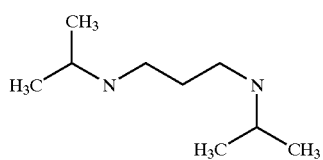
X-317 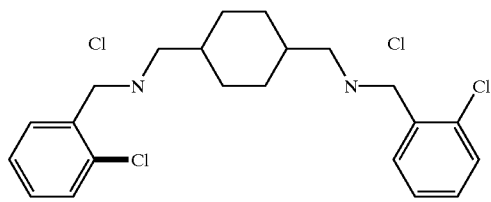
X-318 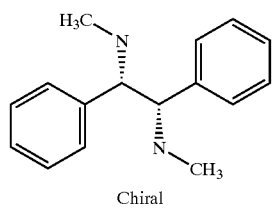
Chiral
X-319 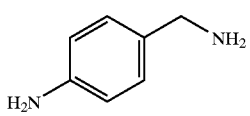
X-320 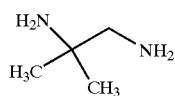
X-321 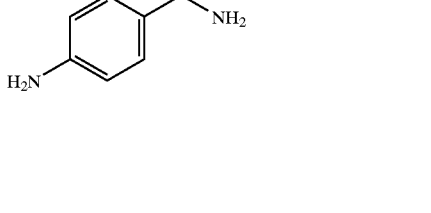
X-322 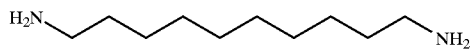
X-323 
X-324 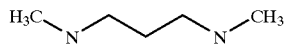
X-325 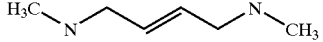
Diols
X-326 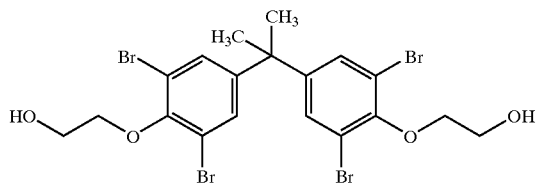
X-327 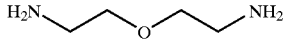
X-328 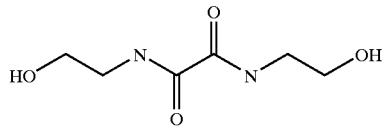
X-329 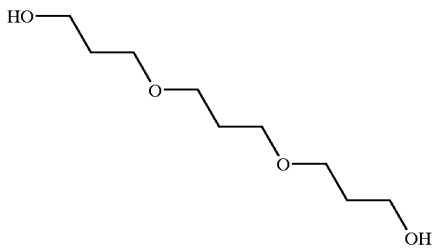
X-330 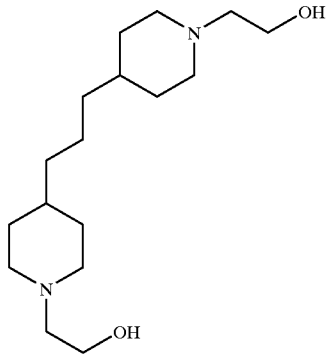
X-331 

-continued
X-332 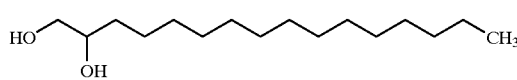
X-333 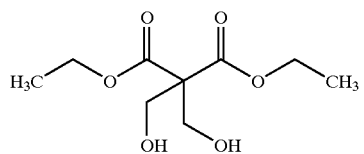
X-334 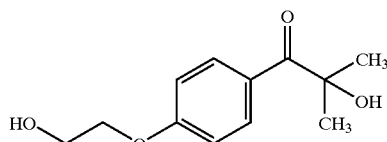
X-335 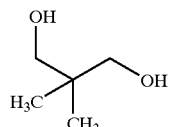
X-336 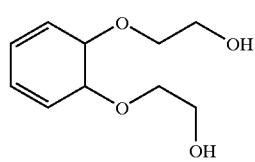
X-337 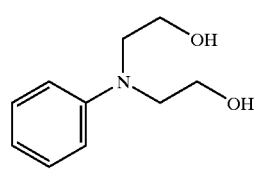
X-338 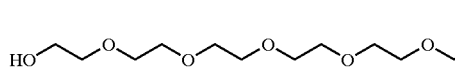
X-339 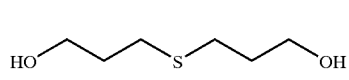
X-340 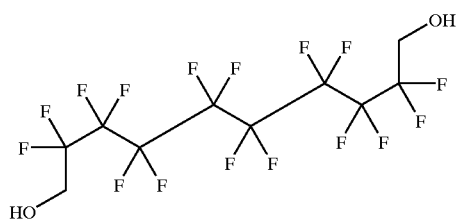
X-341 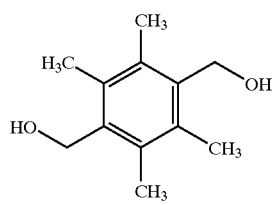
X-342 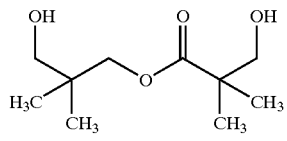
X-343 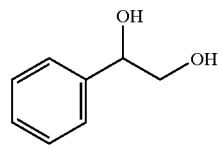
X-344 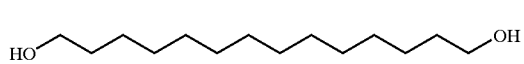
X-345 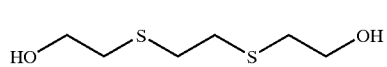
X-346 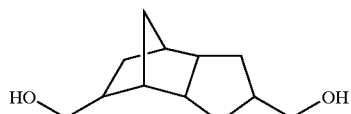
X-347 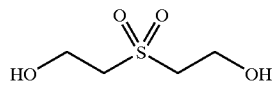
X-348 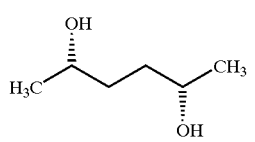
X-349 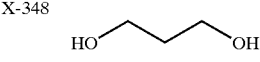
X-350 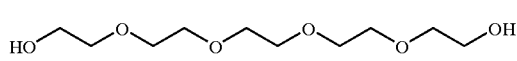
X-351 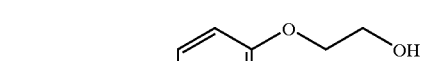
X-352 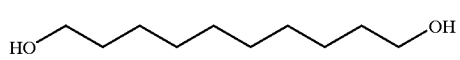
X-353 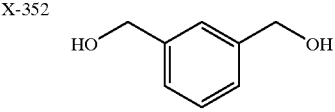

X-354
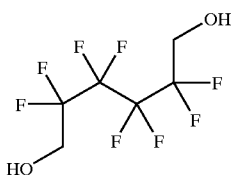
X-355
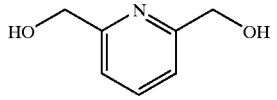
X-356
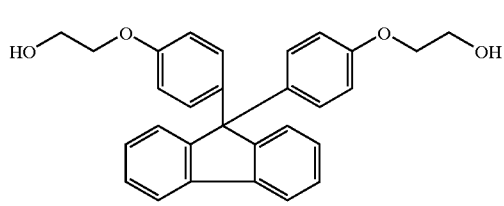
X-357
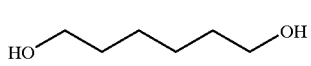
X-358
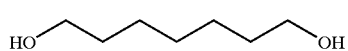
X-359
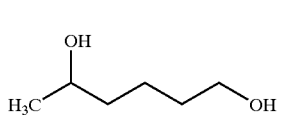
X-360
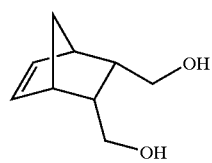
X-361
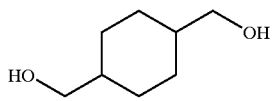
X-362
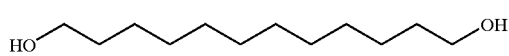
X-363
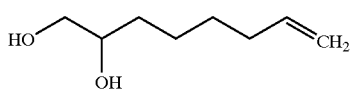
X-364
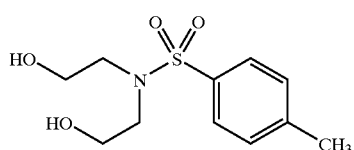
X-365
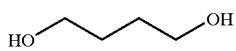
X-366
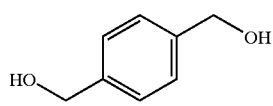
X-367
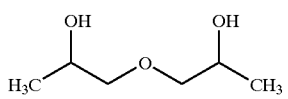
X-368
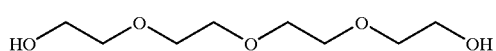
X-369
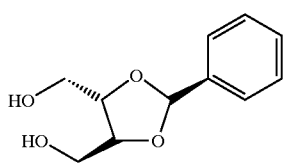
X-370
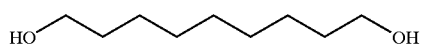
X-371
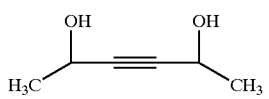
X-372
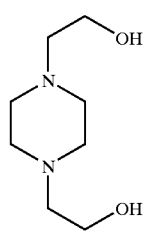
X-373
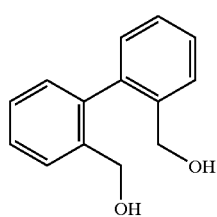

-continued
X-374
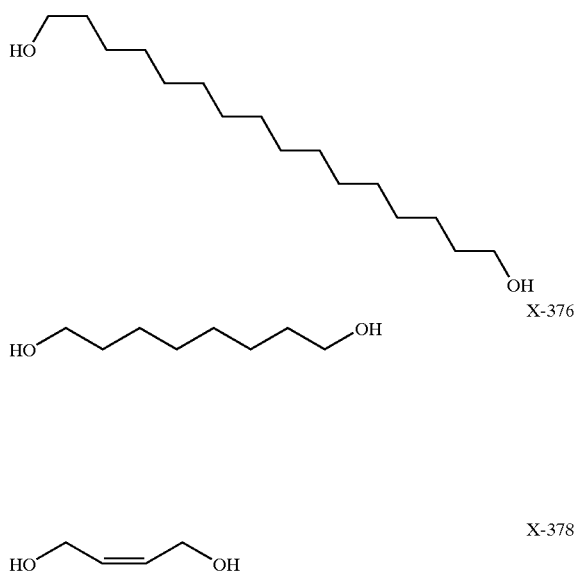
X-375
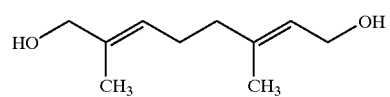
X-376
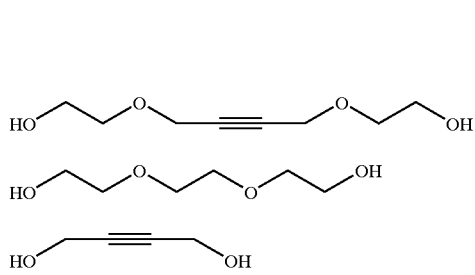
X-377
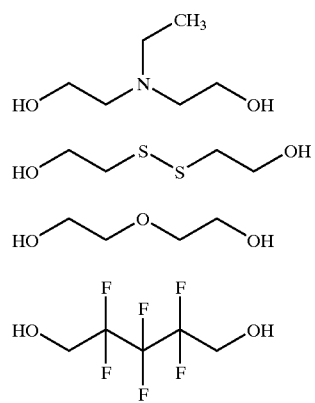
X-378
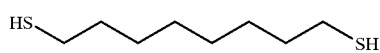
X-379
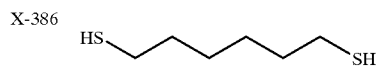
X-380
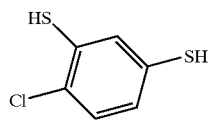
X-381
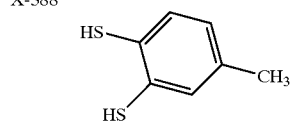
X-382
X-383
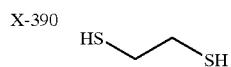
X-384
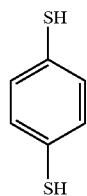
X-385
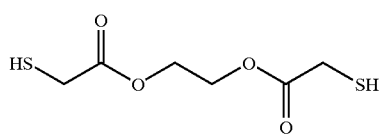
Dithiols
X-386
X-387
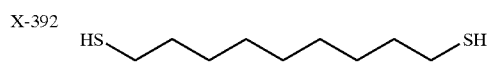
X-388
X-389
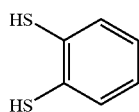
X-390
X-391
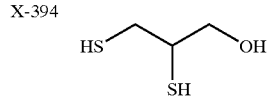
X-392
X-393
X-394
X-395

-continued
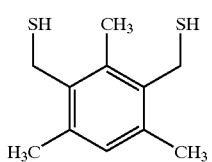
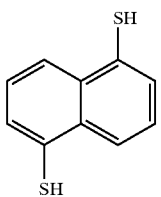
X-396
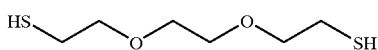
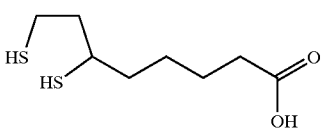
X-398
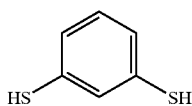
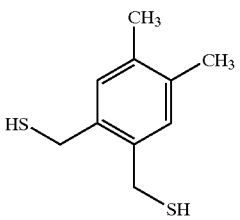
X-400
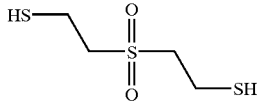
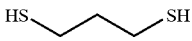
X-402
X-404
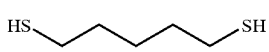
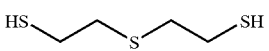
X-406
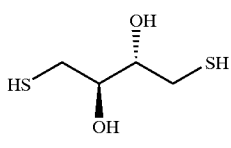
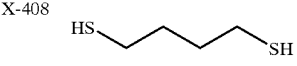
X-408
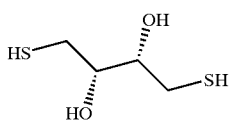
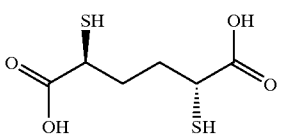
X-410
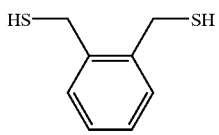
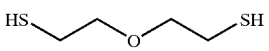
X-412
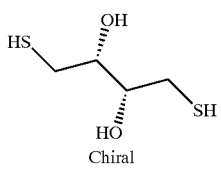
Chiral
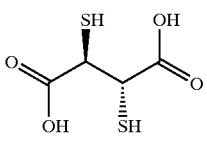
X-414
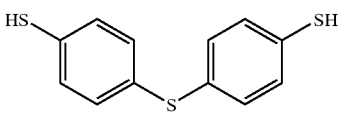
X-416
X-397
X-399
X-401
X-403
X-405
X-407
X-409
X-411
X-413
X-415
X-417

X-418

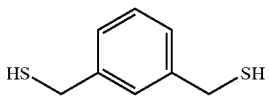

Representative ligands for use in this invention include, by way of example, ligands of formula IA–IC and IIA–IIC as defined herein.

Combinations of ligands (L) and linkers (X) per this invention include, by way example only, homo- and heterodimers wherein a first ligand is selected from formula IA through IC above and the second ligand and linker is selected from the following:

| | | | | | |
|---|---|---|---|---|---|
| IA/X-1- | IA/X-2- | IA/X-3- | IA/X-4- | IA/X-5- | IA/X-6- |
| IA/X-7- | IA/X-8- | IA/X-9- | IA/X-10- | IA/X-11- | IA/X-12- |
| IA/X-13- | IA/X-14- | IA/X-15- | IA/X-16- | IA/X-17- | IA/X-18- |
| IA/X-19- | IA/X-20- | IA/X-21- | IA/X-22- | IA/X-23- | IA/X-24- |
| IA/X-25- | IA/X-26- | IA/X-27- | IA/X-28- | IA/X-29- | IA/X-30- |
| IA/X-31- | IA/X-32- | IA/X-33- | IA/X-34- | IA/X-35- | IA/X-36- |
| IA/X-37- | IA/X-38- | IA/X-39- | IA/X-40- | IA/X-41- | IA/X-42- |
| IA/X-43- | IA/X-44- | IA/X-45- | IA/X-46- | IA/X-47- | IA/X-48- |
| IA/X-49- | IA/X-50- | IA/X-51- | IA/X-52- | IA/X-53- | IA/X-54- |
| IA/X-55- | IA/X-56- | IA/X-57- | IA/X-58- | IA/X-59- | IA/X-60- |
| IA/X-61- | IA/X-62- | IA/X-63- | IA/X-64- | IA/X-65- | IA/X-66- |
| IA/X-67- | IA/X-68- | IA/X-69- | IA/X-70- | IA/X-71- | IA/X-72- |
| IA/X-73- | IA/X-74- | IA/X-75- | IA/X-76- | IA/X-77- | IA/X-78- |
| IA/X-79- | IA/X-80- | IA/X-81- | IA/X-82- | IA/X-83- | IA/X-84- |
| IA/X-85- | IA/X-86- | IA/X-87- | IA/X-88- | IA/X-89- | IA/X-90- |
| IA/X-91- | IA/X-92- | IA/X-93- | IA/X-94- | IA/X-95- | IA/X-96- |
| IA/X-97- | IA/X-98- | IA/X-99- | IA/X-100- | IA/X-101- | IA/X-102- |
| IA/X-103- | IA/X-104- | IA/X-105- | IA/X-106- | IA/X-107- | IA/X-108- |
| IA/X-109- | IA/X-110- | IA/X-111- | IA/X-112- | IA/X-113- | IA/X-114- |
| IA/X-115- | IA/X-116- | IA/X-117- | IA/X-118- | IA/X-119- | IA/X-120- |
| IA/X-121- | IA/X-122- | IA/X-123- | IA/X-124- | IA/X-125- | IA/X-126- |
| IA/X-127- | IA/X-128- | IA/X-129- | IA/X-130- | IA/X-131- | IA/X-132- |
| IA/X-133- | IA/X-134- | IA/X-135- | IA/X-136- | IA/X-137- | IA/X-138- |
| IA/X-139- | IA/X-140- | IA/X-141- | IA/X-142- | IA/X-143- | IA/X-144- |
| IA/X-145- | IA/X-146- | IA/X-147- | IA/X-148- | IA/X-149- | IA/X-150- |
| IA/X-151- | IA/X-152- | IA/X-153- | IA/X-154- | IA/X-155- | IA/X-156- |
| IA/X-157- | IA/X-158- | IA/X-159- | IA/X-160- | IA/X-161- | IA/X-162- |
| IA/X-163- | IA/X-164- | IA/X-165- | IA/X-166- | IA/X-167- | IA/X-168- |
| IA/X-169- | IA/X-170- | IA/X-171- | IA/X-172- | | |
| IA/X-173- | IA/X-174- | IA/X-175- | IA/X-176- | IA/X-177- | IA/X-178- |
| IA/X-179- | IA/X-180- | IA/X-181- | IA/X-182- | IA/X-183- | IA/X-184- |
| IA/X-185- | IA/X-186- | IA/X-187- | IA/X-188- | IA/X-189- | IAIX-190- |
| IA/X-191- | IA/X-192- | IA/X-193- | IA/X-194- | IA/X-195- | IA/X-196- |
| IA/X-197- | IA/X-198- | IA/X-199- | IA/X-200- | IA/X-201- | IA/X-202- |
| IA/X-203- | IA/X-204- | IA/X-205- | IA/X-206- | IA/X-207- | IA/X-208- |
| IA/X-209- | IA/X-210- | IA/X-211- | IA/X-212- | IA/X-213- | IA/X-214- |
| IA/X-215- | IA/X-216- | IA/X-217- | IA/X-218- | IA/X-219- | IA/X-220- |
| IA/X-221- | IA/X-222- | IA/X-223- | IA/X-224- | IA/X-225- | IA/X-226- |
| IA/X-227- | IA/X-228- | IA/X-229- | IA/X-230- | IA/X-231- | IA/X-232- |
| IA/X-233- | IA/X-234- | IA/X-235- | IA/X-236- | IA/X-237- | IA/X-238- |
| IA/X-239- | IA/X-240- | IA/X-241- | IA/X-242- | IA/X-243- | IA/X-244- |
| IA/X-245- | IA/X-246- | IA/X-247- | IA/X-248- | IA/X-249- | IA/X-250- |
| IA/X-251- | IA/X-252- | IA/X-253- | IA/X-254- | IA/X-255- | IA/X-256- |
| IA/X-257- | IA/X-258- | IA/X-259- | IA/X-260- | IA/X-261- | IA/X-262- |
| IA/X-263- | IA/X-264- | IA/X-265- | IA/X-266- | IA/X-267- | IA/X-268- |
| IA/X-269- | IA/X-270- | IA/X-271- | IA/X-272- | IA/X-273- | IA/X-274- |
| IA/X-275- | IA/X-276- | IA/X-277- | IA/X-278- | IA/X-279- | IA/X-280- |
| IA/X-281- | IA/X-282- | IA/X-283- | IA/X-284- | IA/X-285- | IA/X-286- |
| IA/X-287- | IA/X-288- | IA/X-289- | IA/X-290- | IA/X-291- | IA/X-292- |
| IA/X-293- | IA/X-294- | IA/X-295- | IA/X-296- | IA/X-297- | IA/X-298- |
| IA/X-299- | IA/X-300- | IA/X-301- | IA/X-302- | IA/X-303- | IA/X-304- |
| IA/X-305- | IA/X-306- | IA/X-307- | IA/X-308- | IA/X-309- | IA/X-310- |
| IA/X-311- | IA/X-312- | IA/X-313- | IA/X-314- | IA/X-315- | IA/X-316- |
| IA/X-317- | IA/X-318- | IA/X-319- | IA/X-320- | IA/X-321- | IA/X-322- |
| IA/X-323- | IA/X-324- | IA/X-325- | IA/X-326- | IA/X-327- | IA/X-328- |
| IA/X-329- | IA/X-330- | IA/X-331- | IA/X-332- | IA/X-333- | IA/X-334- |
| IA/X-335- | IA/X-336- | IA/X-337- | IA/X-338- | IA/X-339- | IA/X-340- |
| IA/X-341- | IA/X-342- | IA/X-343- | IA/X-344- | IA/X-345- | IA/X-346- |
| IA/X-347- | IA/X-348- | IA/X-349- | IA/X-350- | IA/X-351- | IA/X-352- |

-continued

| | | | | | |
|---|---|---|---|---|---|
| IA/X-353- | IA/X-354- | IA/X-355- | IA/X-356- | IA/X-357- | IA/X-358- |
| IA/X-359- | IA/X-360- | IA/X-361- | IA/X-362- | IA/X-363- | IA/X-364- |
| IA/X-365- | IA/X-366- | IA/X-367- | IA/X-368- | IA/X-369- | IA/X-370- |
| IA/X-371- | IA/X-372- | IA/X-373- | IA/X-374- | IA/X-375- | IA/X-376- |
| IA/X-377- | IA/X-378- | IA/X-379- | IA/X-378- | IA/X-381- | IA/X-382- |
| IA/X-383- | IA/X-384- | IA/X-385- | IA/X-386- | IA/X-387- | IA/X-388- |
| IA/X-389- | IA/X-390- | IA/X-391- | IA/X-392- | IA/X-393- | IA/X-394- |
| IA/X-395- | IA/X-396- | IA/X-397- | IA/X-398- | IA/X-399- | IA/X-400- |
| IA/X-401- | IA/X-402- | IA/X-403- | IA/X-404- | IA/X-405- | IA/X-406- |
| IA/X-407- | IA/X-408- | IA/X-409- | IA/X-410- | IA/X-411- | IA/X-412- |
| IA/X-413- | IA/X-414- | IA/X-415- | IA/X-416- | IA/X-417- | IA/X-418- |
| IB/X-1- | IB/X-2- | IB/X-3- | IB/X-4- | IB/X-5- | IB/X-6- |
| IB/X-7- | IB/X-8- | IB/X-9- | IB/X-10- | IB/X-11- | IB/X-12- |
| IB/X-13- | IB/X-14- | IB/X-15- | IB/X-16- | IB/X-17- | IB/X-18- |
| IB/X-19- | IB/X-20- | IB/X-21- | IB/X-22- | IB/X-23- | IB/X-24- |
| IB/X-25- | IB/X-26- | IB/X-27- | IB/X-28- | IB/X-29- | IB/X-30- |
| IB/X-31- | IB/X-32- | IB/X-33- | IB/X-34- | IB/X-35- | IB/X-36- |
| IB/X-37- | IB/X-38- | IB/X-39- | IB/X-40- | IB/X-41- | IB/X-42- |
| IB/X-43- | IB/X-44- | IB/X-45- | IB/X-46- | IB/X-47- | IB/X-48- |
| IB/X-49- | IB/X-50- | IB/X-51- | IB/X-52- | IB/X-53- | IB/X-54- |
| IB/X-55- | IB/X-56- | IB/X-57- | IB/X-58- | IB/X-59- | IB/X-60- |
| IB/X-61- | IB/X-62- | IB/X-63- | IB/X-64- | IB/X-65- | IB/X-66- |
| IB/X-67- | IB/X-68- | IB/X-69- | IB/X-70- | IB/X-71- | IB/X-72- |
| IB/X-73- | IB/X-74- | IB/X-75- | IB/X-76- | IB/X-77- | IB/X-78- |
| IB/X-79- | IB/X-80- | IB/X-81- | IB/X-82- | IB/X-83- | IB/X-84- |
| IB/X-85- | IB/X-86- | IB/X-87- | IB/X-88- | IB/X-89- | IB/X-90- |
| IB/X-91- | IB/X-92- | IB/X-93- | IB/X-94- | IB/X-95- | IB/X-96- |
| IB/X-97- | IB/X-98- | IB/X-99- | IB/X-100- | IB/X-101- | IB/X-102- |
| IB/X-103- | IB/X-104- | IB/X-105- | IB/X-106- | IB/X-107- | IB/X-108- |
| IB/X-109- | IB/X-110- | IB/X-111- | IB/X-112- | IB/X-113- | IB/X-114- |
| IB/X-115- | IB/X-116- | IB/X-117- | IB/X-118- | IB/X-119- | IB/X-120- |
| IB/X-121- | IB/X-122- | IB/X-123- | IB/X-124- | IB/X-125- | IB/X-126- |
| IB/X-127- | IB/X-128- | IB/X-129- | IB/X-130- | IB/X-131- | IB/X-132- |
| IB/X-133- | IB/X-134- | IB/X-135- | IB/X-136- | IB/X-137- | IB/X-138- |
| IB/X-139- | IB/X-140- | IB/X-141- | IB/X-142- | IB/X-143- | IB/X-144- |
| IB/X-145- | IB/X-146- | IB/X-147- | IB/X-148- | IB/X-149- | IB/X-150- |
| IB/X-151- | IB/X-152- | IB/X-153- | IB/X-154- | IB/X-155- | IB/X-156- |
| IB/X-157- | IB/X-158- | IB/X-159- | IB/X-160- | IB/X-161- | IB/X-162- |
| IB/X-163- | IB/X-164- | IB/X-165- | IB/X-166- | IB/X-167- | IB/X-168- |
| IB/X-169- | IB/X-170- | IB/X-171- | IB/X-172- | | |
| IB/X-173- | IB/X-174- | IB/X-175- | IB/X-176- | IB/X-177- | IB/X-178- |
| IB/X-179- | IB/X-180- | IB/X-181- | IB/X-182- | IB/X-183- | IB/X-184- |
| IB/X-185- | IB/X-186- | IB/X-187- | IB/X-188- | IB/X-189- | IB/X-190- |
| IB/X-191- | IB/X-192- | IB/X-193- | IB/X-194- | IB/X-195- | IB/X-196- |
| IB/X-197- | IB/X-198- | IB/X-199- | IB/X-200- | IB/X-201- | IB/X-202- |
| IB/X-203- | IB/X-204- | IB/X-205- | IB/X-206- | IB/X-207- | IB/X-208- |
| IB/X-209- | IB/X-210- | IB/X-211- | IB/X-212- | IB/X-213- | IB/X-214- |
| IB/X-215- | IB/X-216- | IB/X-217- | IB/X-218- | IB/X-219- | IB/X-220- |
| IB/X-221- | IB/X-222- | IB/X-223- | IB/X-224- | IB/X-225- | IB/X-226- |
| IB/X-227- | IB/X-228- | IB/X-229- | IB/X-230- | IB/X-231- | IB/X-232- |
| IB/X-233- | IB/X-234- | IB/X-235- | IB/X-236- | IB/X-237- | IB/X-238- |
| IB/X-239- | IB/X-240- | IB/X-241- | IB/X-242- | IB/X-243- | IB/X-244- |
| IB/X-245- | IB/X-246- | IB/X-247- | IB/X-248- | IB/X-249- | IB/X-250- |
| IB/X-251- | IB/X-252- | IB/X-253- | IB/X-254- | IB/X-255- | IB/X-256- |
| IB/X-257- | IB/X-258- | IB/X-259- | IB/X-260- | IB/X-261- | IB/X-262- |
| IB/X-263- | IB/X-264- | IB/X-265- | IB/X-266- | IB/X-267- | IB/X-268- |
| IB/X-269- | IB/X-270- | IB/X-271- | IB/X-272- | IB/X-273- | IB/X-274- |
| IB/X-275- | IB/X-276- | IB/X-277- | IB/X-278- | IB/X-279- | IB/X-280- |
| IB/X-281- | IB/X-282- | IB/X-283- | IB/X-284- | IB/X-285- | IB/X-286- |
| IB/X-287- | IB/X-288- | IB/X-289- | IB/X-290- | IB/X-291- | IB/X-292- |
| IB/X-293- | IB/X-294- | IB/X-295- | IB/X-296- | IB/X-297- | IB/X-298- |
| IB/X-299- | IB/X-300- | IB/X-301- | IB/X-302- | IB/X-303- | IB/X-304- |
| IB/X-305- | IB/X-306- | IB/X-307- | IB/X-308- | IB/X-309- | IB/X-310- |
| IB/X-31 J- | IB/X-312- | IB/X-313- | IB/X-314- | IB/X-315- | IB/X-316- |
| IB/X-317- | IB/X-318- | IB/X-319- | IB/X-320- | IB/X-321- | IB/X-322- |
| IB/X-323- | IB/X-324- | IB/X-325- | IB/X-326- | IB/X-327- | IB/X-328- |
| IB/X-329- | IB/X-330- | IB/X-331- | IB/X-332- | IB/X-333- | IB/X-334- |
| IB/X-335- | IB/X-336- | IB/X-337- | IB/X-338- | IB/X-339- | IB/X-340- |
| IB/X-341- | IB/X-342- | IB/X-343- | IB/X-344- | IB(X-345- | IB/X-346- |

-continued

| | | | | | |
|---|---|---|---|---|---|
| IB/X-347- | IB/X-348- | IB/X-349- | IB/X-350- | IB(X-351- | IB/X-352- |
| IB/X-353- | IB/X-354- | IB/X-355- | IB/X-356- | IB/X-357- | IB/X-358- |
| IB/X-359- | IB/X-360- | IB/X-361- | IB/X-362- | IB/X-363- | IB/X-364- |
| IB/X-365- | IB/X-366- | IB/X-367- | IB/X-368- | IB/X-369- | IB/X-370- |
| IB/X-371- | IB/X-372- | IB/X-373- | IB/X-374- | IB/X-375- | IB/X-376- |
| IB/X-377- | IB/X-378- | IB/X-379- | IB/X-380- | IB/X-381- | IB/X-382- |
| IB/X-383- | IB/X-384- | IB/X-385- | IB/X-386- | IB/X-387- | IB/X-388- |
| IB/X-389- | IB/X-390- | IB/X-391- | IB/X-392- | IB/X-393- | IB/X-394- |
| IB/X-395- | IB/X-396- | IB/X-397- | IB/X-398- | IB/X-399- | IB/X-400- |
| IB/X-401- | IB/X-402- | IB/X-403- | IB/X-404- | IB/X-405- | IB/X-406- |
| IB/X-407- | IB/X-408- | IB/X-409- | IB/X-410- | IB/X-411- | IB/X-412- |
| IB/X-413- | IB/X-414- | IB/X-415- | IB/X-416- | IB/X-417- | IB/X-418- |
| IC/X-1- | IC/X-2- | IC/X-3- | IC/X-4- | IC/X-5- | IC/X-6- |
| IC/X-7- | IC/X-8- | IC/X-9- | IC/X-10- | IC/X-11- | IC/X-12- |
| IC/X-13- | IC/X-14- | IC/X-15- | IC/X-16- | IC/X-17- | IC/X-18- |
| IC/X-19- | IC/X-20- | IC/X-21- | IC/X-22- | IC/X-23- | IC/X-24- |
| IC/X-25- | IC/X-26- | IC/X-27- | IC/X-28- | IC/X-29- | IC/X-30- |
| IC/X-31- | IC/X-32- | IC/X-33- | IC/X-34- | IC/X-35- | IC/X-36- |
| IC/X-37- | IC/X-38- | IC/X-39- | IC/X-40- | IC/X-41- | IC/X-42- |
| IC/X-43- | IC/X-44- | IC/X-45- | IC/X-46- | IC/X-47- | IC/X-48- |
| IC/X-49- | IC/X-50- | IC/X-51- | IC/X-52- | IC/X-53- | IC/X-54- |
| IC/X-55- | IC/X-56- | IC/X-57- | IC/X-58- | IC/X-59- | IC/X-60- |
| IC/X-61- | IC/X-62- | IC/X-63- | IC/X-64- | IC/X-65- | IC/X-66- |
| IC/X-67- | IC/X-68- | IC/X-69- | IC/X-70- | IC/X-71- | IC/X-72- |
| IC/X-73- | IC/X-74- | IC/X-75- | IC/X-7- | IC/X-77- | IC/X-78- |
| IC/X-79- | IC/X-80- | IC/X-81- | IC/X-82- | IC/X-83- | IC/X-84- |
| IC/X-85- | IC/X-86- | IC/X-87- | IC/X-88- | IC/X-89- | IC/X-90- |
| IC/X-91- | IC/X-92- | IC/X-93- | IC/X-94- | IC/X-95- | IC/X-96- |
| IC/X-97- | IC/X-98- | IC/X-99- | IC/X-100- | IC/X-101- | IC/X-102- |
| IC/X-103- | IC/X-104- | IC/X-105- | IC/X-106- | IC/X-107- | IC/X-108- |
| IC/X-109- | IC/X-110- | IC/X-111- | IC/X-112- | IC/X-113- | IC/X-114- |
| IC/X-115- | IC/X-116- | IC/X-117- | IC/X-118- | IC/X-119- | IC/X-120- |
| IC/X-121- | IC/X-122- | IC/X-123- | IC/X-124- | IC/X-125- | IC/X-126- |
| IC/X-127- | IC/X-128- | IC/X-129- | IC/X-130- | IC/X-131- | IC/X-132- |
| IC/X-133- | IC/X-134- | IC/X-135- | IC/X-136- | IC/X-137- | IC/X-138- |
| IC/X-139- | IC/X-140- | IC/X-141- | IC/X-142- | IC/X-143- | IC/X-144- |
| IC/X-145- | IC/X-146- | IC/X-147- | IC/X-148- | IC/X-149- | IC/X-150- |
| IC/X-151- | IC/X-152- | IC/X-153- | IC/X-154- | IC/X-155- | IC/X-156- |
| IC/X-157- | IC/X-158- | IC/X-159- | IC/X-160- | IC/X-161- | IC/X-162- |
| IC/X-163- | IC/X-164- | IC/X-165- | IC/X-166- | IC/X-167- | IC/X-168- |
| IC/X-169- | IC/X-170- | IC/X-171- | IC/X-172- | | |
| IC/X-173- | IC/X-174- | IC/X-175- | IC/X-176- | IC/X-177- | IC/X-178- |
| IC/X-179- | IC/X-180- | IC/X-181- | IC/X-182- | IC/X-183- | IC/X-184- |
| IC/X-185- | IC/X-186- | IC/X-187- | IC/X-188- | IC/X-189- | IC/X-190- |
| IC/X-191- | IC/X-192- | IC/X-193- | IC/X-194- | IC/X-195- | IC/X-196- |
| IC/X-197- | IC/X-198- | IC/X-199- | IC/X-200- | IC/X-201- | IC/X-202- |
| IC/X-203- | IC/X-204- | IC/X-205- | IC/X-206- | IC/X-207- | IC/X-208- |
| IC/X-209- | IC/X-210- | IC/X-211- | IC/X-212- | IC/X-213- | IC/X-214- |
| IC/X-215- | IC/X-216- | IC/X-217- | IC/X-218- | IC/X-219- | IC/X-220- |
| IC/X-221- | IC/X-222- | IC/X-223- | IC/X-224- | IC/X-225- | IC/X-226- |
| IC/X-227- | IC/X-228- | IC/X-229- | IC/X-230- | IC/X-231- | IC/X-232- |
| IC/X-233- | IC/X-234- | IC/X-235- | IC/X-236- | IC/X-237- | IC/X-238- |
| IC/X-239- | IC/X-240- | IC/X-241- | IC/X-242- | IC/X-243- | IC/X-244- |
| IC/X-245- | IC/X-246- | IC/X-247- | IC/X-248- | IC/X-249- | IC/X-250- |
| IC/X-251- | IC/X-252- | IC/X-253- | IC/X-254- | IC/X-255- | IC/X-256- |
| IC/X-257- | IC/X-258- | IC/X-259- | IC/X-260- | IC/X-261- | IC/X-262- |
| IC/X-263- | IC/X-264- | IC/X-265- | IC/X-266- | IC/X-267- | IC/X-268- |
| IC/X-269- | IC/X-270- | IC/X-271- | IC/X-272- | IC/X-273- | IC/X-274- |
| IC/X-275- | IC/X-276- | IC/X-277- | IC/X-278- | IC/X-279- | IC/X-280- |
| IC/X-281- | IC/X-282- | IC/X-283- | IC/X-284- | IC/X-285- | IC/X-286- |
| IC/X-287- | IC/X-288- | IC/X-289- | IC/X-290- | IC/X-291- | IC/X-292- |
| IC/X-293- | IC/X-294- | IC/X-295- | IC/X-296- | IC/X-297- | IC/X-298- |
| IC/X-299- | IC/X-300- | IC/X-301- | IC/X-302- | IC/X-303- | IC/X-304- |
| IC/X-305- | IC/X-306- | IC/X-307- | IC/X-308- | IC/X-309- | IC/X-310- |
| IC/X-311- | IC/X-312- | IC/X-313- | IC/X-314- | IC/X-315- | IC/X-316- |
| IC/X-317- | IC/X-318- | IC/X-319- | IC/X-320- | IC/X-321- | IC/X-322- |
| IC/X-323- | IC/X-324- | IC/X-325- | IC/X-326- | IC/X-327- | IC/X-328- |
| IC/X-329- | IC/X-330- | IC/X-331- | IC/X-332- | IC/X-333- | IC/X-334- |
| IC/X-335- | IC/X-336- | IC/X-337- | IC/X-338- | IC/X-339- | IC/X-340- |
| IC/X-341- | IC/X-342- | IC/X-343- | IC/X-344- | IC/X-345- | IC/X-346- |
| IC/X-347- | IC/X-348- | IC/X-349- | IC/X-350- | IC/X-351- | IC/X-352- |
| IC/X-353- | IC/X-354- | IC/X-355- | IC/X-356- | IC/X-357- | IC/X-358- |
| IC/X-359- | IC/X-360- | IC/X-361- | IC/X-362- | IC/X-363- | IC/X-364- |
| IC/X-365- | IC/X-366- | IC/X-367- | IC/X-368- | IC/X-369- | IC/X-370- |
| IC/X-371- | IC/X-372- | IC/X-373- | IC/X-374- | IC/X-375- | IC/X-376- |
| IC/X-377- | IC/X-378- | IC/X-379- | IC/X-380- | IC/X-381- | IC/X-382- |
| IC/X-383- | IC/X-384- | IC/X-385- | IC/X-386- | IC/X-387- | IC/X-388- |
| IC/X-389- | IC/X-390- | IC/X-391- | IC/X-392- | IC/X-393- | IC/X-394- |
| IC/X-395- | IC/X-396- | IC/X-397- | IC/X-398- | IC/X-399- | IC/X-400- |
| IC/X-401- | IC/X-402- | IC/X-403- | IC/X-404- | IC/X-405- | IC/X-406- |
| IC/X-407- | IC/X-408- | IC/X-409- | IC/X-410- | IC/X-411- | IC/X-412- |
| IC/X-413- | IC/X-414- | IC/X-415- | IC/X-416- | IC/X-417- | IC/X-418-. |

Pharmaceutical Formulations

When employed as pharmaceuticals, the compounds of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds described herein associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.001 to about 1 g, more usually about 1 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula I above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

A formulation may be prepared as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 9

A formulation may be prepared as follows:

| Ingredient | Quantity |
|---|---|
| Active Ingredient | 5.0 mg |
| Corn Oil | 1.0 mL |

Formulation Example 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Other suitable formulations for use in the present invention can be found in *Remington's Pharmaceutical Sciences*, Mace Publishing Company, Philadelphia, Pa., 17th ed. (1985).

Utility

The multibinding compounds of this invention inhibit cyclooxygenase-2 (COX-2), an enzyme which catalyzes the first committed step in the biosynthesis of prostaglandins. Accordingly, the multibinding compounds and pharmaceutical compositions of this invention are useful in the treatment and prevention of various disorders mediated by COX-2, such as inflammation, pain, fever and the like.

When used in treating or ameliorating such conditions, the compounds of this invention are typically delivered to a patient in need of such treatment by a pharmaceutical composition comprising a pharmaceutically acceptable diluent and an effective amount of at least one compound of this invention. The amount of compound administered to the patient will vary depending upon what compound and/or composition is being administered, the purpose of the administration, such as prophylaxis or therapy, the state of the patient, the manner of administration, and the like. In therapeutic applications, compositions are administered to a patient already suffering from, for example, inflammation in an amount sufficient to at least partially reduce the inflammation. Amounts effective for this use will depend on the judgment of the attending clinician depending upon factors such as the degree or severity of the inflammation in the patient, the age, weight and general condition of the patient, and the like. The pharmaceutical compositions of this invention may contain more than one compound of the present invention.

As noted above, the compounds administered to a patient are in the form of pharmaceutical compositions described above which can be administered by a variety of routes including oral, rectal, transdermal, subcutaneous, intravenous, intramuscular, etc.. These compounds are effective as both injectable and oral deliverable pharmaceutical compositions. Such compositions are prepared in a manner well known in the pharmaceutical art and comprise at least one active compound.

The multibinding compounds of this invention can also be administered in the form of pro-drugs, i.e., as derivatives which are converted into a biologically active compound in vivo. Such pro-drugs will typically include compounds in which, for example, a carboxylic acid group, a hydroxyl group or a thiol group is converted to a biologically liable group, such as an ester, lactone or thioester group which will hydrolyze in vivo to reinstate the respective group.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

Å=Angstroms
cm=centimeter
DCC=dicyclohexyl carbodiimide
DMF=N,N-dimethylformamide
DMSO=dimethylsulfoxide
EDTA=ethylenediaminetetraacetic acid
g=gram
HPLC=high performance liquid chromatography
MEM=minimal essential medium
mg=milligram
MIC=minimum inhibitory concentration
min=minute
mL=milliliter
mm=millimeter
mmol=millimol
N=normal
THF=tetrahydrofuran
μL=microliters
μm=microns

Example A

Synthesis of 1-(4-Fluorophenyl)-3-(1-hydroxyl) methyl-2-methyl-5-(4-methylsulfonylphenyl)pyrrole (6)

To a solution of 1-(4-fluorophenyl)-2-methyl-5-(4-methylsulfonylphenyl)pyrrole, 5, (in FIG. 6) (prepared as described in *J. Med. Chem.*, 1997, 40, 1619) (1 mmol) in dry DMF (10 mL) at 0° C. is added phosphorus oxychloride (1 mmol). The reaction is monitored by tlc and when it is complete, the mixture is poured onto ice and made basic with aqueous sodium hydroxide. The product is isolated by extraction with $CH_2Cl_2$. The extract is dried and evaporated to afford a residue. To the residue, dissolved in EtOH (10 mL) is added sodium borohydride (100 mg). After one hour, the solution is added to water and extracted with ethyl acetate. The extract is washed with dilute HCl, dried and evaporated. The title compound 6 is purified and isolated by HPLC.

Example B

Synthesis of 1-(4-Fluorophenyl)-3-(4-benzyloxyphenoxy)methyl-2-methyl-5-(4-methylsulfonylphenyl)pyrrole (8)

Compound 6 (from Example A) (1 mmol) is added to a solution of diethylazodicarboxylate (1 mmol) and triphenylphosphine (1 mmol) in dry THF (10 mL). 4-Benzyloxyphenol (7) (1 mmol) is then added, and the progress of the reaction is monitored by tlc. When the reaction is complete, water is added and the product is extracted with ethyl acetate. The extract is dried and evaporated and the title compound 8 is then purified by HPLC.

Example C

Synthesis of 1-(4-Fluorophenyl)-3-(4-hydroxyphenoxy)methyl-2-methyl-5-(4-methylsulfonylphenyl)pyrrole (9)

Compound 8 (from Example B) (1 mmol.) is dissolved in EtOH (25 mL) and 10% Pd/C (25 mg) is added. The reaction mixture is stirred under an atmosphere of $H_2$ and monitored by tlc. When the reaction is complete, the solution is filtered and evaporated to afford a residue which, after purification by HPLC, affords title compound 9.

Example D

Synthesis of Dibromide 11 (wherein n is 3) (see FIG. 8)

Pentaethylene glycol (2 mmol) is dissolved in dry $CH_2Cl_2$ (25 mL) and triphenylphosphine (4 mmol) and carbon tetrabromide (4 mmol) are added. The reaction is monitored by tlc, and when it is complete, the mixture is evaporated to dryness. The product, compound 11 (wherein n=3), is then purified by HPLC. Using a similar procedure, other dihydroxy compounds described herein can be converted to the corresponding dibromides.

Example E

Synthesis of Intermediate 17 (wherein n is 4) (See FIG. 10)

Step A—Preparation of Intermediate 16 (wherein n is 4)

To a solution of methyl 6-bromohexanoateate 15, (LG=Br, PG=CH$_3$, n=4), (1 mmol) in DMF (20 mL) is added K$_2$CO$_3$ (1 g) and then a solution of 9 (from Example C) (1 mmol) in DMF (5 mL). The mixture is stirred at room temperature and monitored by tlc until the reaction is complete. The mixture is then added to water. The aqueous solution is extracted with ethyl acetate, the extract is dried and evaporated, and the product 16 (n=4 and PG=CH3) is then purified by HPLC. In a similar manner, by employing different compounds of formula 15 in which the protecting group (PG) and n are varied as described herein, additional compounds of formula 16 can be prepared.

Step B—Preparation of Intermediate 17 (wherein n is 4)

Compound 16 (0.5 mmol) is dissolved in THF (10 mL) and a solution of LiOH—H$_2$O (0.55 mmol) in water (3 mL) is added. The reaction is monitored by tlc and when it is complete, the solution is neutralized by addition of aqueous NaH$_2$PO$_4$. The mixture is then extracted with CH$_2$Cl$_2$ and the extract is dried and evaporated. The crude product is purified by HPLC to afford the carboxylic acid 17 (n=4).

Example F

Synthesis of Intermediate 20 (wherein n is 4) (See FIG. 11)

Step A—Preparation of Intermediate 18 (wherein n is 2)

1-Hydroxy-4-triphenylmethylaminobutane (5 mmol) is dissolved in pyridine (10 mL) and p-toluenesulfonyl chloride (5 mmol) is added. The reaction is followed by tlc. When the reaction is complete, the solution is added to water and extracted with CH$_2$Cl$_2$. The solution is washed with dilute HCl, then dried and evaporated to afford compound 18 (n=2, PG=CPh$_3$ and LG=p-toluenesulfonyl).

Step B—Preparation of Intermediate 19 (wherein n is 2)

Compound 9 (from Example C) (1 mmol) is dissolved in dry DMF (10 mL) containing K$_2$CO$_3$ (250 mg.) and intermediate compound 18 (1 mmol) is added. The reaction is followed by tlc. When the reaction is complete, the solution is poured into water and extracted with CH$_2$Cl$_2$. The extract is dried and evaporated and the product is purified by HPLC to afford compound 19 (n=2 and PG=CPh$_3$).

Step C—Preparation of Intermediate 20 (wherein n is 2)

The triphenylmethyl-protected compound 19 (0.5 mmol) is dissolved in CH$_2$Cl$_2$ (10 mL) at 0° C. and trifluoroacetic acid (3 mL) is added. The progress of the reaction is followed by tlc. When the reaction is complete, the mixture is poured onto ice and extracted with CH$_2$Cl$_2$. The extract is washed with dilute NaHCO$_3$, then dried and evaporated. Purification by HPLC then affords the compound 20 (n=2).

Example G

Synthesis of 1-(4-Fluorophenyl)-3-(4-iodophenoxy)methyl-2-methyl-5-(4-methylsulfonylphenyl)pyrrole (25)

Compound 6 (from Example A) (1 mmol) is added to a solution of diethylazodicarboxylate (1 mmol), triphenylphosphine (1 mmol) and 4-iodophenol (1 mmol) in dry THF (25 mL). The progress of the reaction is monitored by tlc. When the reaction is complete, water is added and the crude product is extracted in ethyl acetate. The extract is dried and evaporated and the title compound 25 is purified by HPLC.

Example H

Synthesis of 1-(4-Fluorophenyl)-3-(4-carboxyphenoxy)methyl-2-methyl-5-(4-methylsulfonylphenyl)pyrrole (26)

Compound 6 (from Example A) (1 mmol) is added to a solution of diethylazodicarboxylate (1 mmol), triphenylphosphine (1 mmol) and benzyl 4-hydroxybenzoate (1 mmol) in dry THF (25 mL). The progress of the reaction is followed by tlc. When the reaction is complete, water is added and the crude product is extracted with ethyl acetate. The extract is dried and evaporated and the product, i.e., the benzyl ester of compound 26, is purified by HPLC.

The benzyl ester of compound 26 (0.5 mmol) is dissolved in toluene (20 mL) in a hydrogenation apparatus and 10% Pd/C (50 mg) is added. The progress of the reaction is followed by tlc. When the reaction is complete, the solution is filtered and evaporated. The residue is purified by HPLC to afford compound 26.

Example I

Synthesis of 1-(4-Fluorophenyl)-3-(4-aminophenoxy)methyl-2-methyl-5-(4-methylsulfonylphenyl)pyrrole (27)

Compound 6 (from Example A) (1 mmol) is added to a solution of diethylazodicarboxylate (1 mmol), triphenylphosphine (1 mmol) and 4-(tert-butoxycarbonylamino) phenol (1 mmol) in dry THF (25 mL). The progress of the reaction is followed by tlc. When the reaction is complete, water is added and the crude product is extracted with ethyl acetate. The extract is dried and evaporated, and the product, i.e., the BOC-protected derivative of compound 27, is purified by HPLC.

The BOC-protected derivative of compound 27 (0.5 mmol) is dissolved in CH$_2$Cl$_2$ (10 mL) at 0° C. and trifluoroacetic acid (2 mL) is added. The progress of the reaction is followed by tlc. When the reaction is complete, the solution is washed with dilute NaHCO$_3$. The solution is then dried and evaporated. The residue is purified by HPLC to afford compound 27.

Example J

Synthesis of 1-(4-Fluorophenyl)-3-(4-boronophenoxy)methyl-2-methyl-5-(4-methylsulfonylphenyl)pyrrole (28)

Compound 25 (from Example G) (1 mmol), tetramethylbisboronate (CH$_3$O)$_2$B-B(OCH$_3$)$_2$(1mmol), KOAc (3 mmol) and PdCl$_2$ 1,1'-bis(diphenylphosphino)ferrocene (0.03 mmol) are heated in DMSO (25 mL) at 80° C. The progress of the reaction is monitored by tlc. When the reaction is complete, the mixture is cooled and added to water. The aqueous solution is made basic by addition of aqueous NaOH. After 3 hours, the mixture is brought to pH 1 by addition of dilute HCl, and is then extracted with CH$_2$Cl$_2$. The extract is dried and evaporated, and compound 28 is purified by chromatogaphy.

Example K

Synthesis of Bis(iodophenxoxy) Intermediate 31 (See FIG. 16)

Hexaethylene glycol (5 mmol) is dissolved in pyridine (30 mL) and p-toluenesulfonyl chloride (10 mmol) is added. The progress of the reaction is followed by tlc, and when complete, the solution is added to dilute HCl and the product is extracted with ether. The extract is dried and evaporated to afford the bis(p-toluenesulfonyl) derivative of hexaethylene glycol.

The bis(p-toluenesulfonyl) derivative of hexaethylene glycol (1 mmol) is dissolved in dry DMF (10 mL) and $K_2CO_3$ (1 g) and 4-iodophenol (2 mmol) are added. The progress of the reaction is followed by tlc. When the reaction is complete, the solution is added to water and the product is extracted with ethyl acetate. The extract is dried and evaporated, and the product is purified by HPLC to afford compound 31 (Linker=—$O(CH_2CH_2O)_6$—).

Example 1

Synthesis of Compound 12 (see FIG. 8)

In this example, compound 12 (where n is 3) is prepared as shown in FIG. 8. To a mixture of $K_2CO_3$ (1 g) and 9 (from Example C) (2 mmol) in dry DMF at 50° C. is added a solution of dibromide 11 (wherein n=3), (1 mmol) in DMF (5 mL). The reaction is monitored by tlc until it is complete, then the mixture is added to water. The product is extracted with ethyl acetate, and the extract is dried and evaporated. The residue is then purified by HPLC to afford 12. In a similar manner, other compounds with varying n can be prepared.

Example 2

Synthesis of Compound 22 (see FIG. 12)

In this example, compound 22 (where n=2 and Linker=—$(CH_2)_{10}$—) is prepared as shown in FIG. 12. Dicyclohexylcarbodiimide (1 mmol) is dissolved in dry $CH_2Cl_2$ (25 mL) and dodecanedicarboxylic acid (21, Linker=—$(CH_2)_{10}$—), (1 mmol) is added, followed by the intermediate 20 (n=2) (from Example F) (0.5 mmol). The reaction is followed by tlc, and when it is complete, the solution is added to water and extracted with $CH_2Cl_2$. The extract is washed with dilute aqueous $NaHCO_3$, then dried and evaporated. The residue is purified by HPLC to afford compound 22 (where n=2 and Linker=—$(CH_2)_{10}$—).

Example 3

Synthesis of Compound 24 (see FIG. 13)

In this example, compound 24 (where n=2 and Linker=—$(CH_2)_{10}$—) is prepared as shown in FIG. 13. Compound 17 (from Example E) (1 mmol) is dissolved in dry $CH_2Cl_2$ (25 mL) and dicyclohexylcarbodiimide (1 mmol) is added, followed by 1,10-diaminodecane (0.5 mmol). The progress of the reaction is followed by tlc. When the reaction is complete, the solution is washed with dilute HCl, dilute aqueous $NaHCO_3$, then dried and evaporated. Compound 24 (n=4 and Linker=—$(CH_2)_{10}$—) is then purified by HPLC.

Example 4

Synthesis of Compound 32 (see FIG. 16)

In this example, compound 32 (where Linker=—$O(CH_2CH_2O)_6$—) is prepared as shown in FIG. 16. Compound 28 (0.5 mmol), tetrakis(triphenylphosphine)Pd(0) (25 mg), and the bis(iodophenyl) compound 31 (Linker is —$O(CH_2CH_2O)_6$—) (0.25 mmol) and $NaHCO_3$ (50 mg) are refluxed under an inert atmosphere in a mixture of toluene (10 mL), ethanol (1 mL) and water (1 mL). The progress of the reaction is followed by tlc. When the reaction is complete, the solution is filtered and the solvent is removed under vacuum. The residue is purified by HPLC to afford the linked compound 32 (Linker=—$O(CH_2CH_2O)_6$—).

Bioassay Example 1

Rat Carrageenan Foot Pad Edema Test

The carrageenan foot edema test can be performed with materials, reagents and procedures essentially as described by Winter et al. (*Proc. Soc. Exp. Biol. Med.*, 111, 544 (1962)). Male Sprague-Dawley rats are selected in each group so that the average body weight is as close as possible. Rats are fasted with free access to water for over sixteen hours prior to the test. The rats are dosed orally (1 mL) with the test compound suspended in vehicle containing 0.5% methylcellulose and 0.025% surfactant, or with vehicle alone. One hour later a subplantar injection of 0.1 mL of 1% solution of carrageenan/sterile 0.9% saline is administered and the volume of the injected foot is measured with a displacement plethysmometer connected to a pressure transducer with a digital indicator. Three hours after the injection of the carrageenan, the volume of the foot is again measured. The average foot swelling in a group of drug-treated animals is compared with that of a group of placebo-treated animals and the percentage inhibition of edema is determined Otterhess and Bliven, Laboratory Models for Testing NSAIDs, in *Non-steroidal Anti-Inflammatory Drugs*, J. Lombardino, ed. 1985).

Bioassay Example 2

Evaluation of COX-1 and COX-2 Activity In Vitro

The COX-2 inhibition activity of the compounds of this invention can be determined using the following methods.

A. Preparation of Recombinant COX Baculoviruses

Recombinant COX-1 and COX-2 were prepared as described by Gierse et al, [*J. Blochem.*, 305, 479–84 (1995)]. A 2.0 kb fragment containing the coding region of either human or murine COX-1 or human or murine COX-2 is cloned into a BamH1 site of the baculovirus transfer vector pVL1393 (Invitrogen) to generate the baculovirus transfer vectors for COX-1 and COX-2 in a manner similar to the method of D. R. O'Reilly et al (Baculovirus Expression Vectors: A Laboratory Manual (1992)). Recombinant baculoviruses are isolated by transfecting 4 µg of baculovirus transfer vector DNA into SF9 insect cells ($2 \times 10^8$) along with 200 ng of linearized baculovirus plasmid DNA by the calcium phosphate method. See M. D. Summers and G. E. Smith, *A Manual of Methods for Baculovirus Vectors and Insect Cell Culture Procedures*, Texas Agric. Exp. Station Bull. 1555 (1987). Recombinant viruses are purified by three rounds of plaque purification and high titer ($10^7$–$10^8$ pfu/mL) stocks of virus are prepared. For large scale production, SF9 insect cells are infected in 10 liter fermentors ($0.5 \times 10^6$ mL) with the recombinant baculovirus stock such that the multiplicity of infection is 0.1. After 72 hours, the cells are centrifuged and the cell pellet homogenized in Tris/Sucrose (50 mM: 25%, pH 8.0) containing 1% 3-[(3-cholamidopropyl)-dimethylammonio]-1-propanesulfonate (CHAPS). The homogenate is centrifuged at 10,000×G for 30 minutes, and the resultant supernatant is stored at –80° C. before being assayed for COX activity.

B. Assay for COX-1 and COX-2 Activity

COX activity is assayed as $PGE_2$ formed/µg protein/time using an ELISA to detect the prostaglandin released.

CHAPS-solubilized insect cell membranes containing the appropriate COX enzyme are incubated in a potassium phosphate buffer (50 mM, pH 8.0) containing epinephrine, phenol, and heme with the addition of arachidonic acid (10 µM). Compounds are pre-incubated with the enzyme for 10–20 minutes prior to the addition of arachidonic acid. Any reaction between the arachidonic acid and the enzyme is stopped after ten minutes at 37° C./room temperature by transferring 40 µL of reaction mix into 160 µL ELISA buffer and 25 µM indomethacin. The $PGE_2$ formed is measured by standard ELISA technology (Cayman Chemical).

What is claimed is:

1. A compound of formula I:

    I wherein each L is a ligand independently selected from formula IA, IB or IC:

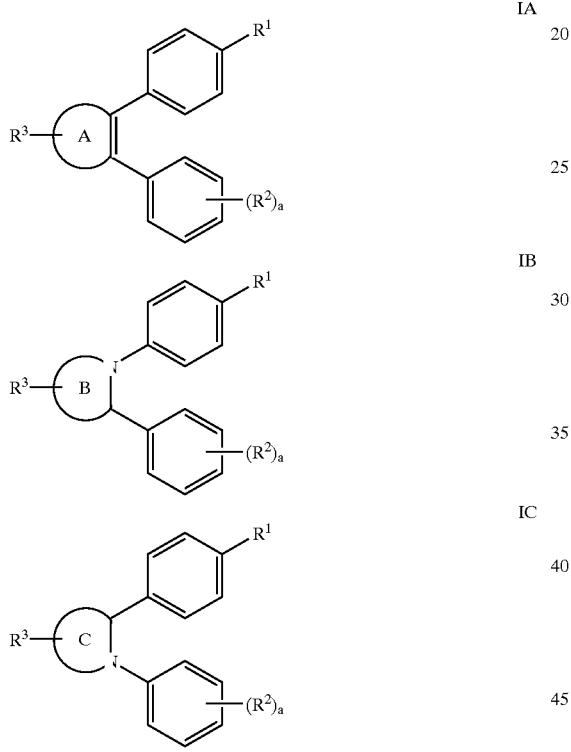

wherein
ring A, together with the atoms to which it is attached, forms a cyclobut-2-en-1-one, thiazole, isothiazole, thiadiazole, oxazole, isoxazole, 5(H)-furanone, benzene, pyridine, imidazopyridine, imidazothiazole or thiazolotriazole ring;
ring B, together with the atoms to which it is attached, forms a pyrazole ring;
ring C, together with the atoms to which it is attached, forms an imidazole ring;
$R^1$ is selected from the group consisting of —$SO_2CH_3$, —$SO_2NH_2$, —$SO_2NHC(O)CF_3$, —$SO_2(NH)NH_2$ and —$SO(NH)NHC(O)CF_3$;
each $R^2$ is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;

$R^3$ is a covalent bond linking the ligand to a linker; and
α is an integer from 0 to 3; and
each X is independently a linker of the formula:

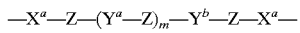

wherein
m is an integer of from 0 to 20;
$X^a$ at each separate occurrence is selected from the group consisting of —O—, —S—, —NR—, —C(O)—, —C(O)O—, —C(O)NR—, —C(S)—, —C(S)O—, —C(S)NR— and a covalent bond where R is as defined below;
Z is at each separate occurrence is selected from the group consisting of alkylene, substituted alkylene, cycloalkylene, substituted cycloalkylene, alkenylene, substituted alkenylene, alkynylene, substituted alkynylene, cycloalkenylene, substituted cycloalkenylene, arylene, heteroarylene, heterocyclene, and a covalent bond;
$Y^a$ and $Y^b$ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —P(O)(OR')—O—, —S(O)$_n$CR'R"—, —S(O)$_n$—NR'—, —S—S— and a covalent bond; where n is 0, 1 or 2;
R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;
p is an integer of from 2 to 10;
q is an integer of from 1 to 20, provided that q is less than p;
and pharmaceutically-acceptable salts thereof.

2. A compound of formula II:

    II wherein each L' is a ligand independently selected from the group consisting of:
(a) a ligand of formula IIA:

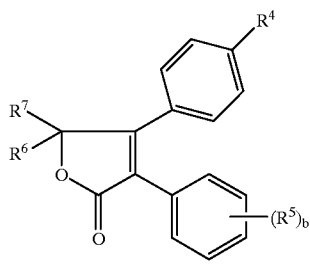

wherein
$R^4$ is selected from the group consisting of —$SO_2CH_3$, —$SO_2NH_2$, —$SO_2NHC(O)CF_3$, —$SO(NH)NH_2$ and —$SO(NH)NHC(O)CF_3$;
each $R^5$ is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;

R[6] is selected from the group consisting of hydrogen, alkyl, substituted alkyl, aryl, cyano, fluoro and heteroaryl;
R[7] is a covalent bond linking the ligand to a linker; and
b is an integer from 0 to 3;

(b) a ligand of formula IIB:

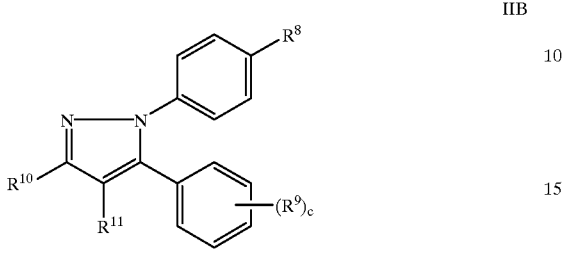

IIB wherein
R[8] is selected from the group consisting of —SO$_2$CH$_3$, —SO$_2$NH$_2$, —SO$_2$NHC(O)CF$_3$, —SO(NH)NH$_2$ and —SO(NH)NHC(O)CF$_3$;
each R[9] is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;
R[10] is a covalent bond linking the ligand to a linker;
R[11] is selected from the group consisting of hydrogen, alkyl, substituted alkyl and fluoro; and
c is an integer from 0 to 3; and (c) a ligand of formula IIC:

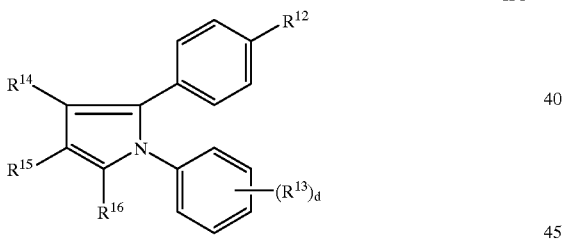

IIC wherein
R[12] is selected from the group consisting of —SO$_2$CH$_3$, —SO$_2$NH$_2$, —SO$_2$NHC(O)CF$_3$, —SO(NH)NH$_2$ and —SO(NH)NHC(O)CF$_3$;
each R[13] is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;
R[14] and R[16] are independently selected from the group consisting of hydrogen, alkyl, substituted alkyl and fluoro;
R[15] is a covalent bond linking the ligand to a linker; and
d is an integer from 0 to 3; and
X' is a linker of the formula:

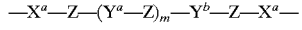

wherein
m is an integer of from 0 to 20;

X$^a$ at each separate occurrence is selected from the group consisting of —O—, —S—, —NR—, —C(O)—, —C(O)O—, —C(O)NR—, —C(S)—, —C(S)O—, —C(S)NR— and a covalent bond where R is as defined below;
Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, and a covalent bond;
Y$^a$ and Y$^b$ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —P(O)(OR')—O—, —S(O)$_n$CR'R"—, —S(O)$_n$—NR'—, —S—S— and a covalent bond; where n is 0, 1 or 2;
R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;
and pharmaceutically-acceptable salts thereof.

3. A compound of formula III:

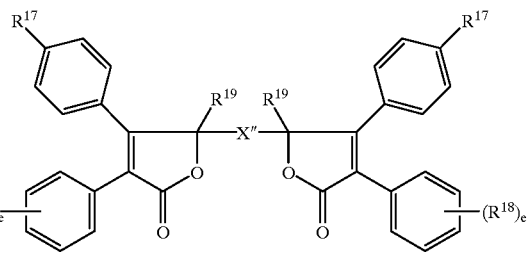

III wherein
each R[17] is independently selected from the group consisting of —SO$_2$CH$_3$, —SO$_2$NH$_2$, —SO$_2$NHC(O)CF$_3$, —SO(NH)NH$_2$ and —SO(NH)NHC(O)CF$_3$;
each R[18] is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;
each R[19] is selected from the group consisting of hydrogen, alkyl, substituted alkyl, aryl, cyano, fluoro and heteroaryl;
e is an integer from 0 to 3; and
X" is a linker of the formula:

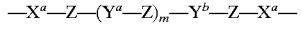

wherein
m is an integer of from 0 to 20;
X$^a$ at each separate occurrence is selected from the group consisting of —O—, —S—, —NR—, —C(O)—, —C(O)O—, —C(O)NR—, —C(S)—, —C(S)O—, —C(S)NR— and a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, and a covalent bond;

$Y^a$ and $Y^b$ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —P(O)(OR')—O—, —S(O)$_n$CR'R"—, —S(O)$_n$—NR'—, —S—S— and a covalent bond; where n is 0, 1 or 2;

R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;

and pharmaceutically-acceptable salts thereof.

4. A compound of formula IV:

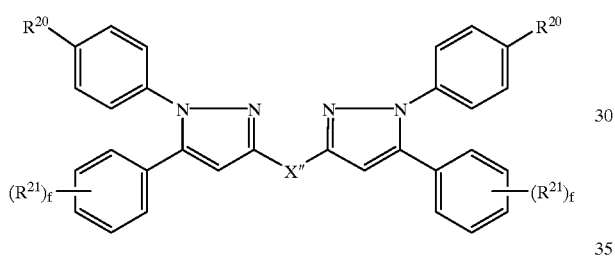

IV wherein
each $R^{20}$ is independently selected from the group consisting of —SO$_2$CH$_3$, —SO$_2$NH$_2$, —SO$_2$NHC(O)CF$_3$, —SO(NH)NH$_2$ and —SO(NH)NHC(O)CF$_3$;

each $R^{21}$ is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;

f is an integer from 0 to 3; and

X" is a linker of the formula:

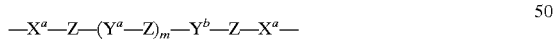

wherein
m is an integer of from 0 to 20;

$X^a$ at each separate occurrence is selected from the group consisting of —O—, —S—, —NR—, —C(O)—, —C(O)O—, —C(O)NR—, —C(S)—, —C(S)O—, —C(S)NR— and a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, and a covalent bond;

$Y^a$ and $Y^b$ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —P(O)(OR')—O—, —S(O)$_n$CR'R"—, —S(O)$_n$—NR'—, —S—S— and a covalent bond; where n is 0, 1 or 2;

R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;

and pharmaceutically-acceptable salts thereof.

5. A compound of formula V:

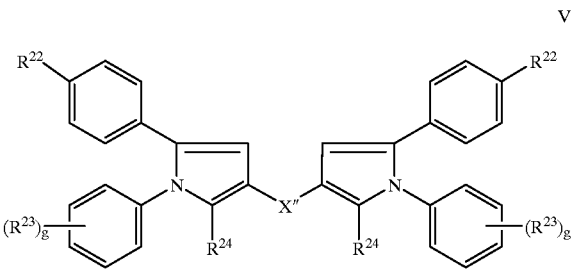

V wherein
each $R^{22}$ is independently selected from the group consisting of —SO$_2$CH$_3$, —SO$_2$NH$_2$, —SO$_2$NHC(O)CF$_3$, —SO(NH)NH$_2$ and —SO(NH)NHC(O)CF$_3$;

each $R^{23}$ is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;

each $R^{24}$ is selected from the group consisting of hydrogen, alkyl, substituted alkyl, aryl, cyano, fluoro and heteroaryl;

g is an integer from 0 to 3; and

X" is a linker of the formula:

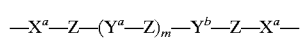

wherein
m is an integer of from 0 to 20;

$X^a$ at each separate occurrence is selected from the group consisting of —O—, —S—, —NR—, —C(O)—, —C(O)O—, —C(O)NR—, —C(S)—, —C(S)O—, —C(S)NR— and a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, and a covalent bond;

$Y^a$ and $Y^b$ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —P(O)(OR')—O—, —S(O)$_n$CR'R"—, —S(O)$_n$—NR'—, —S—S— and a covalent bond; where n is 0, 1 or 2;

R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;

and pharmaceutically-acceptable salts thereof.

6. A pharmaceutical composition comprising a pharmaceutically acceptable carrier and an effective amount of a compound of formula I:

$$(L)_p(X)_q \quad \quad I$$

wherein each L is a ligand independently selected from formula IA, IB or IC:

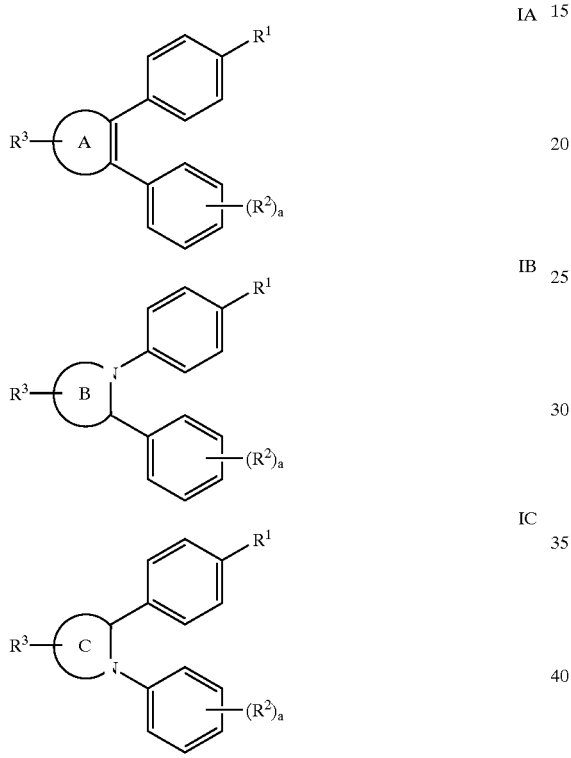

wherein ring A, together with the atoms to which it is attached, forms a cyclobut-2-en-1-one, thiazole, isothiazole, thiadiazole, oxazole, isoxazole, S(H)-furanone, benzene, pyridine, imidazopyridine, imidazothiazole or thiazolotriazole ring;

ring B, together with the atoms to which it is attached, forms a pyrazole ring;

ring C, together with the atoms to which it is attached, forms an imidazole ring;

$R^1$ is selected from the group consisting of $-SO_2CH_3$, $-SO_2NH_2$, $-SO_2NHC(O)CF_3$, $-SO(NH)NH_2$ and $-SO(NH)NHC(O)CF_3$;

each $R^2$ is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;

$R^3$ is a covalent bond linking the ligand to a linker; and α is an integer from 0 to 3;

each X is independently a linker of the formula:

$$-X^a-Z-(Y^a-Z)_m-Y^b-Z-X^a-$$

wherein m is an integer of from 0 to 20;

$X^a$ at each separate occurrence is selected from the group consisting of $-O-$, $-S-$, $-NR-$, $-C(O)-$, $-C(O)O-$, $-C(O)NR-$, $-C(S)-$, $-C(S)O-$, $-C(S)NR-$ and a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, and a covalent bond;

$Y^a$ and $Y^b$ at each separate occurrence are selected from the group consisting of $-C(O)NR'-$, $-NR'C(O)-$, $-NR'C(O)NR'-$, $-C(=NR')-NR'-$, $-NR'-C(=NR')-$, $-NR'-C(O)-O-$, $-P(O)(OR')-O-$, $-S(O)_nCR'R''-$, $-S(O)_n-NR'-$, $-S-S-$ and a covalent bond; where n is 0, 1 or 2;

R, R' and R'' at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;

p is an integer of from 2 to 10;

q is an integer of from 1 to 20, provided that q is less than p;

and pharmaceutically-acceptable salts thereof.

7. A pharmaceutical composition comprising a pharmaceutically acceptable carrier and an effective amount of a compound of formula II:

$$L'-X'-L' \quad \quad II$$

wherein each L' is a ligand independently selected from the group consisting of:

(a) a ligand of formula IIA:

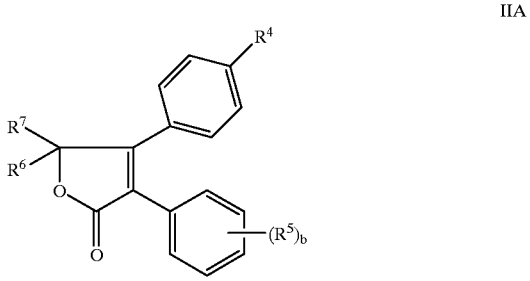

wherein $R^4$ is selected from the group consisting of $-SO_2CH_3$, $-SO_2NH_2$, $-SO_2NHC(O)CF_3$, $-SO(NH)NH_2$ and $-SO(NH)NHC(O)CF_3$;

each $R^5$ is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;

$R^6$ is selected from the group consisting of hydrogen, alkyl, substituted alkyl, aryl, cyano, fluoro and heteroaryl;

R[7] is a covalent bond linking the ligand to a linker; and b is an integer from 0 to 3;

(b) a ligand of formula IIB:

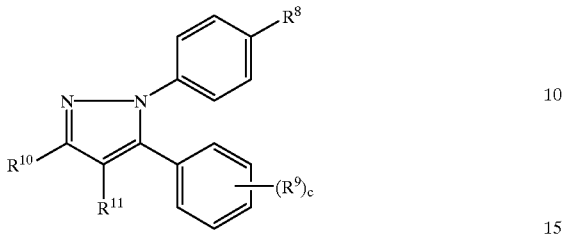

IIB wherein

R[8] is selected from the group consisting of —SO$_2$CH$_3$, —SO$_2$NH$_2$, —SO$_2$NHC(O)CF$_3$, —SO(NH)NH$_2$ and —SO(NH)NHC(O)CF$_3$;

each R[9] is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;

R[10] is a covalent bond linking the ligand to a linker;

R[11] is selected from the group consisting of hydrogen, alkyl, substituted alkyl and fluoro; and c is an integer from 0 to 3; and (c) a ligand of formula IIC:

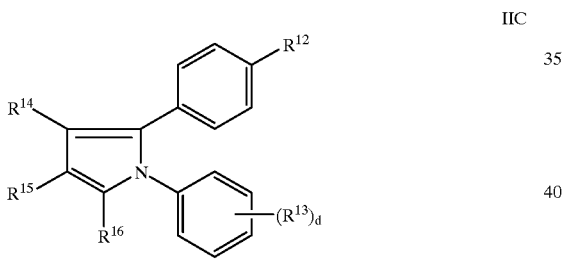

IIC wherein

R[12] is selected from the group consisting of —SO$_2$CH$_3$, —SO$_2$NH$_2$, —SO$_2$NHC(O)CF$_3$, —SO(NH)NH$_2$ and —SO(NH)NHC(O)CF$_3$;

each R[13] is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;

R[14] and R[16] are independently selected from the group consisting of hydrogen, alkyl, substituted alkyl and fluoro;

R[15] is a covalent bond linking the ligand to a linker; and d is an integer from 0 to 3; and X' is a linker of the formula:

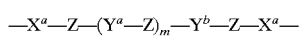

wherein m is an integer of from 0 to 20;

X$^a$ at each separate occurrence is selected from the group consisting of —O—, —S—, —NR—, —C(O)—, —C(O)O—, —C(O)NR—, —C(S)—, —C(S)O—, —C(S)NR— and a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, and a covalent bond;

Y$^a$ and Y$^b$ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —P(O)(OR')—O—, —S(O)$_n$CR'R"—, —S(O)$_n$—NR'—, —S—S— and a covalent bond;

where n is 0, 1 or 2;

R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;

and pharmaceutically-acceptable salts thereof.

8. A pharmaceutical composition comprising a pharmaceutically acceptable carrier and an effective amount of a compound of formula III:

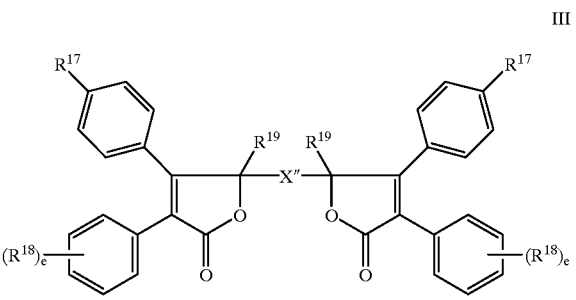

III wherein each R[17] is independently selected from the group consisting of —SO$_2$CH$_3$, —SO$_2$NH$_2$, —SO$_2$NHC(O)CF$_3$, —SO(NH)NH$_2$ and —SO(NH)NHC(O)CF$_3$;

each R[18] is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;

each R[19] is selected from the group consisting of hydrogen, alkyl, substituted alkyl, aryl, cyano, fluoro and heteroaryl;

e is an integer from 0 to 3; and

X" is a linker of the formula:

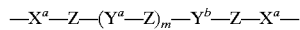

wherein m is an integer from 0 to 20;

X$^a$ at each separate occurrence is selected from the group consisting of —O—, —S—, —NR—, —C(O)—, —C(O)O—, —C(O)NR—, —C(S)—, —C(S)O—, —C(S)NR— and a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, and a covalent bond;

$Y^a$ and $Y^b$ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —P(O)(OR')—O—, —S(O)$_n$CR'R"—, —S(O)$_n$—NR'—, —S—S— and a covalent bond; where n is 0, 1 or 2;

R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;

and pharmaceutically-acceptable salts thereof.

9. A pharmaceutical composition comprising a pharmaceutically acceptable carrier and an effective amount of a compound of formula IV:

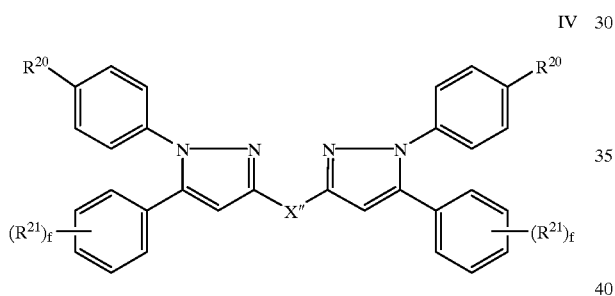

IV wherein
each $R^{20}$ is independently selected from the group consisting of —SO$_2$CH$_3$, —SO$_2$NH$_2$, —SO$_2$NHC(O)CF$_3$, —SO(NH)NH$_2$ and —SO(NH)NHC(O)CF$_3$;

each $R^{21}$ is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;

f is an integer from 0 to 3; and
X" is a linker of the formula:

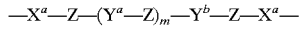

wherein
m is an integer of from 0 to 20;
$X^a$ at each separate occurrence is selected from the group consisting of —O—, —S—, —NR—, —C(O)—, —C(O)O—, —C(O)NR—, —C(S)—, —C(S)O—, —C(S)NR— and a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, and a covalent bond;

$Y^a$ and $Y^b$ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —P(O)(OR')—O—, —S(O)$_n$CR'R"—, —S(O)$_n$—NR'—, —S—S— and a covalent bond; where n is 0, 1 or 2;

R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;

and pharmaceutically-acceptable salts thereof.

10. A pharmaceutical composition comprising a pharmaceutically acceptable carrier and an effective amount of a compound of formula V:

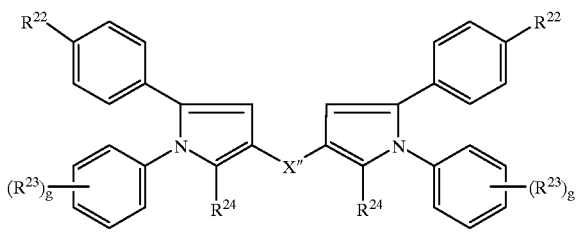

V wherein
each $R^{22}$ is independently selected from the group consisting of —SO$_2$CH$_3$, —SO$_2$NH$_2$, —SO$_2$NHC(O)CF$_3$, —SO(NH)NH$_2$ and —SO(NH)NHC(O)CF$_3$;

each $R^{23}$ is independently selected from the group consisting of alkyl, substituted alkyl, alkoxy, substituted alkoxy, alkoxycarbonyl, amino, substituted amino, azido, carboxyl, cyano, cycloalkyl, substituted cycloalkyl, halo, hydroxyl, nitro, thioalkoxy and substituted thioalkoxy;

each $R^{24}$ is selected from the group consisting of hydrogen, alkyl, substituted alkyl, aryl, cyano, fluoro and heteroaryl;

g is an integer from 0 to 3; and
X" is a linker of the formula:

—X$^a$—Z—(Y$^a$—Z)$_m$—Y$^b$—Z—X$^a$— wherein
m is an integer of from 0 to 20;
$X^a$ at each separate occurrence is selected from the group consisting of —O—, —S—, —NR—, —C(O)—, —C(O)O—, —C(O)NR—, —C(S)—, —C(S)O—, —C(S)NR— and a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, and a covalent bond;

$Y^a$ and $Y^b$ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —P(O)(OR')—O—, —S(O)$_n$CR'R"—, —S(O)$_n$—NR'—, —S—S— and a covalent bond; where n is 0, 1 or 2;

R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic;

and pharmaceutically-acceptable salts thereof.

* * * * *

UNITED STATES PATENT AND TRADEMARK OFFICE
CERTIFICATE OF CORRECTION

| | | |
|---|---|---|
| PATENT NO. | : 6,395,724 B1 | Page 1 of 1 |
| APPLICATION NO. | : 09/326916 | |
| DATED | : May 28, 2002 | |
| INVENTOR(S) | : J. Kevin Judice, Deborah L. Higgins and John H. Griffin | |

It is certified that error appears in the above-identified patent and that said Letters Patent is hereby corrected as shown below:

Column 115,
Formula IB and IC " ∫ " should read -- N --.

Column 116,
Line 2, "α" should read -- a --.

Signed and Sealed this

Eighteenth Day of July, 2006

JON W. DUDAS
*Director of the United States Patent and Trademark Office*